US010836787B2

(12) United States Patent
Brak et al.

(10) Patent No.: US 10,836,787 B2
(45) Date of Patent: Nov. 17, 2020

(54) CRYSTALLINE FORMS OF (S)-2-ETHYLBUTYL 2-(((S)-(((2R,3S,4R,5R)-5-(4-AMINOPYRROLO[2,1-F][1,2,4]TRIAZIN-7-YL)-5-CYANO-3,4-DIHYDROXYTETRAHYDROFURAN-2-YL)METHOXY)(PHENOXY)PHOSPHORYL)AMINO)PROPANOATE

(71) Applicant: Gilead Sciences, Inc., Foster City, CA (US)

(72) Inventors: Katrien Brak, Belmont, CA (US); Ernest A. Carra, Foster City, CA (US); Lars V. Heumann, Redwood City, CA (US); Nate Larson, Saint George, UT (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/964,597

(22) Filed: Apr. 27, 2018

(65) Prior Publication Data

US 2018/0346504 A1    Dec. 6, 2018

Related U.S. Application Data

(60) Provisional application No. 62/492,364, filed on May 1, 2017.

(51) Int. Cl.
*C07H 19/00* (2006.01)
*A61P 31/14* (2006.01)
*C07F 9/6561* (2006.01)

(52) U.S. Cl.
CPC .............. *C07H 19/00* (2013.01); *A61P 31/14* (2018.01); *C07F 9/6561* (2013.01); *C07B 2200/13* (2013.01)

(58) Field of Classification Search
CPC ........ C07F 9/6561; C07H 19/00; A61P 31/14; C07B 2200/13
See application file for complete search history.

(56) References Cited

U.S. PATENT DOCUMENTS

| 4,816,570 | A  | 3/1989  | Farquhar          |
| 4,968,788 | A  | 11/1990 | Farquhar          |
| 5,663,159 | A  | 9/1997  | Starrett, Jr. et al. |
| 5,792,756 | A  | 8/1998  | Starrett, Jr. et al. |
| 6,312,662 | B1 | 11/2001 | Erion et al.      |
| 6,476,030 | B1 | 11/2002 | Carling et al.    |
| 6,656,915 | B1 | 12/2003 | Bantia et al.     |
| 6,909,011 | B2 | 6/2005  | Skranc et al.     |
| 7,105,493 | B2 | 9/2006  | Sommadossi et al. |
| 7,125,855 | B2 | 10/2006 | Bhat et al.       |
| 7,176,203 | B2 | 2/2007  | Chambers et al.   |
| 7,268,119 | B2 | 9/2007  | Cook et al.       |
| 7,285,658 | B2 | 10/2007 | Cook et al.       |
| 7,368,437 | B1 | 5/2008  | Bojack et al.     |
| 7,390,791 | B2 * | 6/2008 | Becker ............ C12Q 1/18 514/44 R |
| 7,429,571 | B2 | 9/2008  | Chand et al.      |
| 7,514,410 | B2 | 4/2009  | Babu et al.       |
| 7,560,434 | B2 | 7/2009  | Babu et al.       |
| 7,598,230 | B2 | 10/2009 | Cook et al.       |
| 7,608,597 | B2 | 10/2009 | Sommadossi et al. |
| 7,713,941 | B2 | 5/2010  | Cook et al.       |
| 7,803,788 | B2 | 9/2010  | Becker et al.     |
| 7,807,653 | B2 | 10/2010 | Cook et al.       |
| 7,842,672 | B2 | 11/2010 | Boojamra et al.   |
| 7,951,787 | B2 | 5/2011  | McGuigan          |

(Continued)

FOREIGN PATENT DOCUMENTS

| CA | 2367921 C | 7/2009 |
| CN | 1291994 A | 4/2001 |

(Continued)

OTHER PUBLICATIONS

Alessandrini, et al., Synthesis of Differently Protected 1-C-methyl-ribofuranoses Intermediates for the Preparation of Biologically Active 1'-C-methyl-ribonucleosides, Journal of Carbohydrate Chemistry, 2008, pp. 332-344, vol. 27, No. 5.

(Continued)

*Primary Examiner* — Lawrence E Crane
(74) *Attorney, Agent, or Firm* — Mintz, Levin, Cohn, Ferris, Glovsky and Popeo, P.C.

(57) ABSTRACT

The present invention relates to novel salts and crystalline forms of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate having the structure:

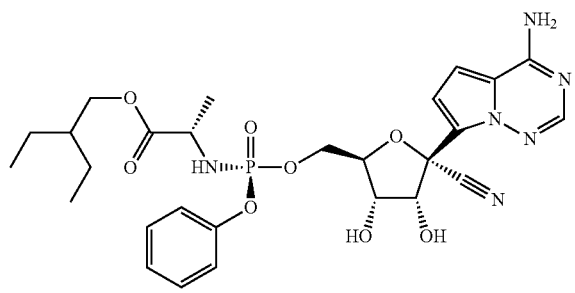

for use in treating viral infections. One crystalline form of the compound can be characterized by an X-ray powder diffraction (XRPD) pattern having peaks at 22.3°, 16.9°, and 16.2° 2-θ±0.2° 2-θ. In some embodiments, the viral infection is caused by a virus selected from the group consisting of Arenaviridae, Coronaviridae, Filoviridae, Flaviviridae, and Paramyxoviridae.

12 Claims, 29 Drawing Sheets

(56) References Cited

U.S. PATENT DOCUMENTS

| | | | |
|---|---|---|---|
| 7,973,013 | B2 | 7/2011 | Cho et al. |
| 7,994,139 | B2 | 8/2011 | Babu et al. |
| 8,008,264 | B2 | 8/2011 | Butler et al. |
| 8,012,941 | B2 | 9/2011 | Cho et al. |
| 8,012,942 | B2 | 9/2011 | Butler et al. |
| 8,071,568 | B2 | 12/2011 | Narjes et al. |
| 8,119,607 | B2 | 2/2012 | Francom et al. |
| 8,242,085 | B2 | 8/2012 | Babu et al. |
| 8,318,682 | B2 | 11/2012 | Butler et al. |
| 8,415,308 | B2 * | 4/2013 | Cho .............. A61K 31/40 514/23 |
| 8,455,451 | B2 | 6/2013 | Cho et al. |
| 8,853,171 | B2 | 10/2014 | Butler et al. |
| 8,871,737 | B2 | 10/2014 | Smith et al. |
| 8,889,159 | B2 * | 11/2014 | Cleary ............ A61K 9/2009 424/400 |
| 8,980,865 | B2 | 3/2015 | Wang |
| 9,090,642 | B2 | 7/2015 | Cho et al. |
| 9,243,022 | B2 | 1/2016 | Beigelman et al. |
| 9,249,174 | B2 | 2/2016 | Beigelman et al. |
| 9,278,990 | B2 | 3/2016 | Smith et al. |
| 9,388,208 | B2 * | 7/2016 | Clarke ............ C07D 487/04 |
| 9,393,256 | B2 * | 7/2016 | Ray .................. A61K 45/06 |
| 9,452,154 | B2 * | 9/2016 | Delaney, IV ...... A61K 31/706 |
| 9,481,703 | B2 | 11/2016 | Kalayanov et al. |
| 9,487,544 | B2 * | 11/2016 | Cho ................ C07F 9/6561 |
| 9,504,701 | B2 | 11/2016 | Casola et al. |
| 9,540,411 | B2 | 1/2017 | Kalayanov et al. |
| 9,549,941 | B2 * | 1/2017 | Cleary ............ A61K 9/2009 |
| 9,605,018 | B2 | 3/2017 | Wang et al. |
| 9,616,076 | B2 | 4/2017 | Casola et al. |
| 9,701,682 | B2 * | 7/2017 | Clarke ............ C07F 9/6561 |
| 9,724,360 | B2 * | 8/2017 | Chun .............. A61K 31/6615 |
| 9,828,408 | B2 | 11/2017 | Kalayanov |
| 9,949,994 | B2 * | 4/2018 | Chun .............. A61K 31/665 |
| 10,023,600 | B2 | 7/2018 | Butler et al. |
| 10,034,893 | B2 | 7/2018 | Luly et al. |
| 10,059,716 | B2 | 8/2018 | Clarke et al. |
| 10,065,958 | B2 * | 9/2018 | Mackman ........... A61K 45/06 |
| 10,251,898 | B2 * | 4/2019 | Chun .............. A61K 31/665 |
| 10,251,904 | B2 * | 4/2019 | Clarke ............ A61K 31/706 |
| 10,377,761 | B2 | 8/2019 | Clarke et al. |
| RE47,589 | E * | 9/2019 | McGuigan ........... C07H 19/10 |
| 2003/0050229 | A1 | 3/2003 | Sommadossi et al. |
| 2004/0006002 | A1 | 1/2004 | Sommadossi et al. |
| 2004/0023901 | A1 | 2/2004 | Cook et al. |
| 2004/0063658 | A1 | 4/2004 | Roberts et al. |
| 2004/0067901 | A1 | 4/2004 | Bhat et al. |
| 2004/0138170 | A1 | 7/2004 | Montgomery et al. |
| 2005/0187180 | A1 | 8/2005 | Loeb et al. |
| 2005/0209166 | A1 | 9/2005 | Eckhardt et al. |
| 2005/0215513 | A1 | 9/2005 | Boojamra et al. |
| 2005/0250728 | A1 | 11/2005 | Bantia et al. |
| 2006/0058303 | A1 | 3/2006 | Chambers et al. |
| 2006/0142238 | A1 | 6/2006 | McGuigan |
| 2006/0241064 | A1 | 10/2006 | Roberts et al. |
| 2008/0107628 | A1 | 5/2008 | Boojamra et al. |
| 2008/0161324 | A1 | 7/2008 | Johansen et al. |
| 2008/0280842 | A1 | 11/2008 | MacCoss et al. |
| 2009/0004138 | A1 | 1/2009 | Francom et al. |
| 2009/0221524 | A1 | 9/2009 | Kotra et al. |
| 2009/0233879 | A1 | 9/2009 | Reddy et al. |
| 2009/0317361 | A1 | 12/2009 | Cho et al. |
| 2010/0015094 | A1 | 1/2010 | Babu et al. |
| 2010/0016251 | A1 | 1/2010 | Sofia et al. |
| 2010/0021425 | A1 | 1/2010 | Butler et al. |
| 2010/0035835 | A1 | 2/2010 | Narjes et al. |
| 2010/0035836 | A1 | 2/2010 | Francom et al. |
| 2010/0203015 | A1 | 8/2010 | Butler et al. |
| 2010/0234584 | A1 | 9/2010 | Chang |
| 2010/0291031 | A2 | 11/2010 | Francom et al. |
| 2010/0298257 | A1 | 11/2010 | Ross et al. |
| 2011/0070194 | A1 | 3/2011 | Cho et al. |
| 2011/0084230 | A1 | 4/2011 | Knochel et al. |
| 2011/0230654 | A1 | 9/2011 | Butler et al. |
| 2011/0257122 | A1 | 10/2011 | Sofia et al. |
| 2011/0293563 | A1 | 12/2011 | Butler et al. |
| 2012/0009147 | A1 | 1/2012 | Cho et al. |
| 2012/0020921 | A1 | 1/2012 | Cho et al. |
| 2012/0027752 | A1 | 2/2012 | Mackman et al. |
| 2012/0071434 | A1 | 3/2012 | Smith et al. |
| 2012/0107274 | A1 | 5/2012 | Clarke et al. |
| 2013/0034521 | A1 | 2/2013 | Butler et al. |
| 2013/0143835 | A1 | 6/2013 | Eneroth et al. |
| 2013/0281686 | A1 | 10/2013 | Cho et al. |
| 2013/0315868 | A1 | 11/2013 | Mayes |
| 2013/0344028 | A2 | 12/2013 | Butler et al. |
| 2014/0219958 | A1 | 8/2014 | Luly et al. |
| 2015/0111839 | A1 | 4/2015 | Mackman et al. |
| 2015/0133395 | A1 | 5/2015 | Clarke et al. |
| 2015/0152116 | A1 | 6/2015 | Mackman et al. |
| 2016/0058779 | A1 | 3/2016 | Casola et al. |
| 2016/0122374 | A1 | 5/2016 | Chun |

FOREIGN PATENT DOCUMENTS

| | | |
|---|---|---|
| CN | 1443189 A | 9/2003 |
| CN | 1498221 A | 5/2004 |
| CN | 1852915 A | 10/2006 |
| CN | 101043893 A | 9/2007 |
| CN | 101611046 A | 12/2009 |
| CN | 102906102 A | 1/2013 |
| EA | 201071170 A1 | 8/2011 |
| EA | 201171417 A1 | 5/2012 |
| EA | 201200525 A1 | 9/2012 |
| EP | 2396340 B1 | 12/2013 |
| JP | 41017629 | 10/1966 |
| JP | 2004520367 A | 7/2004 |
| JP | 2008502685 A | 1/2008 |
| JP | 2008518934 A | 6/2008 |
| TW | 1401084 B | 7/2013 |
| WO | WO-1991/019721 A1 | 12/1991 |
| WO | WO 1999/045029 A1 | 9/1999 |
| WO | WO-2000/56734 A1 | 9/2000 |
| WO | WO-2001/32153 A2 | 5/2001 |
| WO | WO-2001/60315 A2 | 8/2001 |
| WO | WO-2001/90121 A2 | 11/2001 |
| WO | WO-2002/008241 | 1/2002 |
| WO | WO-2002/18404 A2 | 3/2002 |
| WO | WO-2002/32920 A2 | 4/2002 |
| WO | WO-2002/057287 A2 | 7/2002 |
| WO | WO-2002/057425 A2 | 7/2002 |
| WO | WO-2003/093272 A1 | 11/2003 |
| WO | WO-2003/093273 A1 | 11/2003 |
| WO | WO-2003/100009 A2 | 12/2003 |
| WO | WO-2004/046331 A1 | 6/2004 |
| WO | WO-2005/009418 A2 | 2/2005 |
| WO | WO-2005/123087 A2 | 12/2005 |
| WO | WO-2006/031725 A2 | 3/2006 |
| WO | WO-2006/050161 A2 | 5/2006 |
| WO | WO-2006/064033 A2 | 6/2006 |
| WO | WO-2006/065335 A2 | 6/2006 |
| WO | WO-2006/121820 A1 | 11/2006 |
| WO | WO-2007/027248 A2 | 3/2007 |
| WO | WO-2007/056170 A2 | 5/2007 |
| WO | WO-2007/064883 A2 | 6/2007 |
| WO | WO-2007/064931 A2 | 6/2007 |
| WO | WO-2007/065289 A2 | 6/2007 |
| WO | WO-2007/065829 A1 | 6/2007 |
| WO | WO-2007/097991 A2 | 8/2007 |
| WO | WO-2007/135134 A1 | 11/2007 |
| WO | WO-2008/005542 A2 | 1/2008 |
| WO | WO-2008/055870 A1 | 5/2008 |
| WO | WO-2008/79206 A1 | 7/2008 |
| WO | WO-2008/082601 A2 | 7/2008 |
| WO | WO-2008/085508 A2 | 7/2008 |
| WO | WO-2008/089105 A2 | 7/2008 |
| WO | WO-2008/116064 A2 | 9/2008 |
| WO | WO-2008/121634 A2 | 10/2008 |
| WO | WO-2008/141079 A1 | 11/2008 |
| WO | WO-2009/009951 A1 | 1/2009 |
| WO | WO-2009/131926 A1 | 10/2009 |
| WO | WO-2009/132123 A1 | 10/2009 |
| WO | WO-2009/132135 A1 | 10/2009 |

(56) References Cited

FOREIGN PATENT DOCUMENTS

| WO | WO-2010/002877 A2 | 1/2010 |
| --- | --- | --- |
| WO | WO-2010/036407 A2 | 4/2010 |
| WO | WO-2010/093608 A1 | 8/2010 |
| WO | WO-2010/099458 A1 | 9/2010 |
| WO | WO-2010/135569 A1 | 11/2010 |
| WO | WO-2011/011303 A1 | 1/2011 |
| WO | WO-2010/111381 A3 | 3/2011 |
| WO | WO-2011/035231 A1 | 3/2011 |
| WO | WO-2011/035250 A1 | 3/2011 |
| WO | WO 2011/080568 A2 | 7/2011 |
| WO | WO-2011/123645 A2 | 10/2011 |
| WO | WO 2011/123668 A2 | 10/2011 |
| WO | WO-2011/123672 A1 | 10/2011 |
| WO | WO-2011/150288 A1 | 12/2011 |
| WO | WO-2012/012465 A1 | 1/2012 |
| WO | WO-2012/012776 A1 | 1/2012 |
| WO | WO-2012/039787 A1 | 3/2012 |
| WO | WO-2012/039791 A1 | 3/2012 |
| WO | WO-2012/051570 A1 | 4/2012 |
| WO | WO 2012/142523 A2 | 10/2012 |
| WO | WO-2013/084165 A1 | 6/2013 |
| WO | WO 2014/033617 A1 | 3/2014 |
| WO | WO-2014/042433 A2 | 3/2014 |
| WO | WO 2014/078463 A1 | 5/2014 |
| WO | WO-2014/078778 A2 | 5/2014 |
| WO | WO-2014/116755 A1 | 7/2014 |
| WO | WO 2014/169280 A2 | 10/2014 |
| WO | WO-2015/069939 A1 | 5/2015 |
| WO | WO-2016/069825 A1 | 5/2016 |
| WO | WO-2016/069826 A1 | 5/2016 |
| WO | WO-2016/069827 A1 | 5/2016 |
| WO | WO 2017/184668 * | 10/2017 |
| WO | WO-2017/049060 A1 | 3/2018 |

OTHER PUBLICATIONS

Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.

Arimilli, M.N., et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.

ARIPO Form 21 and Substantive Examination Report (in English) for AP Application No. AP/P/2010/005439, Mar. 18, 2014.

ARIPO Patent Office, Official Action (ARIPO Form No. 18) with Substantive Search and Examination Report for AP Application No. AP/P/2010/005414, Mar. 14, 2014.

ARIPO Patent Office, Search and Exam Report for AP Application No. AP/P/2012/006189, Jun. 26, 2014.

ARIPO Patent Office, Search Report for AP Patent Application No. AP/P/2011/005818, Sep. 19, 2013.

ASBUN, et al., Synthesis of 5-substituted Pyrimidines. II, Journal of Organic Chemistry, 1968, pp. 140-142, vol. 31.

Australia Patent Office, Patent Examination Report No. 1 for AU Application No. 2011280910, Jun. 10, 2014.

Australia Patent Office, Patent Examination Report No. 1 for AU Application No. 2011306066, Nov. 21, 2013.

Australia Patent Office, Patent Examination Report No. 1 for AU Patent Application No. 2010213873, Jun. 4, 2014.

Australia Patent Office, Patent Examination Report No. 1 for AU Patent Application No. 2010295392, Sep. 16, 2014.

Australia Patent Office, Patent Examination Report No. 1 for AU Patent Application No. 2011282241, Jul. 9, 2014.

Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.

Balzarini, et al., Inhibition of feline (FIPV) and human (SARS) coronavirus by semisynthetic derivatives of glycopeptide antibiotics, Antiviral Research, Mar. 14, 2006, pp. 20-33, vol. 72.

Bandini, et al., Indium tribromide: a highly effective catalyst for the addition of trimethylsilyl cyanide to α-hetero-substituted ketone, Tetrahedron Letters, 2001, pp. 3041-3043. vol. 42.

Barker, et al., 2,3,5-Tri-O-benzyl-D-ribosyl and -L-arabinosyl Bromides, Journal of Organic Chemistry, 1961, pp. 4605-4609, vol. 26, No. 11.

Belokon, et al., Optimized catalysts for the asymmetric addition of trimethylsilyl cyanide to aldehydes and ketones, Tetrahedron, 2001, pp. 771-779, vol. 57.

Benksim, et al., A Novel Stereospecific Synthesis of Glycosyl Cyanides from 1,2-O-sulfinyl Derivatives, Organic Letters, 2004, pp. 3913-3915, vol. 6, No. 22.

Benzaria, et al., Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability, J. Med. Chem., 1996, pp. 4958-4965, vol. 39, No. 25.

Bio, et al., Practical Synthesis of a Potent Hepatitis C Virus RNA Replication Inhibitor, J. Org. Chem., 2004, pp. 6257-6266, vol. 69, No. 19.

Bobeck, et al., Advances in Nucleoside Monophosphate Prodrugs as Anti-HCV Agents, Antiviral Therapy, 2010, pp. 935-950, vol. 15.

Bojack, et al., Design and Synthesis of Inhibitors of Adenosine and AMP Deaminases, Org. Letters, 2001, pp. 839-842, vol. 3, No. 6.

Boyer, et al., Pathogenesis, diagnosis and management of hepatitis C, Journal of Hepatology, 2000, pp. 98-112, vol. 32.

Brown, Progress towards improving antiviral therapy for hepatitis C virus polymerase inhibitors. Part O: Nucleoside analogues, 2009, pp. 709-725, vol. 18.

Burns, A glimmer of hope for a fatal feline disease, American Veterinary Medical Association, Dec. 15, 2017, 5 pages.

Butora, et al., Synthesis and HCV inhibitory properties of 9-deaza- and 7,9-dideaza-7-oxa-2'-C-methyladenosine, Bioorganic & Medicinal Chemistry, 2007, pp. 5219-5229, vol. 15, No. 15.

Cabirol, et al., Robust and Efficient, yet Uncatalyzed, Synthesis of Triarylsilyl-protected Cyanohydrins from Ketones, 2008, pp. 2446-2449, vol. 73.

Calés, et al., Treatment of liver fibrosis: clinical aspects, Gastroenterologie Clinique et Biologique, 2009, pp. 958-966, vol. 33, No. 10-11.

Calisher, et al., Antigenic Relationships between Flaviviruses as Determined by Cross-neutralization Tests with Polyclonal Antisera, Journal of General Virology, 1989, pp. 37-43, vol. 70.

Camps, Studies on Structurally Simple -αβ-butenolides-II, Tetrahedron, 1982, pp. 2395-2402, vol. 38, No. 15.

Canadian Patent Office, Office Action for CA Patent Application No. 2,773,772, Aug. 12, 2014.

Carroll, Robust Antiviral Efficacy upon Administration of a Nucleoside Analog to Hepatitis C Virus-Infected Chimpanzees, Antimicrobial Agents and Chemotherapy, 2009, pp. 926-934, vol. 53, No. 3.

Chapman, et al., RSV604, a Novel Inhibitor of Respiratory Syncytial Virus Replication, Antimicrobial Agents and Chemotherapy, 2007, pp. 3346-3353, vol. 51, No. 9.

Chile Patent Office, Opposition filed Against CL Patent Application 00076-2013, Jun. 18, 2014.

Chile Patent Office, Opposition for CL Patent Application No. 727-2013, Oct. 15, 2013.

Chile Patent Office, Second Office Action for CL Patent Application No. 1906-2011, Oct. 16, 2013.

Chinese Patent Office, ffice Action for CN Patent Application No. 200980114224.2, Nov. 30, 2012.

Chinese Patent Office, Notification of Reexamination for CN Patent Application No. 200980120218.8, Sep. 1, 2014.

Chinese Patent Office, Notification of the First Office Action and Search Report for CN Patent Application No. 201080041902.X, Nov. 12, 2013.

Chinese Patent Office, Notification of the First Office Action for CN Patent Application No. 201180035776.1, dated Feb. 27, 2014.

Chinese Patent Office, Notification of the First Office Action, with Search Report, for CN Patent Application No. 201080041946.2, dated Dec. 18, 2013.

(56) References Cited

OTHER PUBLICATIONS

Chinese Patent Office, Notification of the Second Office Action & Search Report for CN Patent Application No. 201080011690.0, dated Jan. 8, 2014.
Chinese Patent Office, Notification of the Third Office Action for CN Patent Application No. 201080011690.0, dated Jul. 29, 2014.
Chinese Patent Office, Office Action for CN Patent Application No. 200980114224.2, dated Aug. 19, 2013.
Chinese Patent Office, Office Action with Search Report for CN Patent Application No. 201180035281.9, dated Jun. 27, 2014.
Chinese Patent Office, Rejection Decision for CN Patent Application No. 200980120218.8, dated Feb. 7, 2014.
Chinese Patent Office, Second Examination Report for CN Patent Application No. 200980120218.8, dated Jun. 21, 2013.
Cho, et al., Synthesis and antiviral activity of a series of 1'-substituted 4-aza-7,9-dideazaadenosine C-nucleosides, Bioorg Med Chem Letters, 2012, pp. 2705-2707, vol. 22.
Cihlar, et al., Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131, Antimicrobial Agents and Chemotherapy, 2008, pp. 655-665, vol. 52, No. 2.
Clark, et al., Design, Synthesis, and Antiviral Activity of 2'-Deoxy-2'-fluoro-2'-C-methylcytidine, a Potent Inhibitor of Hepatitis C Virus Replication, Journal of Medicinal Chemistry, 2005, pp. 5504-5508, vol. 48, No. 17.
Clarke, et al., Discovery of [beta]-d-2'-deoxy-2'-[alpha]-fluoro-4'[alpha]cyano-5-aza-7,9-dideaza adenosine as a potent nucleoside inhibitor of respiratory syncytial virus with excellent selectivity over mitochondrial, BioOrganic & Medicinal Chemistry Letters, Apr. 29, 2015, pp. 2484-2487, vol. 25, No. 12.
Colacino, et al., Synthesis and Biological Evaluation of Some 5-Nitro- and 5-Amino Derivatives of 2'-Deoxycytidine, 2',3'-Dideoxyuridine, and 2',3'-Dideoxycytidine, Nucleoside, Nucleotides & Nucleic Acids, 2003, pp. 2013-2026, vol. 22, No. 11.
Columbia Patent Office, Office Action for CO Application No. 13 004212, dated Dec. 4, 2013.
Columbia Patent Office, Office Action for CO Patent Application No. 11-109.501, dated Nov. 27, 2012.
Columbia Patent Office, Office Action for CO Patent Application No. 13-235103-1, dated Aug. 27, 2014.
Columbia Patent Office, Resolution No. 56673 for CO Patent Application No. 10-131479, dated Sep. 27, 2013.
Columbia Patent Office, Resolution No. 72986 for CO Patent Application No. 10-121513-5, Dec. 23, 2013.
Columbia Patent Office, Second Examination Report (in English) for CO Patent Application No. 10-131479, dated Jun. 20, 2013.
Communication pursuant to Article 94(3) EPC for EP Patent Application No. 10763083.2, May 2, 2014.
Communication pursuant to Article 94(3) EPC for EP Patent Application No. 11715792.5, Feb. 14, 2014.
Communication under 161/162 for EP Patent Application No. 10704068.5, Sep. 6, 2011.
Communication under 161/162 for EP Patent Application No. 10763083.2, May 11, 2012.
De Clercq, Molecular Targets for Antiviral Agents, The Journal of Pharmacology and Experimental Therapeutics, 2001, pp. 1-10, vol. 297, No. 1.
De Francesco, et al., Approaching a New Era for Hepatitis C Virus Therapy: Inhibitors of the NS3-4A Serine Protease and the NS5B RNA-Dependent RNA Polymerase, Antiviral Research, 2003, pp. 1-16, vol. 58, No. 1.
De Las Heras, Synthesis of Ribosyl and Arabinosyl Cyanides by Reaction of 1-O-Acyl Sugars with Trimethylsilyl Cyanide, Journal of the Chemical Society, Perkin Transactions 1, 1982, pp. 903-907.
De Lombaert, et al., N-Phosphonomethyl Dipeptides and Their Phosphonate Prodrugs, a New Generation of Neutral Endopeptidase (NEP, EC 3.4.24.11) Inhibitors, J. Med. Chem., 1994, pp. 498-511, vol. 37, No. 4.
Di Bisceglie, et al., The Unmet Challenges of Hepatitis C, Scientific American, Oct. 1999, pp. 80-85.
Dolzhenko, et al., Pyrazolo[1,5-a][1,3,5]Triazines(5-Aza-9-Deazapurines): Synthesis and Biological Activity, Heterocycles, 2008, pp. 1575-1622, vol. 75, No. 7.
Domingo, et al., The quasispecies (extremely heterogeneous) nature of viral RNA genome populations: biological relevance—a review, Gene, 1985, pp. 1-8, vol. 40.
Dondoni, et al., Thiazole-Based Synthesis of Formyl C-Glycosides, Journal of Organic Chemistry, 1994, pp. 6404-6414, vol. 59.
Dudfield, et al., Synthesis of C-ribosyl 1,2,4-triazolo[3,4-f][1,2,4]triazines as Inhibitors of Adenosine and AMP Deaminasses, J. Chem. Soc., Perkin Trans. 1, 1999, pp. 2937-2942.
Dudfield, et al., Synthesis of C-ribosyl Imidazo[2,14][1,2,4]triazines as Inhibitors of Adenosine and AMP Deaminases, J. Chem. Soc., Perkin Trans. 1, 1999, pp. 2929-2936.
Dymock, et al., Novel approaches to the treatment of hepatitis C virus infection, Antiviral Chemistry & Chemotherapy, 2000, pp. 79-96, vol. 11, No. 2.
Ecuador Patent Office, Opposition for EC Patent Application No. SP-13-12451, Apr. 23, 2014.
Ecuador Patent Office, Opposition for EC Patent Application No. SP-2012-11817, May 27, 2013.
Ecuador Patent Office, Statement of Opposition for EC Patent Application No. SP-10-10609, Mar. 31, 2011.
El Safadi, et al., 5-Modified-2'-dU and 2'-dC as Mutagenic Anti HIV-1 Proliferation Agents: Synthesis and Activity, Journal of Medicinal Chemistry, 2010, pp. 1534-1545, vol. 53, No. 4.
El Salvador Patent Office, Official Action for SV National Phase Entry of International Application No. PCT/US2010/049471, Nov. 6, 2013.
English translation of Office Action for MX Application No. MX/a/2013/003179, Feb. 25, 2014.
Eurasian Patent Office, Office Action for EA Patent Application No. 201390152, Apr. 14, 2014.
Eurasian Patent Office, Official Action for EA Patent Application No. 201390133, Mar. 27, 2014.
Eurasian Patent Office, Second Examination Report for EA Patent Application No. 201071128, Oct. 24, 2012.
Eurasian Patent Office, Second Examination Report for EA Patent Application No. 201071170, Oct. 25, 2012.
Eurasian Patent Office, Third Examination Report for EA Patent Application No. 201071128, Apr. 29, 2013.
Eurasian Patent Office, Third Examination Report for EA Patent Application No. 201071170, Oct. 10, 2013.
Eurasian Patent Office, Third Office Action for EA Application No. 201190110/28, Oct. 18, 2013.
European Patent Office, International Preliminary Report on Patentability and Written Opinion for PCT International Application No. PCT/US2009/041432, Oct. 26, 2010, 7 pages.
European Patent Office, International Preliminary Report on Patentability and Written Opinion for PCT International Application No. PCT/US2010/049471, Mar. 27, 2012, 7 pages.
European Patent Office, International Preliminary Report on Patentability and Written Opinion for PCT International Application No. PCT/US2010/049508, Mar. 27, 2012, 6 pages.
European Patent Office, International Preliminary Report on Patentability and Written Opinion for PCT International Application No. PCT/US2011/038253, Dec. 4, 2012, 6 pages.
European Patent Office, International Preliminary Report on Patentability and Written Opinion for PCT International Application No. PCT/US2011/044581, Jan. 22, 2013, 7 pages.
European Patent Office, International Preliminary Report on Patentability for PCT International Application No. PCT/US2009/041447, Oct. 26, 2010, 7 pages.
European Patent Office, International Preliminary Report on Patentability for PCT International Application No. PCT/US2010/023586, Aug. 16, 2011, 6 pages.
European Patent Office, International Preliminary Report on Patentability for PCT International Application No. PCT/US2011/028897, Mar. 26, 2013, 7 pages.

(56) References Cited

OTHER PUBLICATIONS

European Patent Office, International Preliminary Report on Patentability for PCT International Application No. PCT/US2011/029441, Mar. 26, 2013, 7 pages.
European Patent Office, International Preliminary Report on Patentability for PCT International Application No. PCT/US2011/045102, Jan. 22, 2013, 5 pages.
European Patent Office, International Preliminary Report on Patentability for PCT International Application No. PCT/US2015/057932, May 2, 2017, 11 pages.
European Patent Office, International Preliminary Report on Patentability for PCT International Application No. PCT/US2015/057933, May 2, 2017, 7 pages.
European Patent Office, International Preliminary Report on Patentability for PCT International Application No. PCT/US2015/057934, May 2, 2017, 14 pages.
European Patent Office, International Preliminary Report on Patentability for PCT International Application No. PCT/US2015/057934, May 11, 2017, 14 pages.
European Patent Office, International Search Report for PCT International Application No. PCT/US2011/038253, Jul. 29, 2011, 4 pages.
European Patent Office, International Search Report for PCT International Application No. PCT/US2011/044581, Nov. 7, 2011, 4 pages.
European Patent Office, International Search Report for PCT International Application No. PCT/US2009/041432, Aug. 11, 2009, 5 pages.
European Patent Office, International Search Report issued in International Application No. PCT/US2010/049471, Nov. 18, 2010, 5 pages.
European Patent Office, International Search Report issued in International Application No. PCT/US2010/049508, Nov. 5, 2010, 4 pages.
European Patent Office, International Search Report issued in International Application No. PCT/US2011/028897, Aug. 1, 2011, 6 pages.
European Patent Office, International Search Report issued in International Application No. PCT/US2011/029441, Aug. 1, 2011, 5 pages.
European Patent Office, International Search Report issued in International Application No. PCT/US2011/045102, Nov. 9, 2011, 4 pages.
European Patent Office, nternational Search Report issued in International Application No. PCT/US2009/041447, Aug. 7, 2009, 5 pages.
European Patent Office, Written Opinion and ISR for International Application No. PCT/US2015/057933, Jan. 21, 2016, 9 pages.
European Patent Office, Written Opinion and ISR for PCT International Application No. PCT/US2015/057934, May 6, 2016, 20 pages.
European Patent Office, Written Opinion and ISR for PCT International Application No. PCT/US2015/057932, May 6, 2016, 7 pages.
European Patent Office, Written Opinion for PCT International Application No. PCT/US2010/023586, Aug. 4, 2010, 5 pages.
European Patent Office, Written Opinion for PCT International Application No. PCT/US2011/028897, Aug. 1, 2011, 6 pages.
European Patent Office, Written Opinion for PCT International Application No. PCT/US2011/029441, Aug. 1, 2011, 6 pages.
European Patent Office, Written Opinion for PCT International Application No. PCT/US2011/038253, Jul. 29, 2011, 5 pages.
European Patent Office, Written Opinion for PCT International Application No. PCT/US2011/044581, Nov. 7, 2011, 6 pages.
European Patent Office, Written Opinion for PCT International Application No. PCT/US2011/045102, Nov. 9, 2011, 4 pages.
European Patent Office, Written Opinion issued in International Application No. PCT/US2009/041447, Oct. 26, 2010, 7 pages.
European Patent Office, Written Opinion issued in International Application No. PCT/US2010/049471, Mar. 27, 2012, 7 pages.
European Patent Office, Written Opinion issued in International Application No. PCT/US2010/049508, Mar. 27, 2012, 6 pages.
European Patent Office, International Search Report for PCT International Application No. PCT/US2016/052092, Oct. 11, 2016, 11 pages.
European Patent Office, Written Opinion issued in International Application No. PCT/US2011/045102, Jan. 22, 2013, 5 pages.
European Patent Office, Written Opinion issued in International Application No. PCT/US2017/028243, Aug. 29, 2017, 12 pages.
European Patent Office, International Search Report for PCT International Application No. PCT/US2018/022166, Jun. 11, 2018, 18 pages.
European Patent Office, International Search Report for PCT International Application No. PCT/US2018/022166, Jun. 11, 2018, 18 pages.
Extended European Search Report for EP Application No. 13194605.5, Mar. 13, 2014.
Farquhar, et al., Biologically Reversible Phosphate-Protective Groups, Journal of Pharmaceutical Sciences, 1983, pp. 324-325, vol. 72, No. 3.
First Examination Report (in English) for CO Patent Application No. 10-131479, Oct. 23, 2012.
First Examination Report (in English) for MX Patent Application No. MX/a/2010/011661, Oct. 26, 2011.
First Examination Report for AU Patent Application No. 2009240630, Jun. 14, 2012.
First Examination Report for AU Patent Application No. 2009240642, Aug. 2, 2012.
First Examination Report for CN Patent Application No. 200980120218.8, Nov. 13, 2012.
First Examination Report for CO Patent Application No. 10-121513-5, Dec. 10, 2012.
First Examination Report for EA Patent Application No. 201071128, Apr. 25, 2012.
First Examination Report for EA Patent Application No. 201071170, Apr. 25, 2012.
First Examination Report for ID Patent Application No. W00 2010 03923, Apr. 5, 2013.
First Examination Report for ID Patent Application No. W00 2010 03957, Apr. 25, 2013.
First Examination Report for IL Patent Application No. 208515, Jan. 6, 2013.
First Examination Report for IL Patent Application No. 208701, Jan. 13, 2013.
First Examination Report for JP Patent Application No. 2011-506429, Aug. 22, 2013.
First Examination Report for JP Patent Application No. 2011-506435, Aug. 22, 2013.
First Examination Report for NZ Patent Application No. 588400, Apr. 11, 2011.
First Examination Report for NZ Patent Application No. 588670, Apr. 8, 2011.
First Examination Report for NZ Patent Application No. 608070, Nov. 7, 2013.
First Examination Report for TW Patent Application No. 098113324, Oct. 30, 2012.
First Examination Report for UA Patent Application No. 2010 13030, Mar. 2, 2013.
First Examination Report for VN Patent Application No. 1-2010-02653, Apr. 26, 2012.
First Examination Report for VN Patent Application No. 1-2010-02939, Apr. 19, 2012.
First Office Action for CL Patent Application No. 1906-2011, received May 7, 2013.
First Office Action for CN Patent Application No. 201080011960.0, Jun. 8, 2013.
First Office Action for EA Patent Application No. 201190110/28, Apr. 26, 2012.
First Office Action for EA Patent Application No. 201390141/28, with English translation, received Aug. 14, 2014.
First Office Action for EP Patent Application No. 10704068.5, Jun. 18, 2012.

(56) References Cited

OTHER PUBLICATIONS

First Office Action for IL Patent Application No. 214396, Jul. 8, 2013.
First Office Action for UA Application No. A 2011 10568, received Apr. 7, 2014.
First Office Action for VN Patent Application No. 1-2012-03895, Feb. 8, 2013.
First Office Action for EP Patent Application No. 10704068.5, dated Jun. 18, 2012.
First Office Action for IL Patent Application No. 214396, dated Jul. 8, 2013.
First Office Action for VN Patent Application No. 1-2012-03895, dated Feb. 8, 2013.
Form 21 for AP Patent Application No. AP/P/2011/005818, Sep. 19, 2013.
Fukumoto, et al., Viral Dynamics of Hepatiis C Early After Orthotopic Liver Transplantation: Evidence for Rapid Turnover of Serum Virions, Hepatology, 1996, pp. 1351-1354, vol. 24.
Further Examination Report for NZ Application No. 594370, Oct. 8, 2013.
Garcia, et al., Synthesis of (2,3,4,6-tetra-O-acetyl-alpha-D-glycopyranosyl)thiophene derivatives as new C-nucleoside analogues, J. Carbohydrate Chemistry, 2001, pp. 681-687, vol. 20, No. 7/8.
Gardelli, et al., Phosphoramidate Prodrugs of 2'-C-Methylcytidine for Therapy of Hepatitis C Virus Infection, Journal of Medicinal Chemistry, 2009, pp. 5394-5407, vol. 52, No. 17.
Gleeson, et al., Prediction of the Potency of Inhibitors of Adenosine Deaminase by QM/MM Calculations, Chem. Commun., 2003, pp. 2180-2181.
Gordon, et al., Control of Hepatitis C: A Medicinal Chemistry Perspective, J. Med. Chem., 2005, pp. 1-20, vol. 48, No. 1.
Greene, Protective Groups in Organic Synthesis, 1991, 15 pages, John Wiley & Sons, New York.
Gudmundsson, et al., Synthesis of imidazo[1,2-a]pyridine C-Nucleosides with an Unexpected Site of Ribosylation, Journal of Organic Chemistry, 1997, pp. 3453-3459, vol. 62.
Gudmundsson, et al., The Condensation of 2,6-dichloroimidazo[1,2-a]pyridine C-nucleoside with an Unexpected Site of Ribosylation, Tetrahedron Letters, 1996, pp. 2365-2368, vol. 7, No. 14.
Gunic, et al., Cyclic monophosphate prodrugs of base-modified 2'-C-methyl ribonucleosides as potent inhibitors of hepatitis C virus RNA replication, Bioorganic & Medicinal Chemistry Letters, 2007, pp. 2452-2455, vol. 17.
Hamann, et al., Synthesis and antiviral evaluation of 7,9-dideaza-8-thiapurine C-nucleoside derivatives, Collection Symposium Series, 2008, pp. 347-349, vol. 10.
Hamann, et al., Synthesis and antiviral evaluation of thieno[3,4-d]pyrimidine C-nucleoside analogues of 2',3'-dideoxy- and 2',3'-dideoxy-2',3'-didehydro-adenosine and -inosine, Bioorganic & Medicinal Chemistry, 2009, pp. 2321-2326, vol. 17.
Han, et al., Synthesis of 1-Chloroacetyl-1-dehydroxy-2,3,5-tri-O-benzoyl-β-D-ribofuranose. A Potentially Versatile Intermediate for the Synthesis of C-Nucleosides, Synthetic Communications, 1992, pp. 2815-2822, vol. 22, No. 19.
Haraguchi, et al., Stereoselective Synthesis of 1'-C-Branched Uracil Nucleosides From Uridine, Nucleosides & Nucleotides, 1995, pp. 417-420, vol. 14, No. 3-5.
Harki, et al., Synthesis and Antiviral Activity of 5-Substituted Cytidine Analogues: Identification of Potent.Inhibitor of Viral RNA-Dependent RNA Polymerases, Journal of Medicinal Chemistry, 2006, pp. 6166-6169, vol. 49, No. 21.
Hayashi, et al., C-Nucleosides. 17. A Synthesis of 2-Substituted 7-(B-D-Ribofuranosyl)-Pyrrolo[2,14]-1,2,4-Triazines. A New Type of "Purine Like" C-Nucleoside, Heterocycles, 1992, pp. 569-574, vol. 34, No. 3.
Hecker, et al., Liver Targeted Prodrugs of 2'-C-Methyladenosine for Therapy of Hepatitis C Virus Infection, J. Med. Chem., 2007, pp. 3891-3896, vol. 50, No. 16.
Hoffman, et al., When, in the Context of Drug Design, Can a Fluorine Atom Successfully Substitute a Hydroxyl Group?, International Journal of Quantum Chemistry, 2002, pp. 419-427, vol. 89.
Indonesia Patent Office, Substantive Examination Report Stage 1 for ID Application No. W-00201103126, Jun. 10, 2014.
Israel Patent Office, Notification of Defects for IL Patent Application No. 208515, Aug. 25, 2014.
Israel Patent Office, Notification of Defects for IL Patent Application No. 214396, Nov. 11, 2013.
Israel Patent Office, Notification of Defects for IL Patent Application No. 218599, Aug. 25, 2014.
Israel Patent Office, Notification of Defects for IL Patent Applicaton No. 208701, Aug. 25, 2014.
Israel Patent Office, Notification Prior to Examination for IL Patent Application No. 218599, Nov. 13, 2012.
Israel Patent Office, Notification Prior to Examination for IL Patent Application No. 218752, Jan. 20, 2014.
Israel Patent Office, Supplement to First Examination Report for IL Patent Application No. 208515, Jan. 15, 2013.
Itoh, et al., Divergent and Stereocontrolled Approach to the Synthesis of Uracil Nucleosides Branched at the Anomeric Position, J. Org. Chem., 1995, pp. 656-662, vol. 60, No. 3.
Japanese Patent Office, Notice of Reasons for Rejection for JP Application No. 2011-549324, Jul. 28, 2014.
Japanese Patent Office, Notice of Reasons for Rejection for JP Application No. 2011-549324, Mar. 26, 2014.
Japanese Patent Office, Notification of Reasons for Rejection for JP Patent Application No. 2012-529958, Aug. 5, 2014.
Japanese Patent Office, Notification of Reasons for Rejection for JP Patent Application No. 2012-529963, Aug. 28, 2014.
Jasko, et al., 5'-Phosphonates of Ribonucleosides and 2'-Deoxyribonucleosides: Synthesis and Antiviral Activity, Nucleosides & Nucleotides, 1993, pp. 879-893, vol. 12, No. 8.
Kabat, et al., Nucleosides, CXLVIII, Synthesis of 6-(β-D-Ribofuranosyhpicolinamide: A Novel C-Nucleoside from D-Ribonolactone, Chemical & Pharmaceutical Bulletin, 1988, pp. 634-640, vol. 36, No. 2.
Kim, et al., Reversal of the Progression of Fatal Coronavirus Infection in Cats by a Broad-Spectrum Coronavirus Protease Inhibitor, PLOS Pathogens, Mar. 30, 2016, p. e1005531, vol. 12, No. 3.
Khamnei, et al., Neighboring Group Catalysis in the Design of Nucleotide Prodrugs, J. Med. Chem., 1996, pp. 4109-4115, vol. 39, No. 20.
Klumpp, et al., The Novel Nucleoside Analog R1479 (4'-Azidocytidine) is a Potent Inhibitor of NS5B-dependent RNA Synthesis and Hepatitis C virus Replication in Cell Culture, Journal of Biological Chemistry, 2006, pp. 3793-3799, vol. 281, No. 7.
Knutsen, et al., Synthesis of Imidazo-fused Bridgehead-nitrogen 2'-Deoxyribo-C-nucleosides: Coupling-Elimination Reactions of 2,5-Anhydro-3,4,6-tri-O-benzoyl-o-allonic Acid, J. Chem. Soc., Perkin Trans. 1, 1985, pp. 621-630.
Knutsen, et al., Synthesis of Imidazo-fused Bridgehead-nitrogen C-Nucleosides via Dehydrative Coupling Reactions of 2,5-Anhydro-3,4,6-tri-O-benzoyl-D-allonic Acid, J. Chem. Soc., Perkin Trans 1, 1984, pp. 229-238.
Kobe, et al., Use of Distance Geometry Approach for the In Vitro Antiviral Activity Evaluation of N-bridgehead C-nucleosides, European J. Med. Chem., 1992, pp. 259-266, vol. 27, No. 3.
Lefebvre, et al., Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate, Journal of Medicinal Chemistry, 1995, pp. 3941-3950, vol. 38, No. 20.
Lefebvre, et al., Synthesis, Decomposition Pathways and 'In Vitro' Evaluation of Bioreversible Phosphotriesters of Azt, Nucleosides, Nucleotides & Nucleic Acids, 1995, pp. 763-766, vol. 14, No. 3-5.
Lindell, et al., Synthesis and Biochemical Testing of 3-(Carboxyphenylethyl)imidazo[2,1-f][1,2,4]triazines as Inhibitors of AMP Deaminase, ACS Medicinal Chemistry Letters, 2010, pp. 286-289, vol. 1, No. 6.

(56) References Cited

OTHER PUBLICATIONS

Lovelette, 1,2,4-Triazines. Synthesis of selected members of the s-triazolo[3,4-f][1,2,4]triazine and tetrazolo[1,5-f][1,2,4]triazine ring systems, Journal of Heterocyclic Chemistry, 1979, pp. 555-560, vol. 16.

Martell, et al., Hepatitis C Virus (HCV) Circulates as a Population of Different but Closely Related.Genomes: Quasispecies Nature of HCV Genome Distribution, Journal of Virology, 1992, pp. 3225-3229, vol. 6695.

Mason, et al., Polyadenylation-dependent screening assay for respiratory syncytial virus RNA transcriptase activity and identification of an inhibitor, Nucleic Acids Research, 2004, pp. 4758-4767, vol. 32, No. 16.

Matulic-Adamic, et al., Synthesis of 3-(β-D-Ribofuranosyl)-2-Fluoropyridine and 3-(β-D-Ribofuranosyl)-Pyridin-2-one, Tetrahedron Letters, 1997, pp. 203-206, vol. 38, No. 2.

Matulic-Adamic, et al., Synthesis of 5-(β-D-Ribofuranosyl)-Pyridin-2-one: a 'Deletion-Modified' Analogue of Uridine, Tetrahedron Letters, 1997, pp. 1669-1672, vol. 38, No. 10.

McGuigan, et al., Intracellular Delivery of Bioactive AZT Nucleotides by Aryl Phosphate Derivatives of AZT, J. Med. Chem., 1993, pp. 1048-1052, vol. 36, No. 8.

Meppen, et al., Cyclic phosphoramidates as prodrugs of 2'-C-methylcytidine, European Journal of Medicinal Chemistry, 2009, pp. 3765-3770, vol. 49, No. 9.

Metobo, et al., Practical synthesis of 10-substituted Tubercidin C-nucleoside analogs, Tetrahedron Letters, 2011, pp. 484-486, vol. 53.

Mexico Patent Office, Office Action for MX Application No. MX/a/2011/008409, Mar. 25, 2014.

Mexico Patent Office, Office Action for MX Application No. MX/a/2013/000656, Apr. 22, 2014.

Mexico Patent Office, Office Action for MX Application No. MX/a/2013/000656, Aug. 4, 2014.

Mexico Patent Office, Office Action for MX Application No. MX/a/2013/000744, Apr. 22, 2014.

Migliaccio, et al., Characterization of Resistance to Non-obligate Chain-terminating Ribonucleoside Analogs That Inhibit Hepatitis C Virus Replication in vitro, The Journal of Biological Chemistry, 2003, pp. 49164-49170, vol. 278, No. 49.

Mitchell, et al., Bioreversible Protection for the Phospho Group: Bioactivation of the Di(4-acyloxybenzyl) and Mono(4-acyloxybenzyl) Phosphoesters of Methylphosphonate and Phosphonoacetate, J. Chem. Soc., Perkin Trans. 1, 1992, pp. 2345-2353.

Mitchell, et al., Synthesis of C-Nucleoside Isosteres of 9-(2-Hydroxyethoxymethyl)guanine (Acyclovir), J. Het. Chem., 1984, pp. 697-699, vol. 21, No. 3.

Moennig, et al., The Pestiviruses, Advances in Virus Research, 1992, pp. 53-98, vol. 41.

Moradpour, et al., Replication of hepatitis C virus, Nature Reviews Microbiology, 2007, pp. 453-463, vol. 5, No. 6.

Moscow, et al., Reduced Folate Carrier Gene (RFC1) Expression and Anti-Folate Resistance in Transfected and Non-Selected Cell Lines, International Journal of Cancer, 1997, pp. 184-190, vol. 72.

Murakami, et al., Mechanism of Activation of Beta-D-2'-Fluoro-2'-C-Methylcytidine and Inhibition of Hepatitis C Virus NS5b RNA Polymerase, Antimicrob Agents Chemother., Feb. 2007, pp. 503-509, vol. 51, No. 2.

Murphy, et al., The nucleoside analog GS-441524 strongly inhibits feline infections peritonitis (FIP) virus in tissue culture and experimental cat infection studies, Veterinary Microbiology, ND, pp. 226-233, vol. 219, 2018.

Neumann, et al., Hepatitis C Viral Dynamics in Vivo and the Antiviral Efficacy of Interferon-α Therapy, Science, 1998, pp. 103-107, vol. 282.

New Zealand Patent Office, Second Examination Report and Notice of Acceptance for NZ Patent Application No. 588400, Jul. 27, 2012.

Nishimura, et al., Synthesis of pyrrolo[2,1-f ][1,2,4]triazine C-nucleosides, Isosteres of sangivamycin, tubercidin, and toyocamycin, Carbohydrate Research, 2001, pp. 77-82, vol. 331, No. 1.

Ogura, et al., Reaction of Ethynyl Compounds with Lactones, Journal of Organic Chemistry, 1972, pp. 72-75, vol. 37, No. 1.

Otter, et al., Conformational Properties of Purine-Like C-Nucleosides, Nucleosides & Nucleotides, 1996, pp. 793-807, vol. 15, No. 1-3.

Pankiewicz, et al., C-Nucleoside Analogues of Nicotinamide Mononucleotide (NMN), Nucleosides and Nucleotides, 1988, pp. 589-593, vol. 7, No. 5&6.

Pankiewicz, et al., Efficient Synthesis of 5-(β-D-Ribofuranosyhnicotinamide and its α-Isomer, Journal of Organic Chemistry, 1988, pp. 3473-3479, vol. 53.

Patil, et al., C-Glycosylation of Substituted Heterocycles under Friedel-Crafts Conditions (II): Robosylation of Multi-Functionalized Thiophenes and Furans for the Synthesis of Purine-Like C-Nucleosides, Nucleosides & Nucleotides, 1990, pp. 937-956, vol. 9, No. 7.

Patil, et al., 4-Aza-7,9-Dideazaadenosine, A New Cytotoxic Synthetic C-Nucleoside Analogue f Adenosine, Tet. Lett., 1994, pp. 5339-5342, vol. 35.

Patil, et al., Synthesis of Pyrrolo[2,1-f][1,2,4]triazine Congeners of Nucleic Acid Purines via the N-Amination of 2-Substituted Pyrroles, J. Het. Chem., 1994, pp. 781-786, vol. 31.

Patil, et al., Synthesis of some new thieno[3,4-d]pyrimidines and their C-nucleosides, Journal of Heterocyclic Chemistry, 1993, pp. 509-515, vol. 30, No. 2.

Perrone, et al., Application of the Phosphoramidate ProTide Approach to 4'-Azidouridine Confers Sub-micromolar Potency versus Hepatitis C Virus on an Inactive Nucleoside, Journal of Medicinal Chemistry, 2007, pp. 1840-1849, vol. 50, No. 8.

Peru Patent Office, Office Action in PE Application No. 1464, Sep. 12, 2013.

Piccirilli, et al., A Direct Route to 3-(D-Ribofuranosyl)pyridine Nucleosides, Helvetica Chimica Acta, 1991, pp. 397-406, vol. 74.

Pierra, et al., Synthesis and Pharmacokinetics of Valopicitabine (NM283), and Efficient Prodrug of the Potent Anti-HCV Agent 2'-C-Methylcytidine, Journal of Medicinal Chemistry, 2006, pp. 6614-6620, vol. 49, No. 22.

Poduch, et al., Design of Inhibitors of Orotidine Monophosphate Decarboxylase Using Bioisosteric Replacement and Determination of Inhibition Kinetics, Journal of Medicinal Chemistry, 2006, pp. 4937-4945, vol. 49, No. 16.

Puech, et al., Intracellular Delivery of Nucleoside Monophosphates through a Reductase-mediated Activation Process, Antiviral Research, 1993, pp. 155-174, vol. 22, No. 4.

Ramasamy, et al., Synthesis and Antitumor Activity of Certain 3-B-D-Ribofuranosyl-1,2,4-triazolo[3,44]-1,2,4-triazines Related to Formycin Prepared via Ring Closure of a 1,2,4-Triazine Precursor, J. Med. Chem., 1986, pp. 2231-2235, vol. 29, No. 11.

Rao, et al., C-Glycosylation of Substituted Heterocycles under Friedel-Crafts Conditions (I): A Two-Step Synthesis of the Thieno[3,4-d]Pyrimidine C-Nucleoside Analog of Inosine, Tetrahedron Letters, 1988, pp. 3537-3540, vol. 29, No. 29.

Reddy, et al., Stereoselective Synthesis of Nucleoside Monophosphate HepDirectTM Prodrugs, Tet. Lett., 2005, pp. 4321-4324, vol. 46.

Schul, et al., A Dengue Fever Viremia Model in Mice Shows Reduction in Viral Replication and Suppression.Of the Inflammatory Response after Treatment with Antiviral Drugs, Journal of Infectious Diseases, 2007, pp. 665-674, vol. 195.

Schultz, Prodrugs of Biologically Active Phosphate Esters, Bioorganic & Medicinal Chemistry, 2003, pp. 885-898, vol. 11.

Scott, et al., Interferon-a-2b Plus Ribavirin: A Review of its Use in the Management of Chronic Hepatitis C, Drugs, 2002, pp. 507-556, vol. 62, No. 3.

Shekunov, et al., Crystallization processes in pharmaceutical technology and drug delivery design, Journal of Crystal Growth, 2000, pp. 122-136, vol. 211.

Silverman et al., The Organic Chemistry of Drug Design and Drug Action, 1992, pp. 19-23.

Silverman, The Organic Chemistry of Drug Design and Drug Action, 2nd Ed., 2004, pp. 29-34.

(56) References Cited

OTHER PUBLICATIONS

Srivastav, et al., Antiviral Activity of Various 1-(2'-Deoxy-β-D-Iyxofuranosyl), 1-(2'-Fluoro-β-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication, Journal of Medicinal Chemistry, 2010, pp. 7156-7166, vol. 53, No. 19.
Taiwan Patent Office, Office Action with Search Report for TW Patent Application No. 099131868, May 22, 2014.
Taiwan Patent Office, Office Action with Search Report for TW Patent Application No. 102115415, May 15, 2014.
Tapia, et al., Combination of a Mutagenic Agent with a Reverse Transcriptase Inhibitor Results n Systematic Inhibition of HIV-1 Infection, Virology, 2005, pp. 1-8, vol. 338.
Uchiyama, et al., O-selective Phosphorylation of Nucleosides without N-protection, J. Org. Chem., Jan. 1, 1993, vol. 58, No. 2.
Ukraine Patent Office, Second Office Action for UA Patent Application No. 2011 10568, Aug. 11, 2014.
United States Patent and Trademark Office, Final Rejection for U.S. Appl. No. 12/886,248, dated Aug. 21, 2014.
United States Patent and Trademark Office, Notice of Allowance for U.S. Appl. No. 13/649,511, dated Feb. 13, 2014.
United States Patent and Trademark Office, Notice of Allowance for U.S. Appl. No. 13/649,511, dated Jun. 3, 2014.
United States Patent and Trademark Office, Notice of Allowance for U.S. Appl. No. 12/428,176, dated Apr. 12, 2011.
United States Patent and Trademark Office, Notice of Allowance for U.S. Appl. No. 12/428,176, dated Jan. 6, 2011.
United States Patent and Trademark Office, Notice of Allowance for U.S. Appl. No. 12/428,234, dated Apr. 7, 2011.
United States Patent and Trademark Office, Notice of Allowance for U.S. Appl. No. 12/702,957, dated Apr. 26, 2011.
United States Patent and Trademark Office, Notice of Allowance for U.S. Appl. No. 12/885,917, dated Feb. 17, 2011.
United States Patent and Trademark Office, Notice of Allowance for U.S. Appl. No. 13/050,820, dated Jan. 31, 2013.
United States Patent and Trademark Office, Notice of Allowance for U.S. Appl. No. 13/117,060, dated Aug. 10, 2012.
United States Patent and Trademark Office, Notice of Allowance for U.S. Appl. No. 13/117,060, dated Nov. 28, 2012.
United States Patent and Trademark Office, Notice of Allowance for U.S. Appl. No. 13/196,117, dated Jul. 16, 2012.
United States Patent and Trademark Office, Notice of Allowance for U.S. Appl. No. 13/196,117, dated Mar. 27, 2012.
United States Patent and Trademark Office, Office Action (Restriction Requirement) for U.S. Appl. No. 12/886,248, dated Sep. 14, 2012.
United States Patent and Trademark Office, Office Action for U.S. Appl. No. 14/613,719, dated Jul. 21, 2016.
United States Patent and Trademark Office, Office Action for U.S. Appl. No. 14/613,719, dated Nov. 4, 2016.
United States Patent and Trademark Office, Office Action for U.S. Appl. No. 12/428,234, dated Dec. 23, 2010.
United States Patent and Trademark Office, Office Action for U.S. Appl. No. 12/702,957, dated Dec. 23, 2010.
United States Patent and Trademark Office, Office Action for U.S. Appl. No. 12/886,248, dated Mar. 4, 2013.
United States Patent and Trademark Office, Office Action for U.S. Appl. No. 12/886,248, dated Nov. 6, 2012.
United States Patent and Trademark Office, Office Action for U.S. Appl. No. 13/050,820, dated Mar. 27, 2012.
United States Patent and Trademark Office, Office Action for U.S. Appl. No. 13/050,820, dated Oct. 16, 2012.
United States Patent and Trademark Office, Office Action for U.S. Appl. No. 13/196,117 dated Sep. 23, 2011.
United States Patent and Trademark Office, Office Action for U.S. Appl. No. 13/649,511, dated Aug. 15, 2013.
United States Patent and Trademark Office, Office Action for U.S. Appl. No. 13/649,511, dated Jan. 22, 2013.
United States Patent and Trademark Office, Office Action for U.S. Appl. No. 15/813,886, dated Sep. 24, 2014.
United States Patent and Trademark Office, Pre-Appeal Brief for U.S. Appl. No. 14/613,719, dated Feb. 6, 2017.
Vaghefi, et al., Synthesis and Antiviral Activity of Certain Nucleoside 5'-Phosphonoformate Derivatives, Journal of Medicinal Chemistry, 1986, pp. 1389-1393, vol. 29, No. 8.
Vietnam Patent Office, Second Examination Report for VN Patent Application No. 1-2010-02939, Jul. 26, 2012.
Warren, et al., Therapeutic efficacy of the small molecule GS-5734 against Ebola virus in rhesus monkeys, Nature, 2016, pp. 381-385, vol. 531.
Wu, et al., Synthetic Methodologies for C-Nucleosides, Synthesis, 2004, pp. 1533-1553, vol. 10.
Yamanaka, et al., Metabolic Studies on BMS-200475, a New Antiviral Compound Active against Hepatitis B Virus, Antimicrobial Agents and Chemotherapy, 1999, p. 190, vol. 43, No. 1.
Yoshimura, et al., Synthesis and Biological Evaluation of 1'-C-Cyano-Pyrimidine Nucleosides, Nucleosides & Nucleotides, 1996, pp. 305-324, vol. 15, No. 1-3.
Zhang, et al., A Practical Synthesis of (2R)-3,5-di-O-benzoyl-2-fluoro-2-C-methyl-D-ribono-y-lactone, Tetrahedron: Asymmetry, 2009, pp. 305-312, vol. 20.
Barl, et al., The halogen/magnesium-exchange using iPrMgCl•LiCl and related exchange reagents, Heterocycles, Jan. 2014, pp. 827-844, vol. 88, No. 2.
Bullard-Feibelman, et al., The FDA-approved drug Sofosbuvir inhibits Zika Virus infection, Antiviral Res., Jan. 1, 2018, pp. 134-140, vol. 137.
Cho, et al., Discovery of the First C-Nucleoside HCV Polymerase Inhibitor (GS-6620) with Demonstrated Antiviral Response in HCV Infected Patients, J. Med. Chem., 2014, pp. 1812-1825, vol. 57, No. 5.
Dai, et al., Synthesis of 2'-C-β-Fluoromethyluridine, Organic Letters, 2003, pp. 807-810, vol. 5, No. 6.
De Clercq, Antiviral Drugs: Current State of the Art, J. Clin. Virol., 2001, pp. 73-89, vol. 22, No. 1.
Lu, Chengping, Veterinary Microbiology 5th edition, Jan. 31, 2013, p. 431, China Agriculure Press (No English Translation available).
McGuigan,et al. Application of Phosphoramidate ProTide Technology Significantly Improves Antiviral Potency of Carbocyclic Adenosine Derivatives, 2006, pp. 7215-7226.
Meppen, et al., Medi-404—A Prodrug Approach for the Treatment of HCV Infection, Abstracts of papers, 236th ACS National Meeting, Philadelphia, PA, United States, Aug. 17-21, 2008.
Porter, et al., Zika virus, drug discovery, and student projects, ScienceBlogs, Mar. 9, 2016, 7 pages.
Sacramento, et al., The clinically approved antiviral drug Sofosbuvir inhibits Zika Virus replication, Nature, Jan. 18, 2017.
Venkatachalam, et al. Effect of change in nucleoside structure on the activation and antiviral activity of phosphoramidate derivatives, 2005, pp. 5408-5423.
European Patent Office, International Search Report for PCT International Application No. PCT/US2018/029974, Sep. 18, 2018, 21 pages.
Caira, et al., Crystalline Polymorphism of Organic Compounds, Topics in Current Chemistry, Jan. 1998, pp. 163-208, vol. 198.
Siegel, et al., Discovery and Synthesis of a Phosphoramidate Prodrug of a Pyrrolo[2,1-f][triazin-4-amino] Adenine C-Nucleoside (GS-5734) for the Treatment of Ebola and Emerging Viruses, Journal of Medicinal Chemistry, Feb. 14, 2017, pp. 1648-1661, vol. 60, No. 5.
Brittain, Polymorphism in Pharmaceutical Solids, $2^{nd}$ Edition, 2009, pp. 183-226, Informa Healthcare USA, Inc.

\* cited by examiner

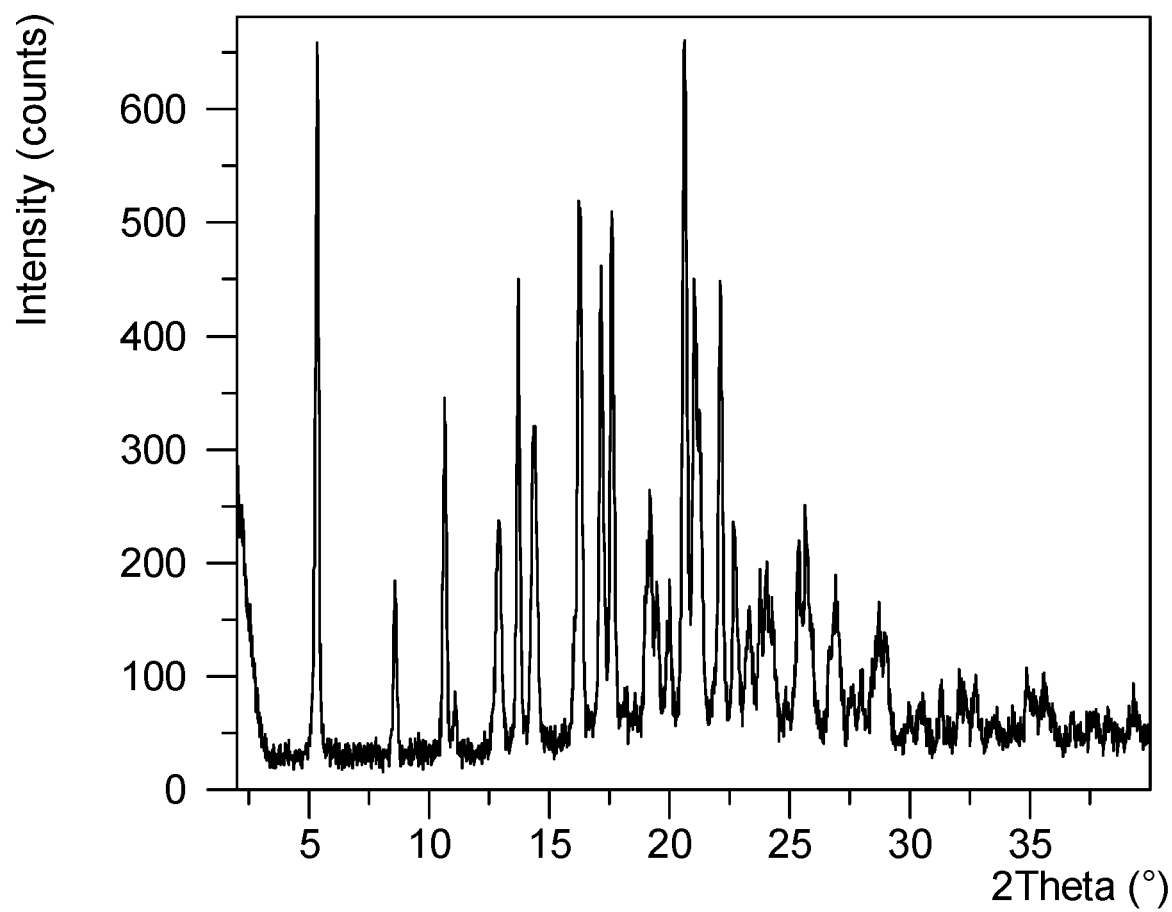
FIG. 1: XRPD pattern for Formula I Form I

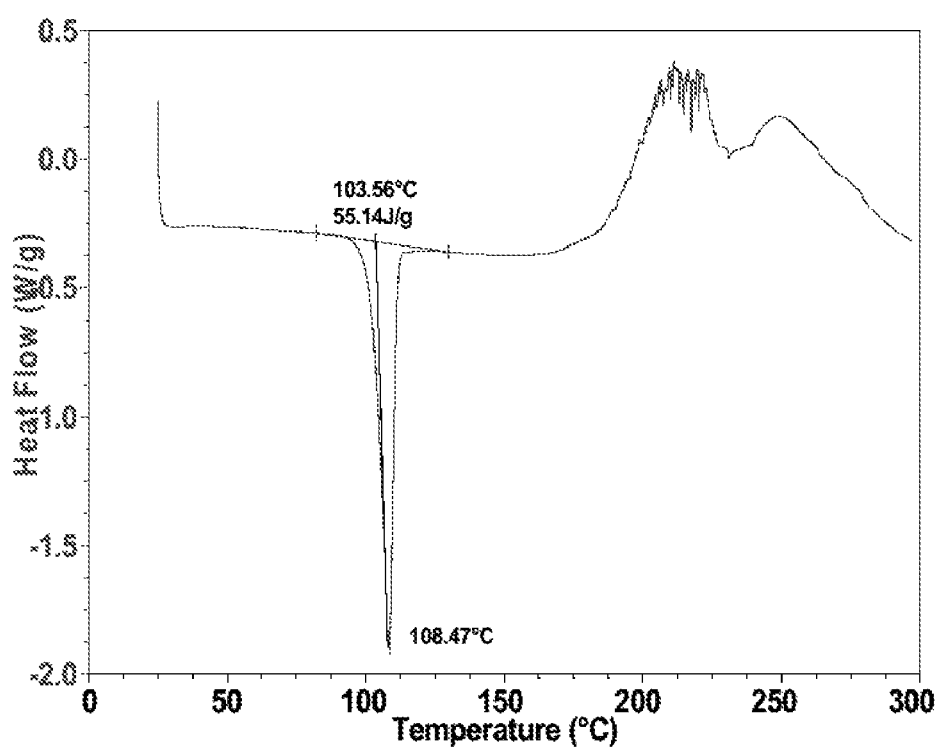
FIG. 2: DSC for Formula I Form I

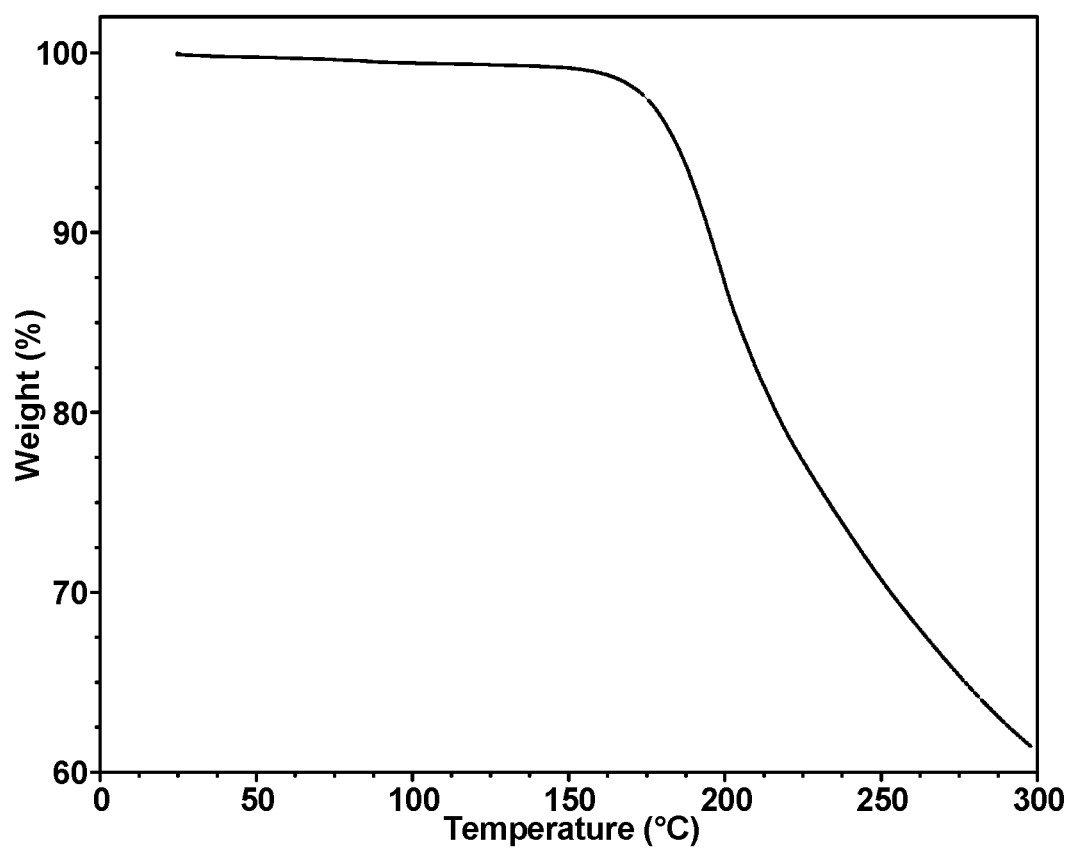
FIG. 3: TGA for Formula I Form I

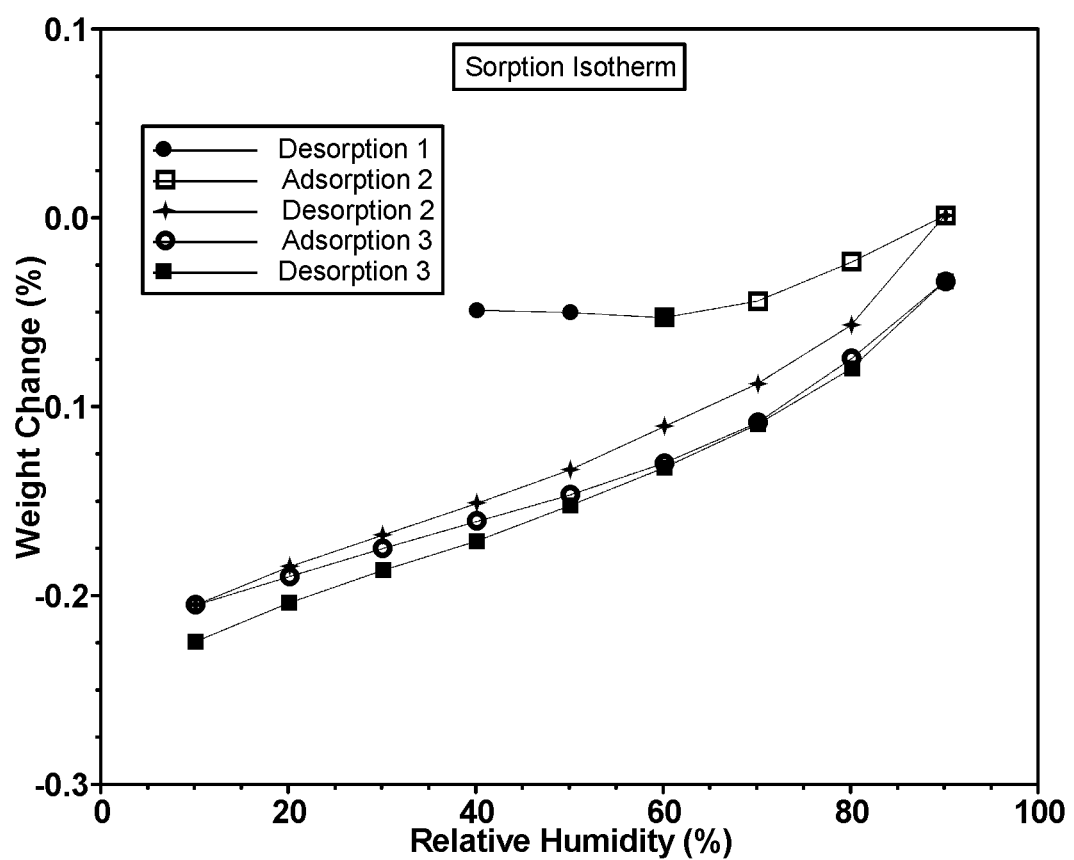
FIG. 4: DVS for Formula I Form I

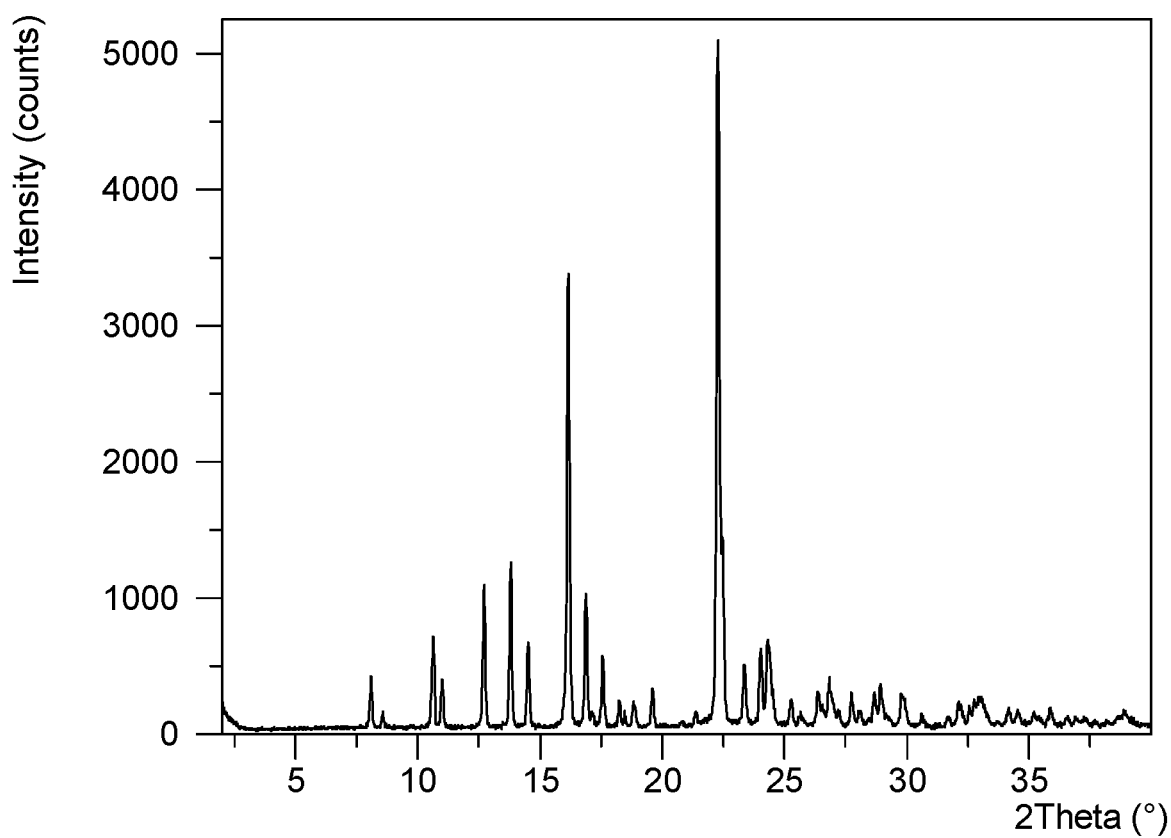
FIG. 5: XRPD pattern for Formula I Form II

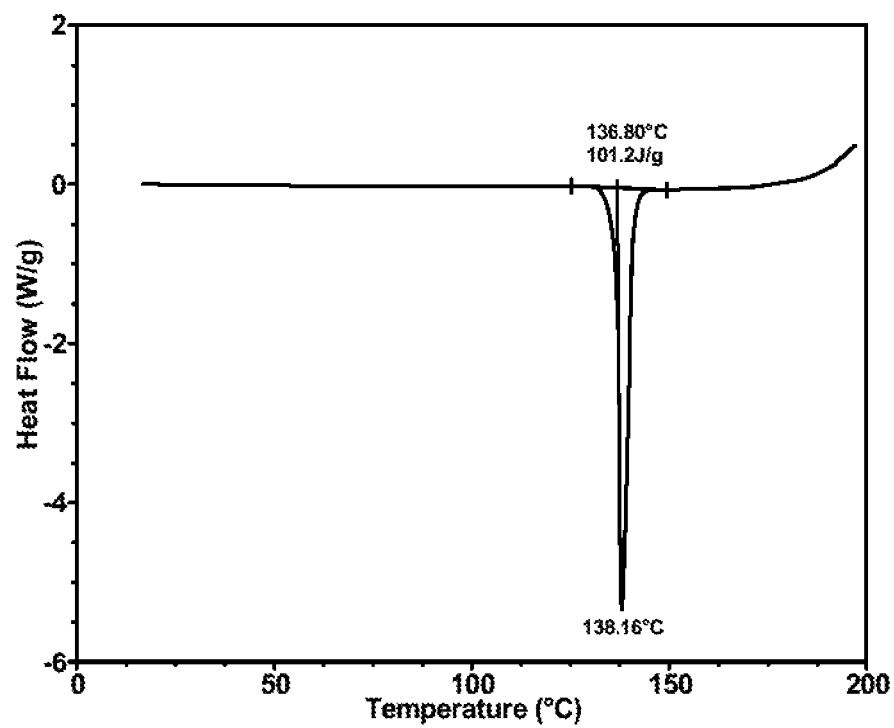
FIG. 6: DSC for Formula I Form II

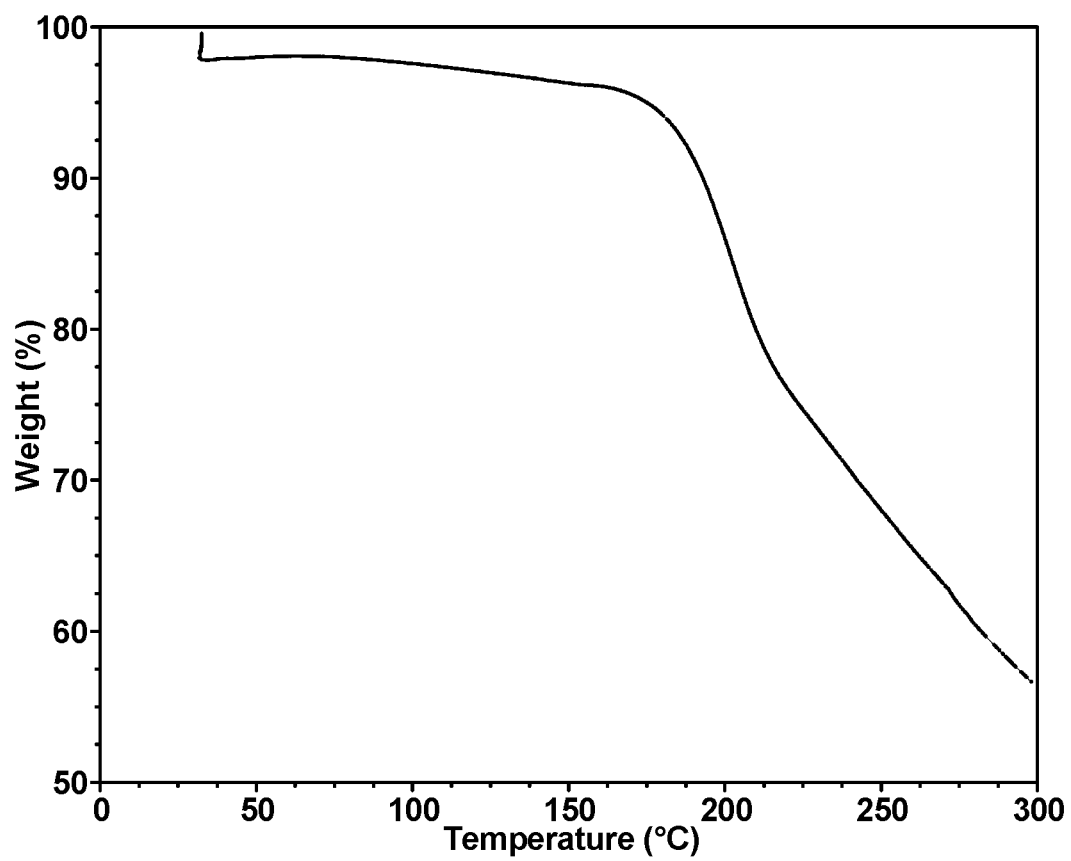
FIG. 7: TGA for Formula I Form II

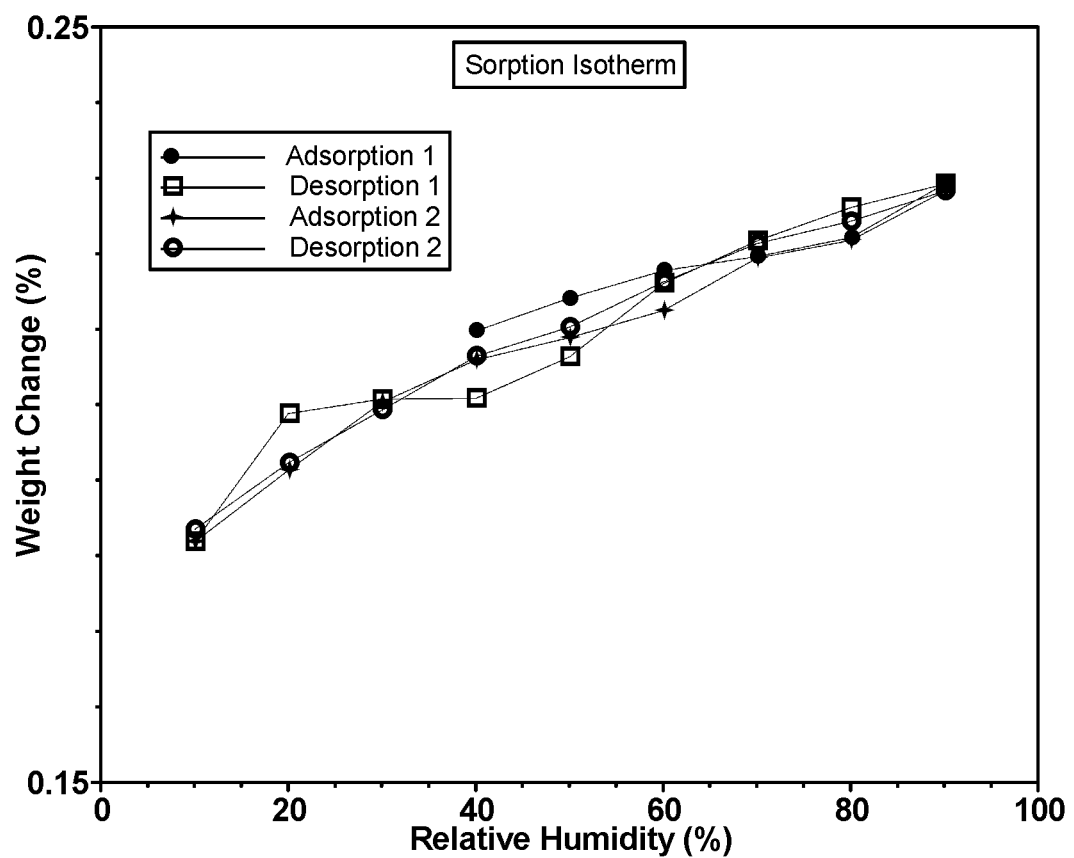
FIG. 8: DVS for Formula I Form II

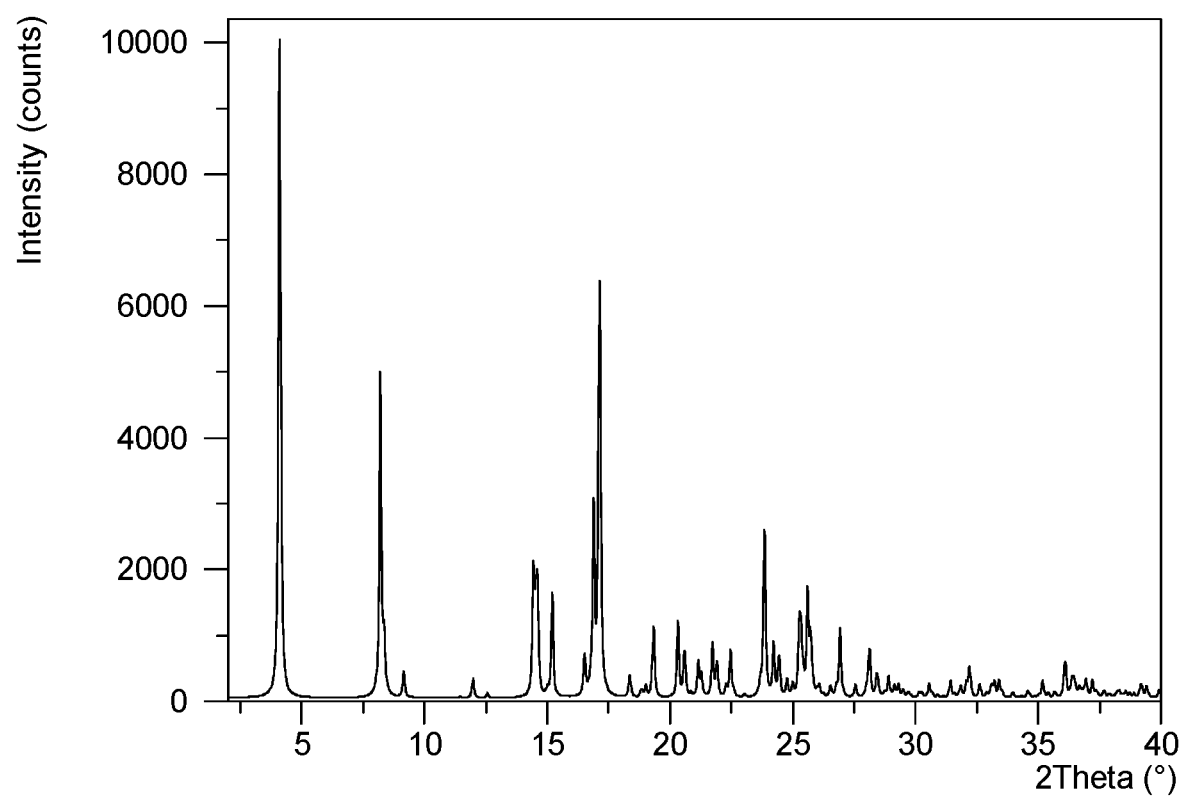
FIG. 9: Calculated XRPD pattern for Formula I Form III

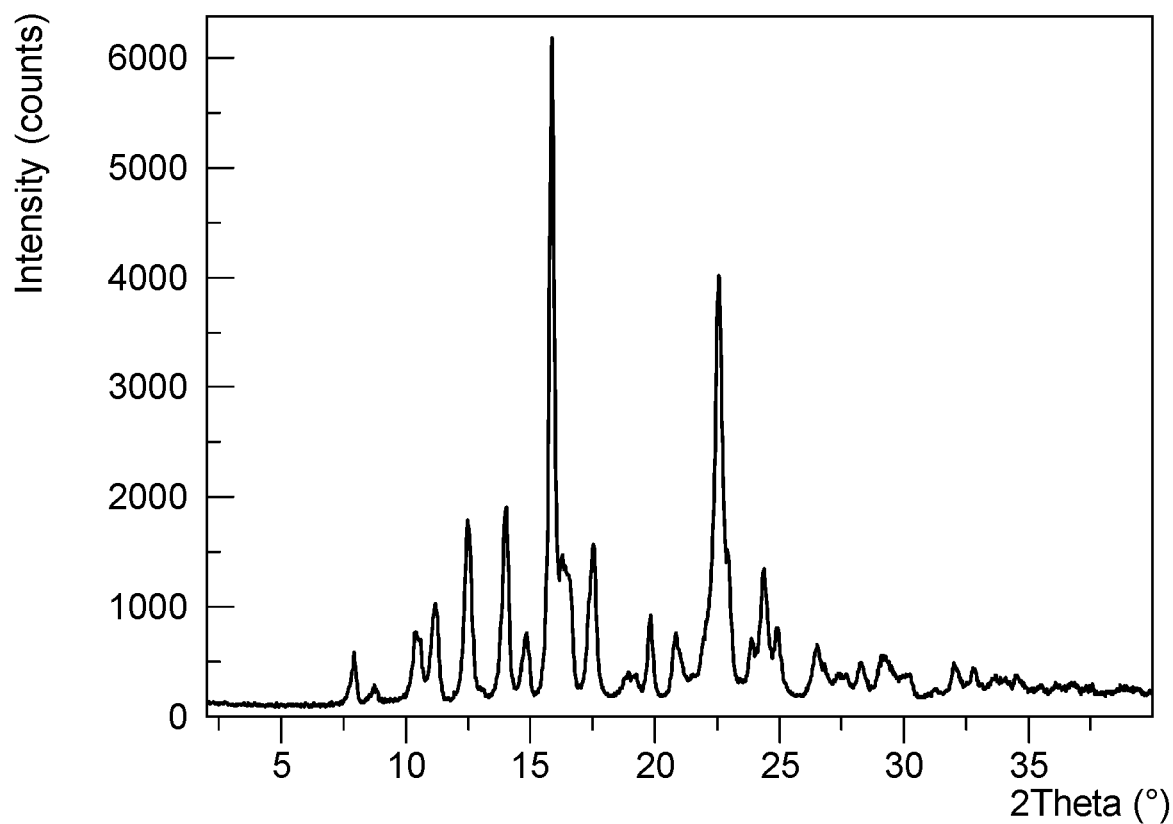
FIG. 10: XRPD pattern for Formula I Form IV

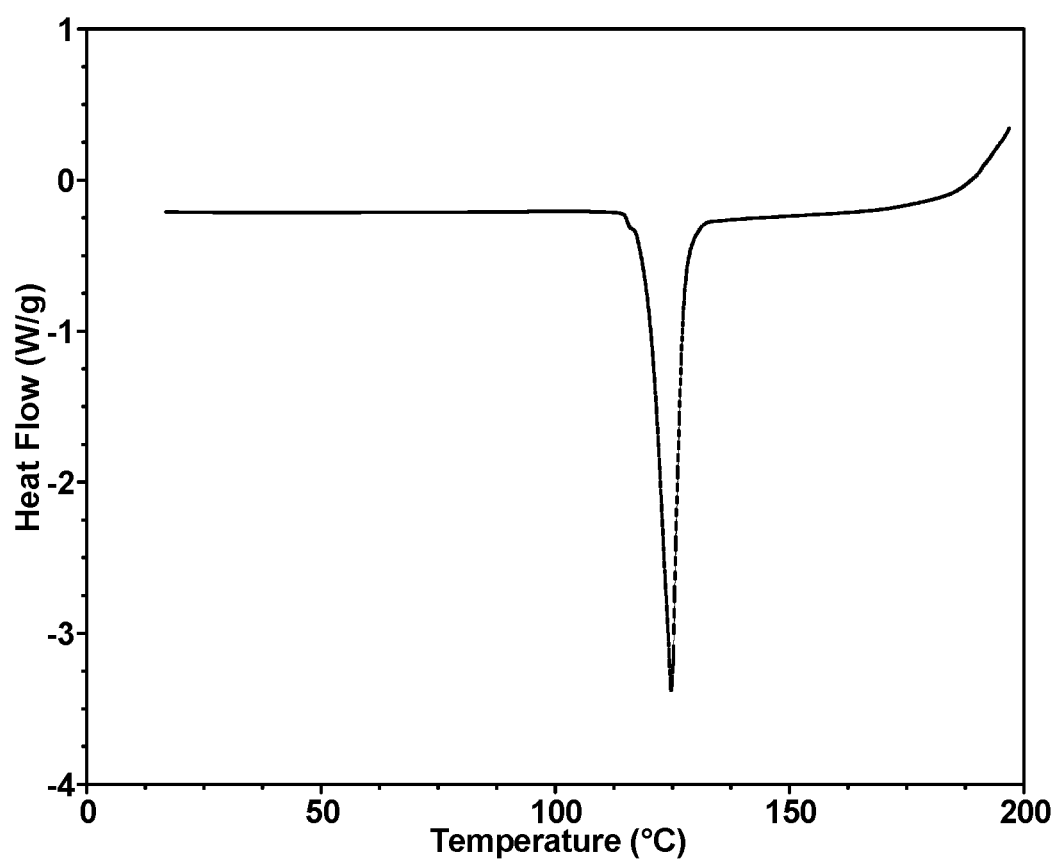
FIG. 11: DSC for Formula I Form IV

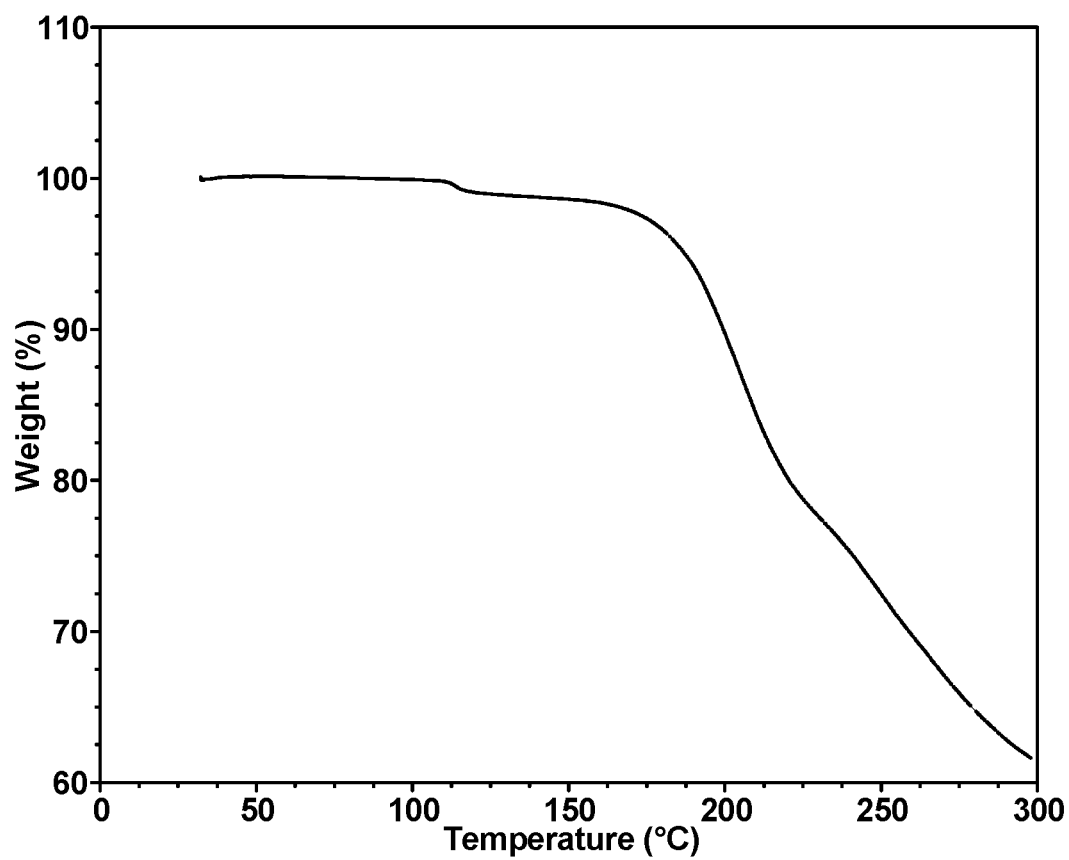
FIG. 12: TGA for Formula I Form IV

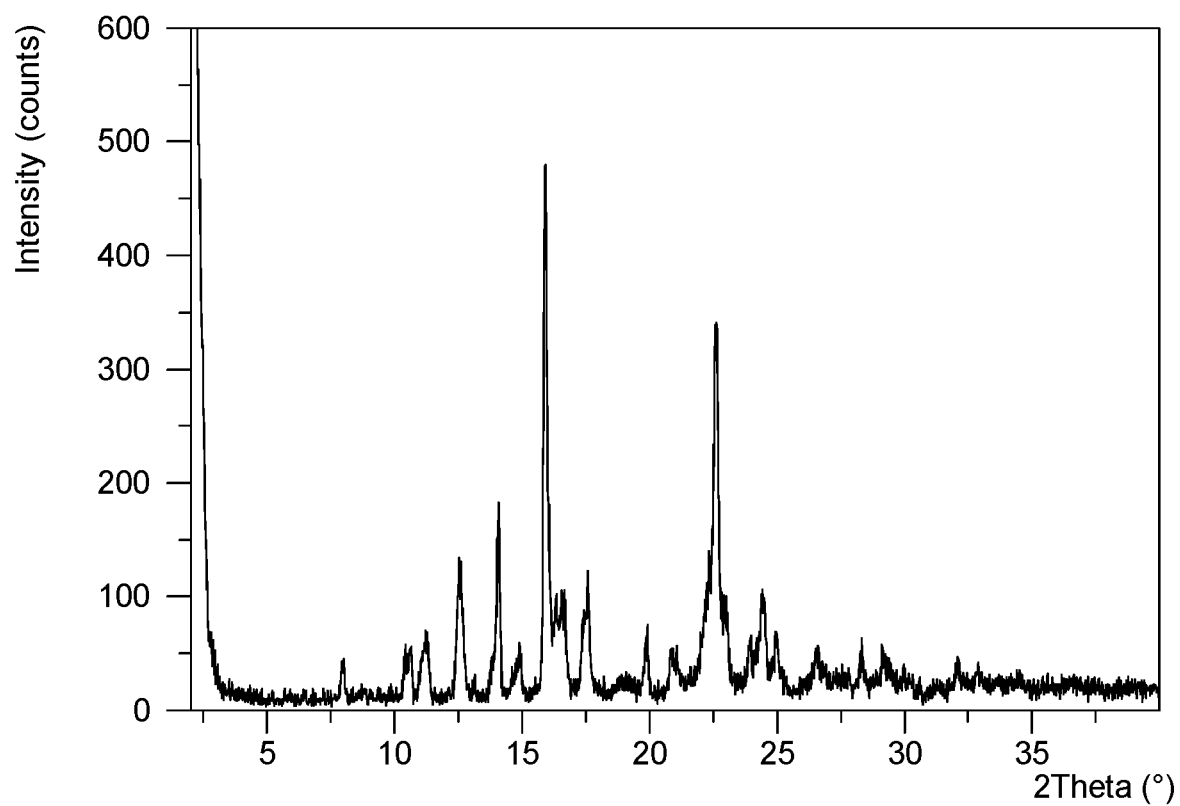
FIG. 13: XRPD pattern for Mixture I

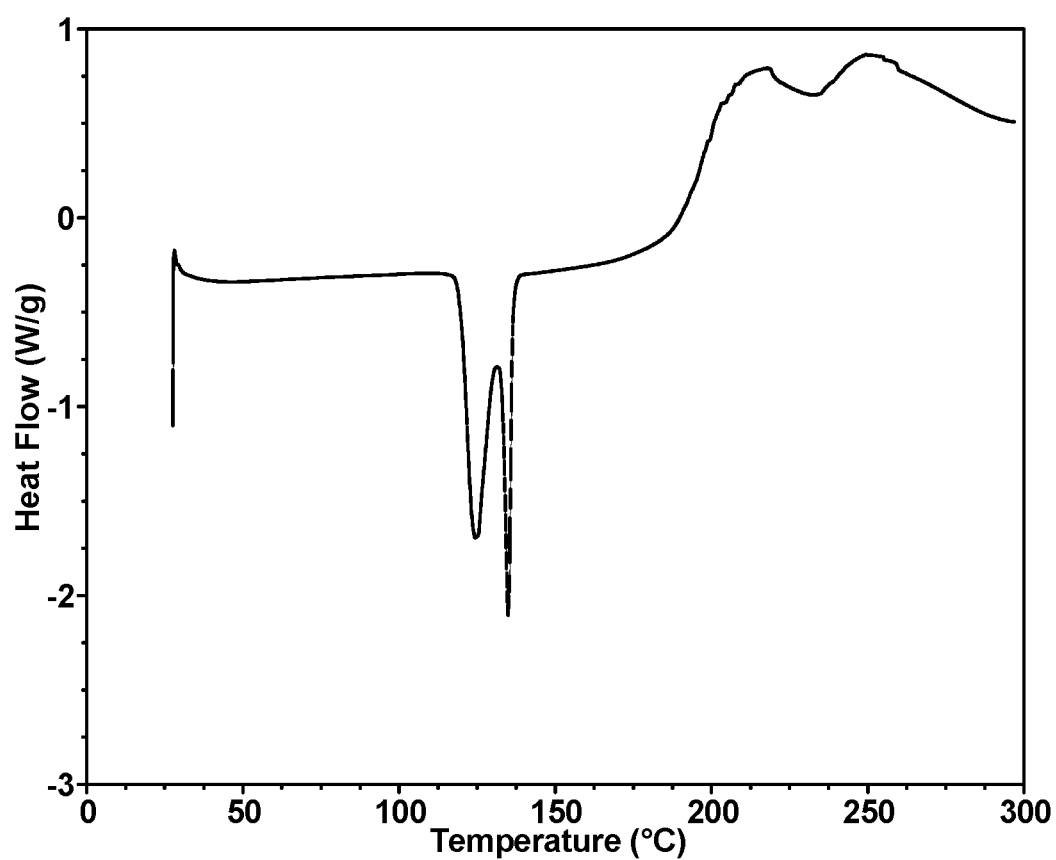
FIG. 14: DSC for Mixture I

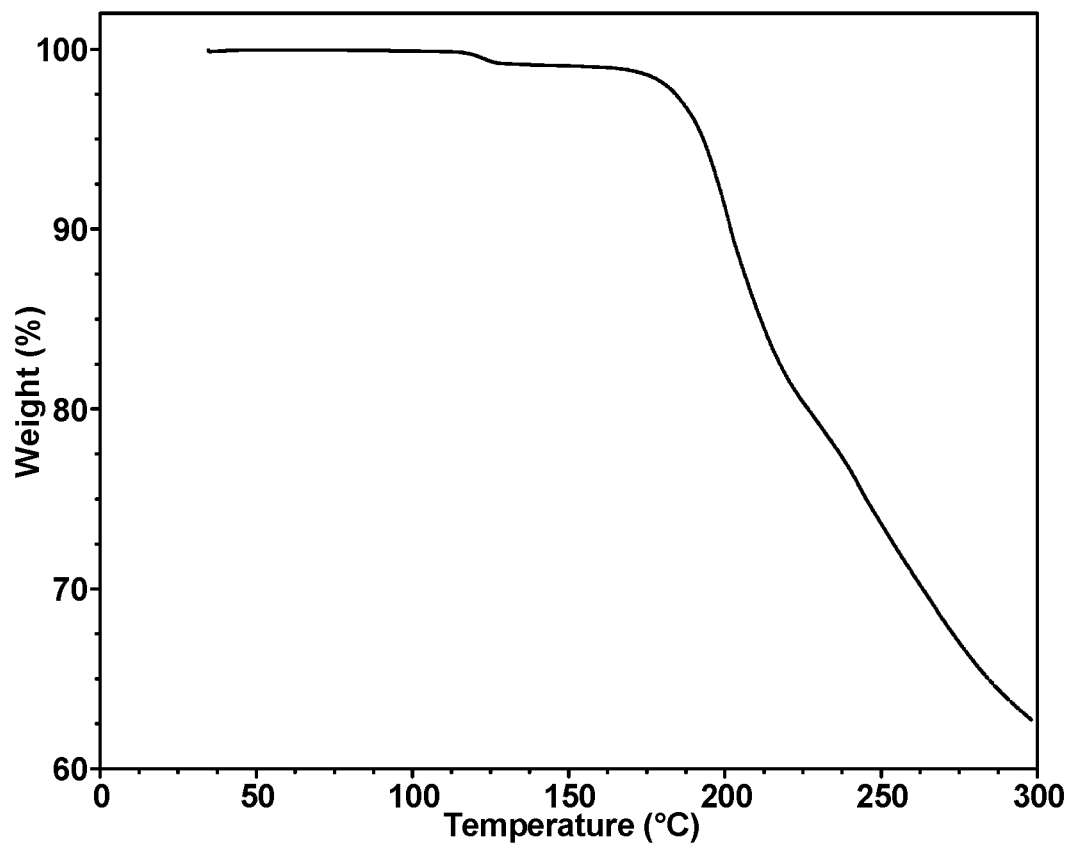
FIG. 15: TGA for Mixture I

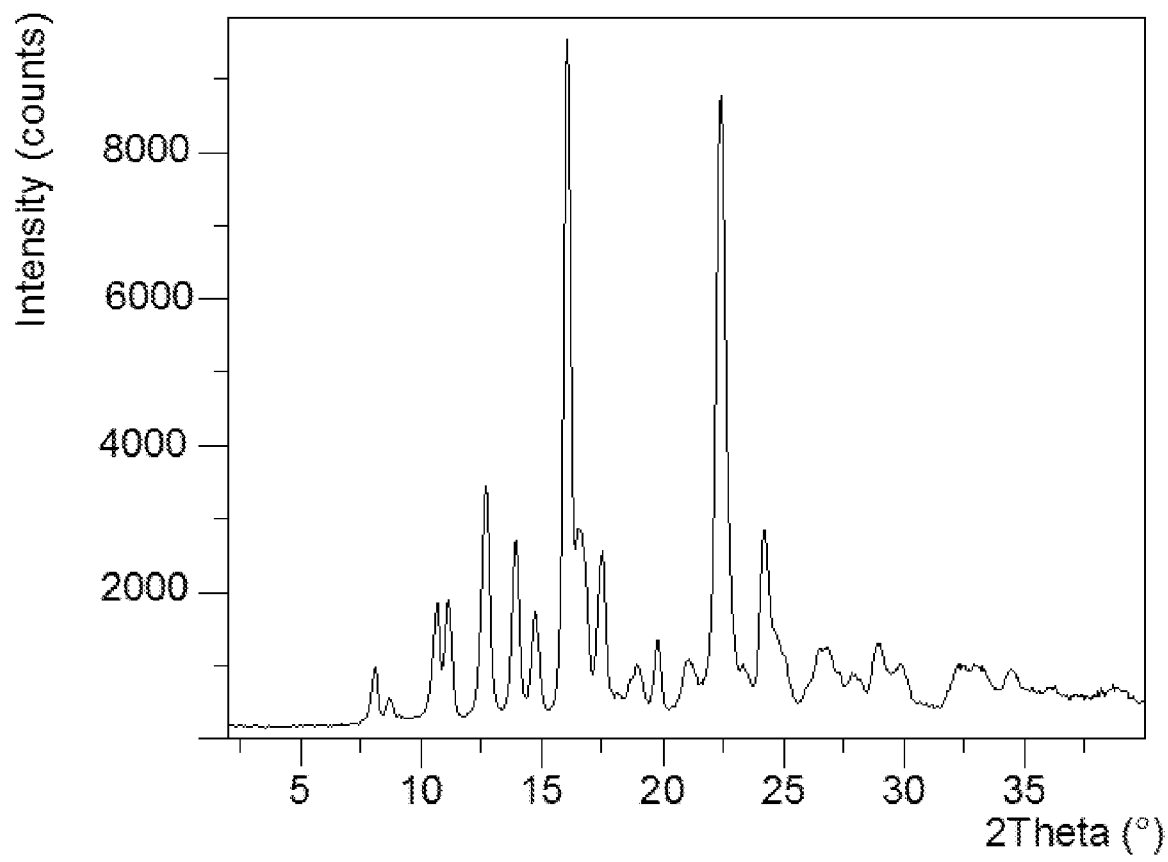
FIG. 16: XRPD pattern for Mixture II

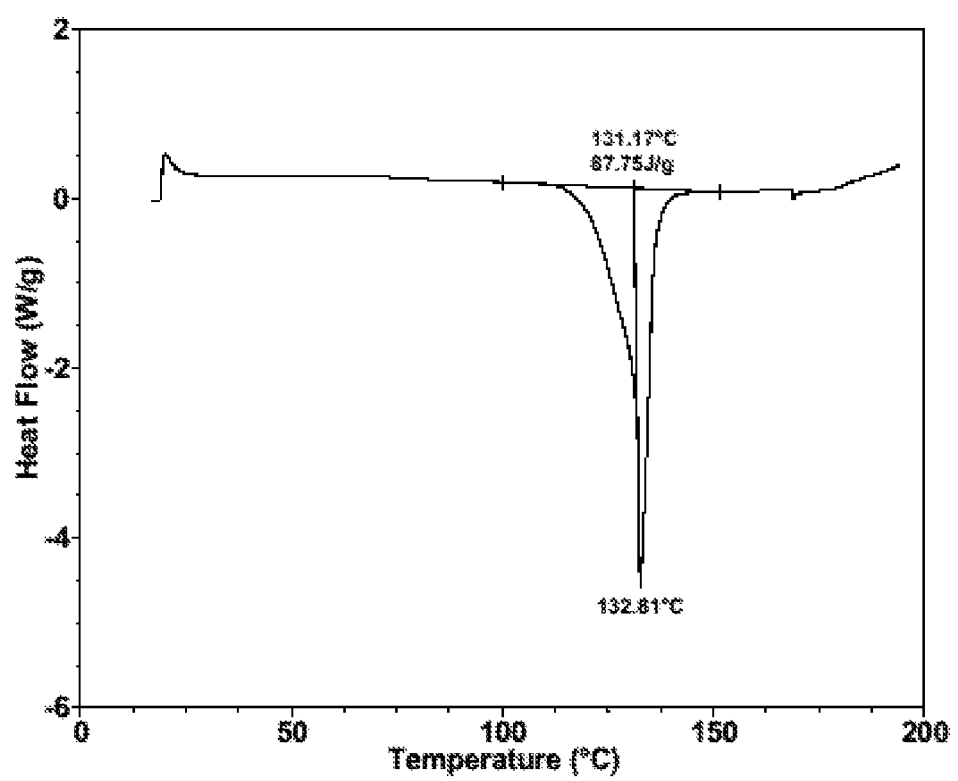
FIG. 17: DSC for Mixture II

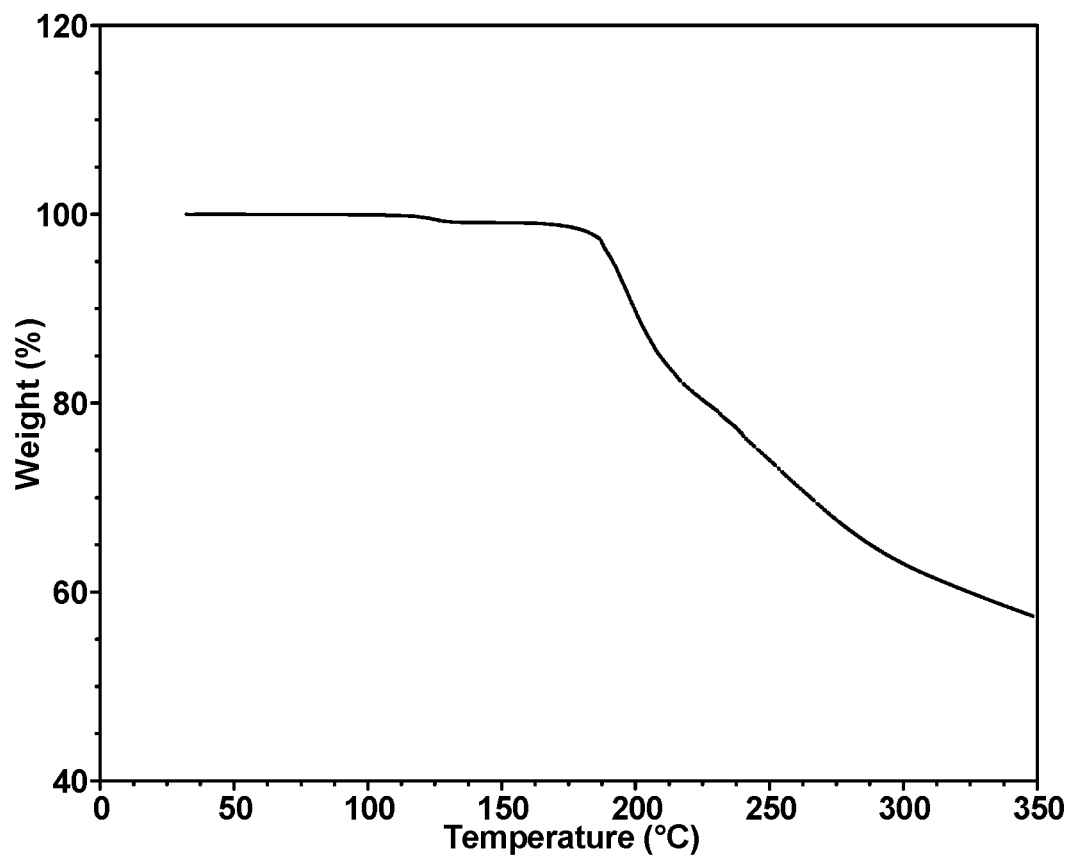
FIG. 18: TGA for Mixture II

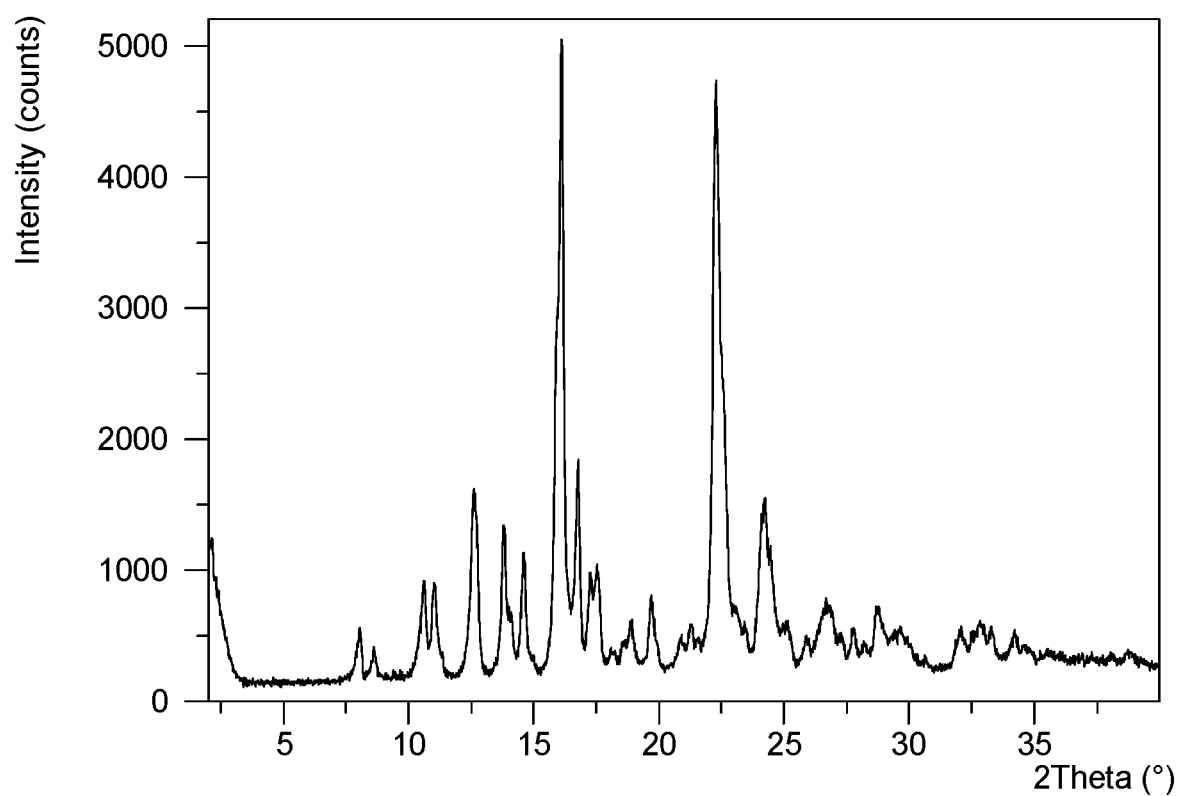
FIG. 19: XRPD pattern for Mixture III

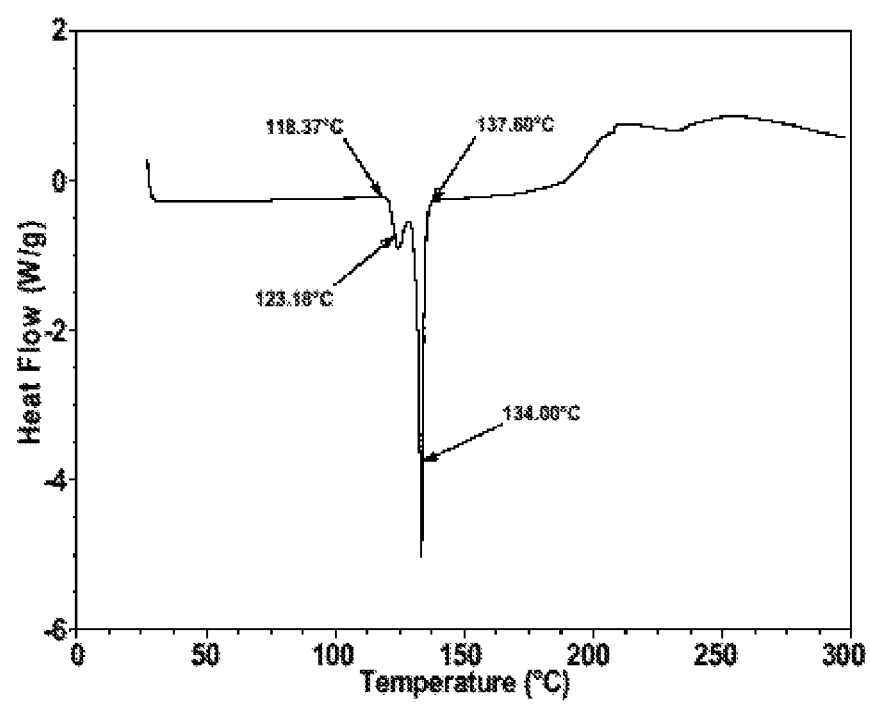
FIG. 20: DSC for Mixture III

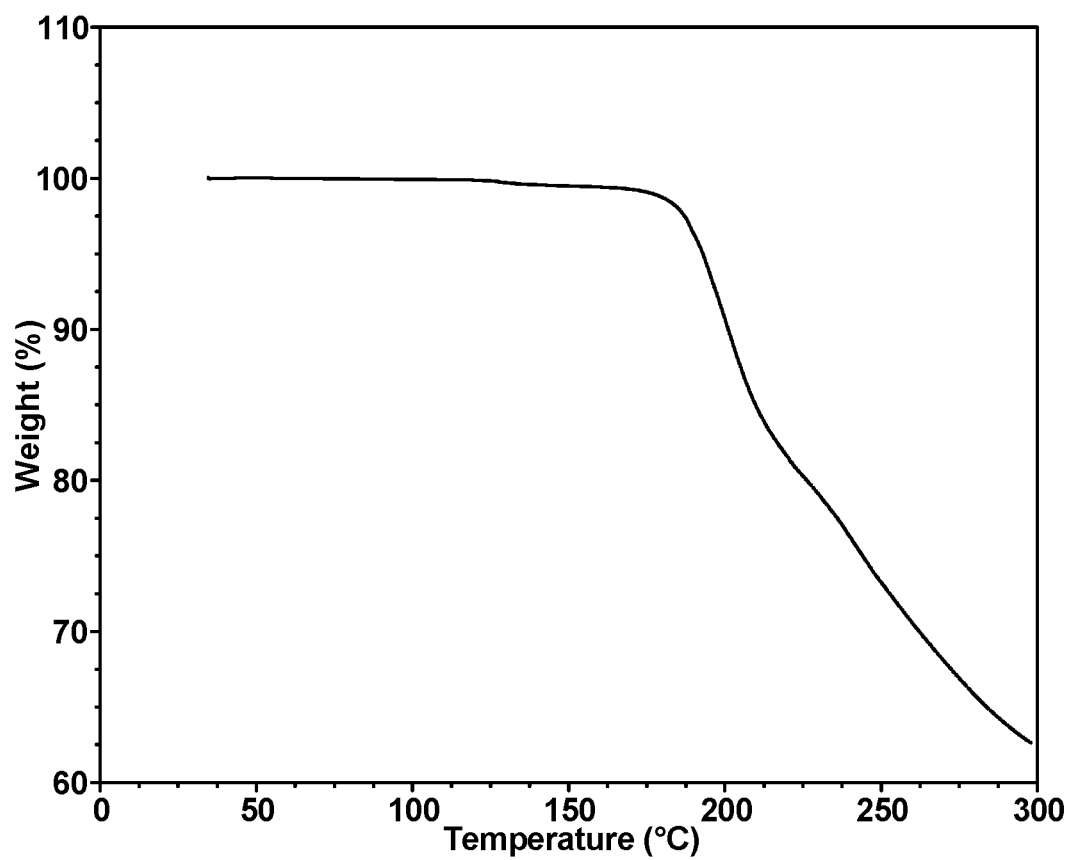
FIG. 21: TGA for Mixture III

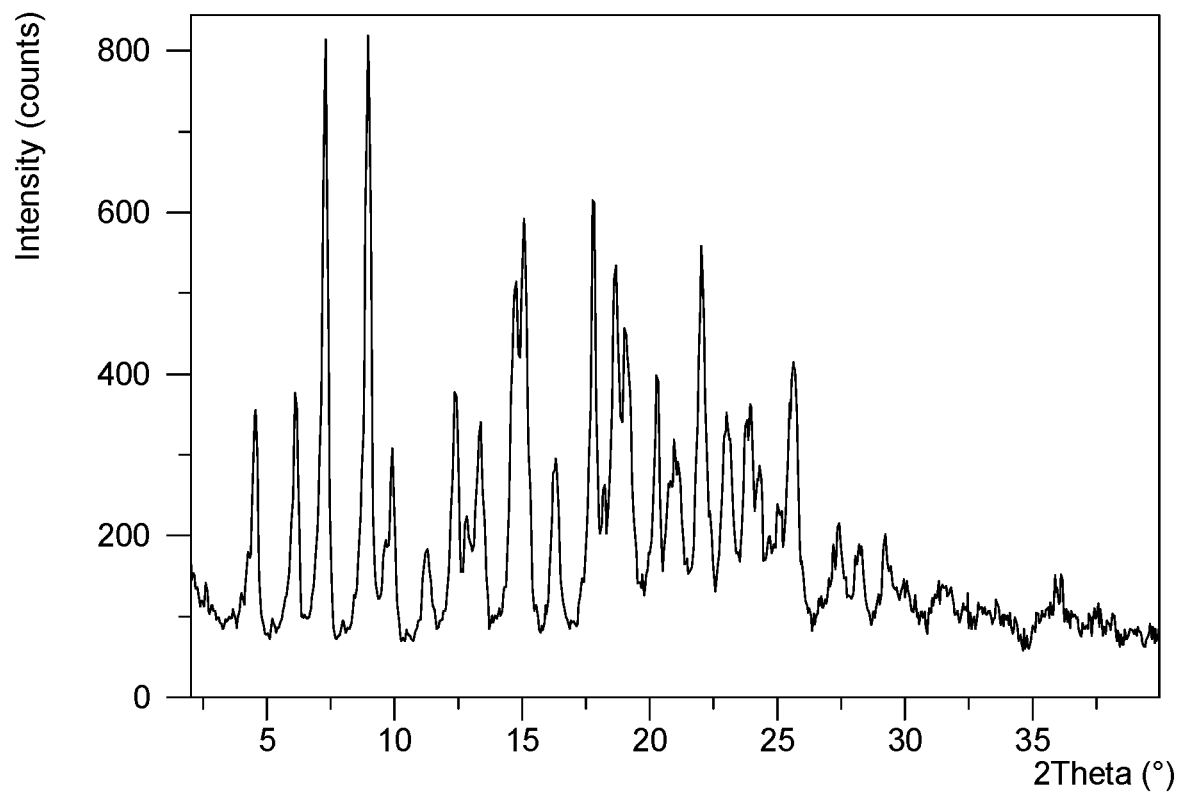
FIG. 22: XRPD pattern Formula I Maleate Form I

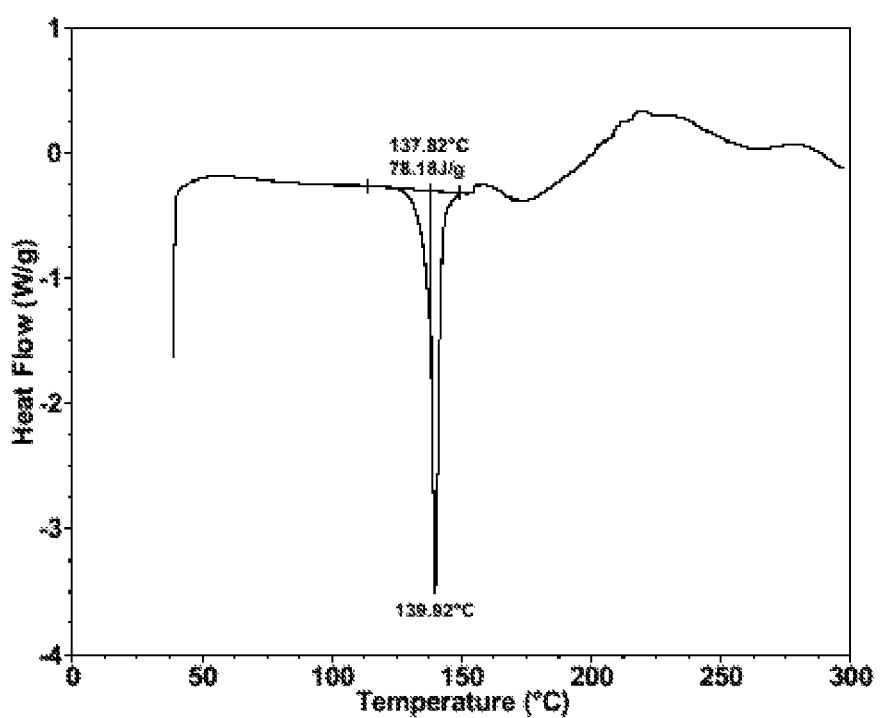
FIG. 23: DSC for Formula I Maleate Form I

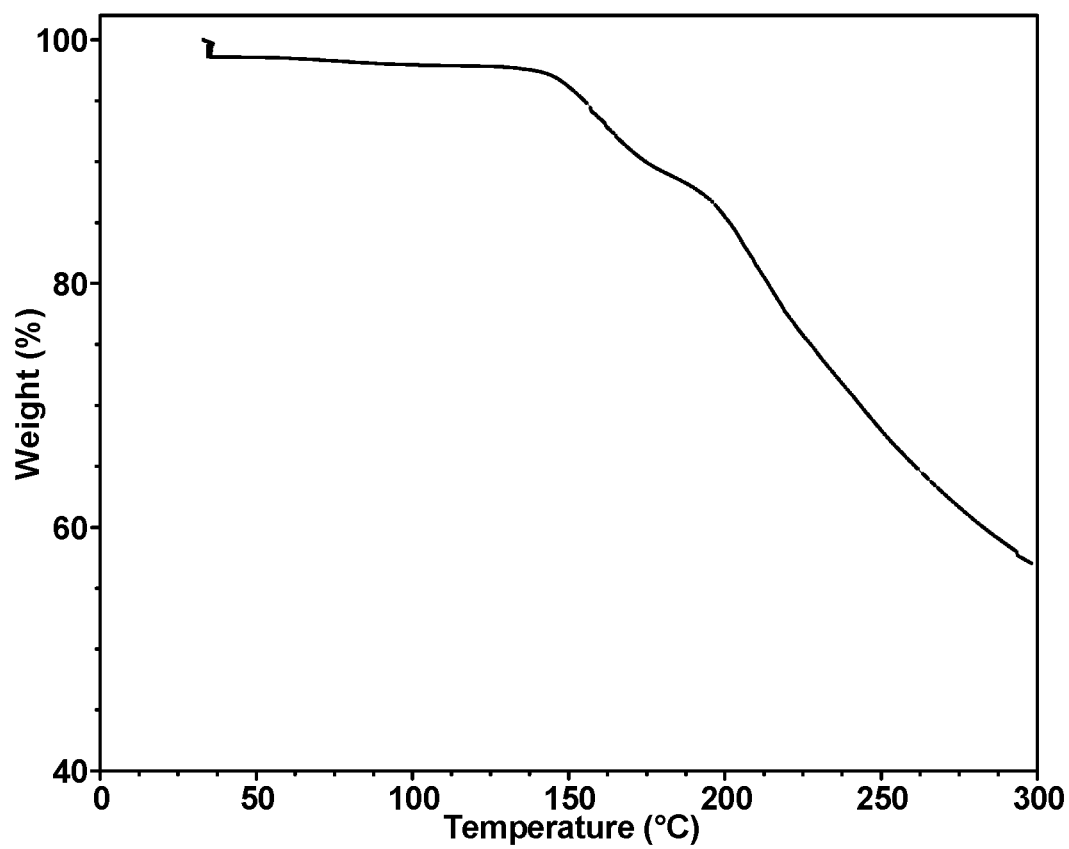
FIG. 24: TGA for Formula I Maleate Form I

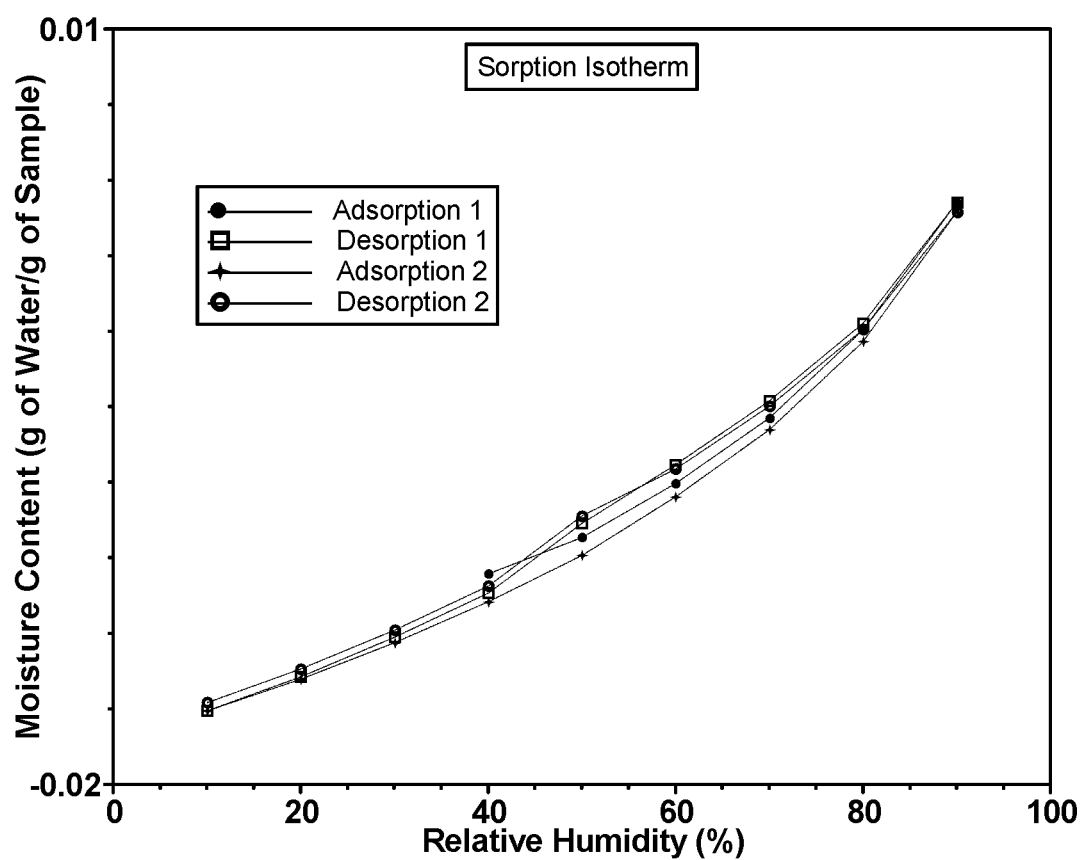
FIG. 25: DVS for Formula I Maleate Form I

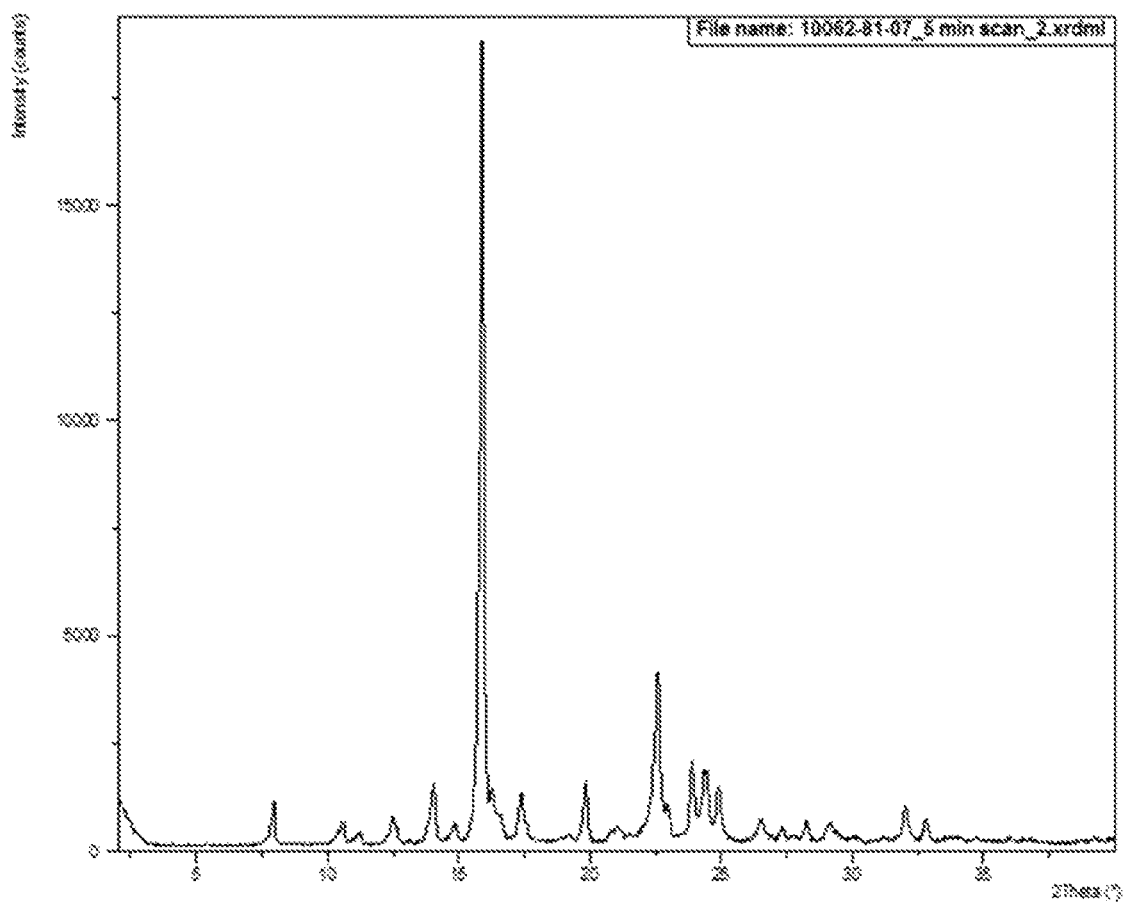
FIG. 26: XRPD pattern for Formula I Form IV

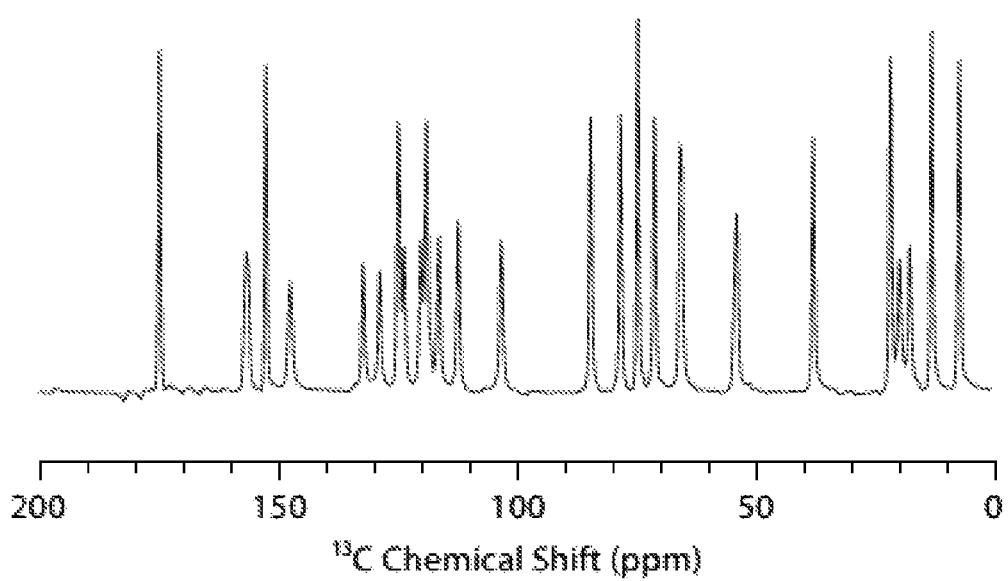
FIG. 27: Solid State NMR for Formula I Form II

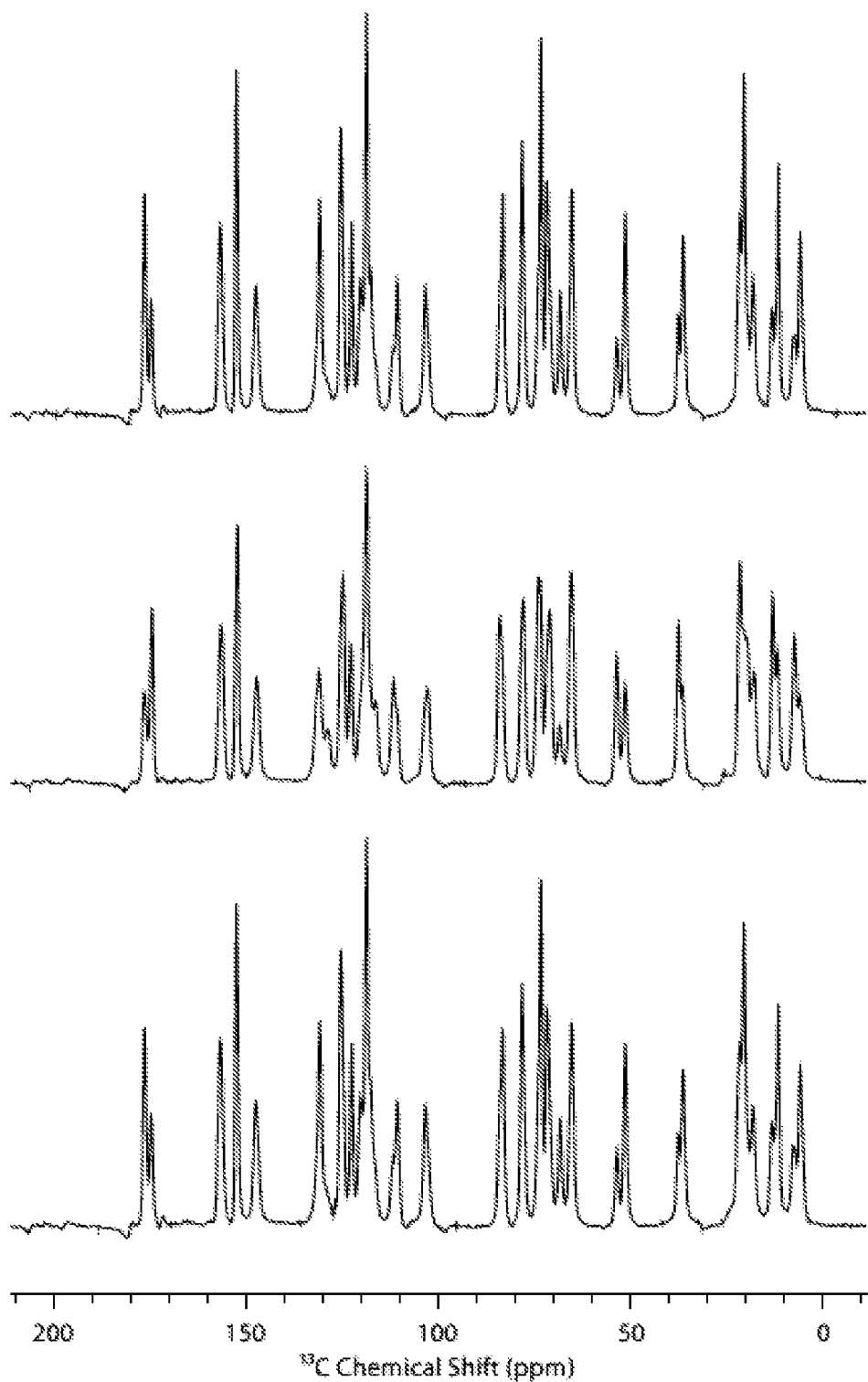
FIG. 28: Solid State NMR for Formula I forms

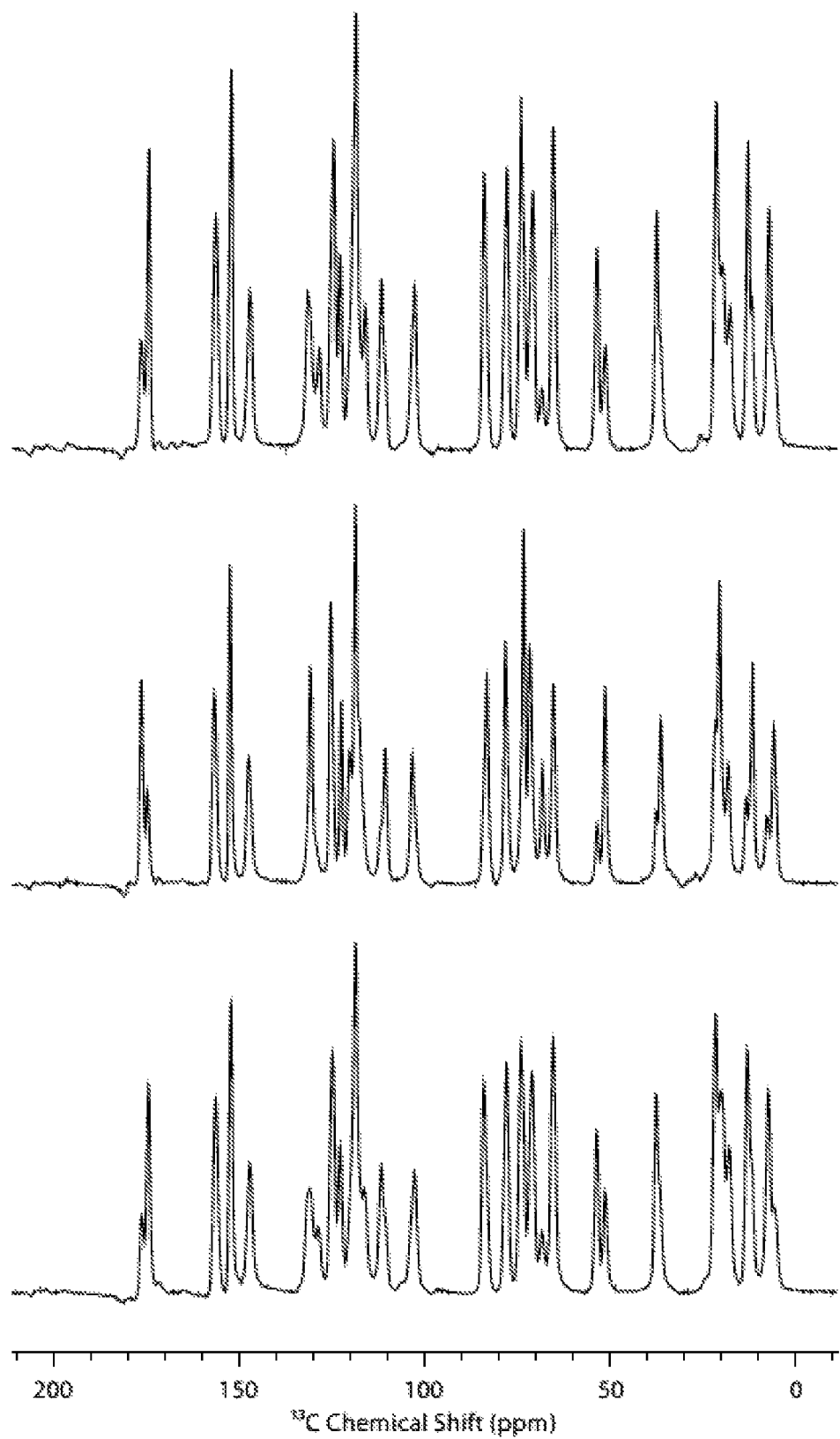
FIG. 29: Solid State NMR for Formula I forms

CRYSTALLINE FORMS OF (S)-2-ETHYLBUTYL 2-(((S)-(((2R,3S,4R,5R)-5-(4-AMINOPYRROLO[2,1-F] [1,2,4]TRIAZIN-7-YL)-5-CYANO-3,4-DIHYDROXYTETRAHYDROFURAN-2-YL) METHOXY)(PHENOXY) PHOSPHORYL)AMINO)PROPANOATE

CROSS-REFERENCES TO RELATED APPLICATIONS

This application claims priority to U.S. Provisional Application No. 62/492,364, filed May 1, 2017, which is incorporated herein in its entirety for all purposes.

FIELD

The present invention relates to novel crystalline forms of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate, the pharmaceutical formulations, and the therapeutic uses thereof in treating viral infections.

BACKGROUND OF THE INVENTION

Prevention and treatment methods for some Arenaviridae, Coronaviridae, Filoviridae, Flaviviridae, and Paramyxoviridae viruses present challenges due to a lack of vaccine or post-exposure treatment modality for preventing or managing these infections. In some cases, patients only receive supportive and resource intensive therapy such as electrolyte and fluid balancing, oxygen, blood pressure maintenance, or treatment for secondary infections. Thus, there is a need for antiviral therapies having a potential for broad antiviral activity.

The compound (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)propanoate, referred herein as Compound 1 or Formula I, is known to exhibit antiviral properties against Arenaviridae, Coronaviridae, Filoviridae, and Paramyxoviridae viruses as described in Warren, T. et al., Nature (2016) 531:381-385 and antiviral activities against Flaviviridae viruses as described in U.S. provisional patent application No. 62/325,419 filed Apr. 20, 2016.

(S)-2-Ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate or 2-ethylbutyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate, (Formula I), has the following structure:

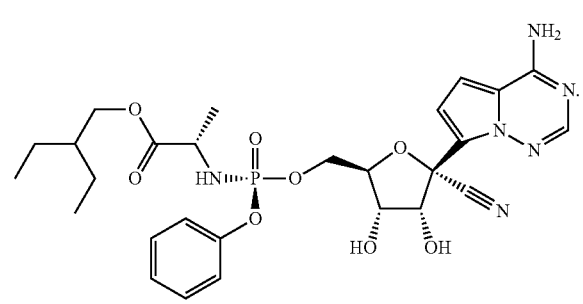 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

Formula I

It is desired to have physically stable forms of the compound that are suitable for the therapeutic use and the manufacturing process.

BRIEF SUMMARY OF THE INVENTION

In some embodiments, the present invention is directed to novel forms of Formula I.

In some embodiments, the present invention is directed to crystalline forms of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate.

In some embodiments, the present invention is directed to (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form I (Formula I Form I).

In some embodiments, the present invention is directed to (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form II (Formula I Form II).

In some embodiments, the present invention is directed to (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form III (Formula I Form III).

In some embodiments, the present invention is directed to (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form IV (Formula I Form IV)

In some embodiments, the present invention is directed to a mixture of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate crystalline forms (Formula I Mixture).

In some embodiments, the present invention is directed to a mixture of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form II and (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form IV (Mixture of Formula I Form II and Formula I Form IV).

In some embodiments, the present invention is directed to a mixture of crystalline forms of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (Mixture I)

In some embodiments, the present invention is directed to a mixture of crystalline forms of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (Mixture II)

In some embodiments, the present invention is directed to a mixture of crystalline forms of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (Mixture III)

In some embodiments, the present invention is directed to (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate maleate Form I (Formula I Maleate Form I)

In some embodiments, the present invention is directed to methods of treating an Arenaviridae, Coronaviridae, Filoviridae, Flaviviridae, or Paramyxoviridae virus infection by administering a compound of Formula I provided herein.

BRIEF DESCRIPTION OF THE DRAWINGS

FIG. 1: XRPD pattern for Formula I Form I.
FIG. 2: DSC for Formula I Form I.
FIG. 3: TGA for Formula I Form I.
FIG. 4: DVS for Formula I Form I.
FIG. 5: XRPD pattern for Formula I Form II.
FIG. 6: DSC for Formula I Form II.
FIG. 7: TGA for Formula I Form II.
FIG. 8: DVS for Formula I Form II.
FIG. 9: Calculated XRPD pattern for Formula I Form III.
FIG. 10: XRPD pattern for Form Formula I IV.
FIG. 11: DSC for Formula I Form IV.
FIG. 12: TGA for Formula I Form IV.
FIG. 13: XRPD pattern for a mixture of Formula I Form II and Formula I Form IV of Formula I (Mixture I).
FIG. 14: DSC for a mixture of Formula I Form II and Formula I Form IV of Formula I (Mixture I).
FIG. 15: TGA for a mixture of Formula I Form II and Formula I Form IV of Formula I (Mixture I).
FIG. 16: XRPD pattern for a mixture of Formula I Form II and Formula I Form IV of Formula I (Mixture II).
FIG. 17: DSC for a mixture of Formula I Form II and Formula I Form IV of Formula I (Mixture II).
FIG. 18: TGA for a mixture of Formula I Form II and Formula I Form IV of Formula I (Mixture II).
FIG. 19: XRPD pattern for a mixture of Formula I Form II and Formula I Form IV of Formula I (Mixture III).
FIG. 20: DSC for a mixture of Formula I Form II and Formula I Form IV of Formula I (Mixture III).
FIG. 21: TGA for a mixture of Formula I Form II and Formula I Form IV of Formula I (Mixture III).
FIG. 22: XRPD pattern Formula I Maleate Form I.
FIG. 23: DSC for Formula I Maleate Form I.
FIG. 24: TGA for Formula I Maleate Form I.
FIG. 25: DVS for Formula I Maleate Form I.
FIG. 26: XRPD pattern for Formula I Form IV.
FIG. 27: Solid state NMR for Formula I Form II.
FIG. 28: Solid state NMR for a mixture of Formula I Form II and Form IV (top), Mixture III (middle) and Mixture I (bottom).
FIG. 29: Solid state NMR for Mixture III (top), a mixture of Formula I Form II and Form IV (middle), and Mixture II (bottom).

DETAILED DESCRIPTION OF THE INVENTION

I. General

In the following description, certain specific details are set forth in order to provide a thorough understanding of various embodiments of the invention. However, one skilled in the art will understand that the invention may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

II. Definitions

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments that reference throughout this specification to "a Compound of Formula I" includes the crystalline, salt, co-crystal, and solvate forms of the formulas and/or compounds disclosed herein. Thus, the appearance or the phrase "a Compound of Formula I" comprises crystalline Forms I-IV and mixtures of crystalline forms thereof, Mixtures I-III, and Formula I Maleate Form I.

The invention disclosed herein is also meant to encompass all pharmaceutically acceptable compounds of Formula I being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formula I, for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection.

Substitution with heavier isotopes such as deuterium, i.e. $^{2}$H, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula I can generally be prepared by conventional techniques known to those skilled in the art or by processes analogous to those described in the Examples as set out below using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

A "pharmaceutical composition" refers to a formulation of a compound of the invention and a medium generally accepted in the art for the delivery of the biologically active compound to mammals, e.g., humans. Such a medium includes all pharmaceutically acceptable excipients therefor.

"Effective amount" or "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above. In some embodiments, the term "treatment" is intended to mean the administration of a compound or composition according to the present invention to alleviate or eliminate symptoms of an Arenaviridae virus infection and/or to reduce viral load in a patient. In some embodiments, the term "treatment" as used herein is further or alternatively intended to mean the administration of a compound or composition according to the present invention to alleviate or eliminate symptoms of a Coronaviridae virus infection and/or to reduce viral load in a patient. In some embodiments, the term "treatment" as used herein is further or alternatively intended to mean the administration of a compound or composition according to the present invention to alleviate or eliminate symptoms of a Filoviridae virus infection and/or to reduce viral load in a patient. In some embodiments, the term "treatment" as used herein is further or alternatively intended to mean the administration of a compound or composition according to the present invention to alleviate or eliminate symptoms of a Flaviviridae virus infection and/or to reduce viral load in a patient. In some embodiments, the term "treatment" as used herein is further or alternatively intended to mean the administration of a compound or composition according to the present invention to alleviate or eliminate symptoms of a Paramyxoviridae virus infection and/or to reduce viral load in a patient. In some embodiments, the term "treatment" as used herein is further or alternatively intended to mean the administration of a therapeutically effective amount of a compound or composition according to the present invention to maintain a reduced viral load in a patient.

"Prevention" or "preventing" means any treatment of a disease or condition that causes the clinical symptoms of the disease or condition not to develop. The term "prevention" also encompasses the administration of a therapeutically effective amount of a compound or composition according to the present invention pre-exposure of the individual to the virus (e.g., pre-exposure prophylaxis), to prevent the appearance of symptoms of the disease and/or to prevent the virus from reaching detectible levels in the blood.

The terms "Subject" or "patient" refer to an animal, such as a mammal (including a human), that has been or will be the object of treatment, observation or experiment. The methods described herein may be useful in human therapy and/or veterinary applications. In some embodiments, the subject is a mammal (or the patient). In some embodiments the subject (or the patient) is human, domestic animals (e.g., dogs and cats), farm animals (e.g., cattle, horses, sheep, goats and pigs), and/or laboratory animals (e.g., mice, rats, hamsters, guinea pigs, pigs, rabbits, dogs, and monkeys). In some embodiments, the subject (or the patient) is a human. "Human (or patient) in need thereof" refers to a human who may have or is suspect to have diseases or conditions that would benefit from certain treatment; for example, being treated with the compounds disclosed herein according to the present application.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of Arenaviridae virus replication" as used herein is intended to mean an agent capable of reducing or eliminating the ability of an Arenaviridae virus to replicate in a host cell, whether in vitro, ex vivo or in vivo.

The term "inhibitor of Coronaviridae virus replication" as used herein is intended to mean an agent capable of reducing or eliminating the ability of a Coronaviridae virus to replicate in a host cell, whether in vitro, ex vivo or in vivo.

The term "inhibitor of Filoviridae virus replication" as used herein is intended to mean an agent capable of reducing or eliminating the ability of a Filoviridae virus to replicate in a host cell, whether in vitro, ex vivo or in vivo.

The term "inhibitor of Flaviviridae virus replication" as used herein is intended to mean an agent capable of reducing or eliminating the ability of a Flaviviridae virus to replicate in a host cell, whether in vitro, ex vivo or in vivo.

The term "inhibitor of Paramyxoviridae virus replication" as used herein is intended to mean an agent capable of reducing or eliminating the ability of a Paramyxoviridae virus to replicate in a host cell, whether in vitro, ex vivo or in vivo.

A "tautomer" refers to a proton shift from one atom of a molecule to another atom of the same molecule. The present invention includes tautomers of any said compounds.

Reference to "about" a value or parameter herein includes (and describes) embodiments that are directed to that value or parameter per se. For example, description referring to "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

"Unit dosage forms" are physically discrete units suitable as unitary dosages for subjects (e.g., human subjects and other mammals), each unit containing a predetermined quantity of active material calculated to produce the desired therapeutic effect, in association with a suitable pharmaceutical excipient.

The term "substantially as shown in" when referring, for example, to an XRPD pattern, a DSC thermogram, DVS graphs, or a TGA graph includes a pattern, thermogram or graph that is not necessarily identical to those depicted herein, but that falls within the limits of experimental error or deviations when considered by one of ordinary skill in the art. Mixtures I-III are understood have different ratios of Formula I Form II to Formula I Form IV (Formula I Form II:Formula I Form IV). Accordingly, one of ordinary skill in the art would appreciate that other mixtures of Formula I Form II and Formula I Form IV may exist with data substantially as shown in the XRPD patterns, DSC thermograms, or TGA graphs provided herein, wherein the "substantially as shown" refers to a variance in purity of a Formula I Form II and Formula I Form IV mixture.

In some embodiments, the term "substantially pure" or "substantially free" with respect to a particular crystalline form of a compound means that the composition comprising the crystalline form contains less than 99%, less than 95%, less than 90%, less than 85%, less than 80%, less than 75%, less than 70%, less than 65%, less than 60%, less than 55%, less than 50%, less than 40%, less than 30%, less than 20%, less than 15%, less than 10%, less than 5%, or less than 1% by weight of other substances, including other crystalline forms and/or impurities. In some embodiments, "substantially pure" or "substantially free of" refers to a substance free of other substances, including other crystalline forms and/or impurities. Impurities may, for example, include by-products or left over reagents from chemical reactions, contaminants, degradation products, other crystalline forms, water, and solvents.

III. Crystalline Forms

A. Formula I

It is desirable to develop a crystalline form of Formula I that may be useful in the synthesis of a compound of Formula I. A crystalline form of a Formula I may be an intermediate to the synthesis of Formula I. A crystalline form may have properties such as bioavailability, stability, purity, and/or manufacturability at certain conditions that may be suitable for medical or pharmaceutical uses.

Crystalline forms of Formula I, including substantially pure forms and mixtures of substantially pure forms, may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength), and stability (e.g., thermal stability, shelf life, etc.) of a pharmaceutical drug product or active ingredient. Such variations may affect the preparation or formulation of pharmaceutical compositions in different dosage or delivery forms, such as solutions or solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of Formula I may provide advantages such as: improving the manufacturing process of an active agent or the stability or storability of a drug product form of the compound or an active ingredient, and/or having suitable bioavailability and/or stability as an active agent.

The use of certain solvents and/or processes have been found to produce different crystalline forms of Formula I described herein which may exhibit one or more favorable characteristics described above. The processes for the preparation of the crystalline forms described herein, and characterization of these crystalline forms are described in greater detail below.

The compound name provided above is named according to IUPAC rules or using ChemBioDraw Ultra and one skilled in the art understands that the compound structure may be named or identified using other commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the compound structure provided above may also be named or identified as (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl) amino)propanoate under IUPAC, as 2-ethylbutyl ((S)-(((2R,3S,4R,5R)-5-(4-aminopyrrolo[2,1-f][1,2,4]triazin-7-yl)-5-cyano-3,4-dihydroxytetrahydrofuran-2-yl)methoxy) (phenoxy)phosphoryl)-L-alaninate according to ChemBioDraw Ultra, and as CAS Registry Number 1809249-37-3.

In particular embodiments, crystalline forms of Formula I are disclosed.

Formula I Form I

In some embodiments, provided is crystalline Form I of Formula I (crystalline Formula I Form I), wherein the crystal structure exhibits an X-ray powder diffraction (XRPD) pattern substantially as shown in FIG. 1. Crystalline Formula I Form I may exhibit a differential scanning calorimetry (DSC) thermogram substantially as shown in FIG. 2. Crystalline Formula I Form I may exhibit a thermogravimetric analysis (TGA) graph substantially as shown in FIG. 3. Crystalline Formula I Form I may exhibit dynamic vapor sorption (DVS) graphs substantially as shown in FIG. 4.

In some embodiments of crystalline Formula I Form I, at least one, at least two, at least three, at least four, or all of the following (a)-(d) apply: (a) crystalline Formula I Form I has an XRPD pattern substantially as shown in FIG. 1; (b) crystalline Formula I Form I has a DSC thermogram substantially as shown in FIG. 2; (c) crystalline Formula I Form I has a TGA graph substantially as shown in FIG. 3; (d) crystalline Formula I Form I has DVS graphs substantially as shown in FIG. 4.

In some embodiments, crystalline Formula I Form I has the following properties:
(a) an XRPD pattern substantially as shown in FIG. 1;
(b) a DSC thermogram substantially as shown in FIG. 2;
(c) a TGA graph substantially as shown in FIG. 3; and
(d) DVS graphs substantially as shown in FIG. 4.

In some embodiments, crystalline Formula I Form I has an XRPD pattern displaying at least two, at least three, at least four, at least five, or at least six of the degree 2θ-reflections with the greatest intensity as the XRPD pattern substantially as shown in FIG. 1.

In some embodiments, crystalline Formula I Form I has an XRPD pattern comprising degree 2θ-reflections (+/−0.2 degrees 2θ) at 5.3°, 20.6°, and 22.7°. In some embodiments, crystalline Formula I Form I has an XRPD pattern comprising degree 2θ-reflections (+/−0.2 degrees 2θ) at 5.3°, 20.6°, and 22.7° and one or more of the degree 2θ-reflections (+/−0.2 degrees 2θ) at 17.1° and 20.0°. In some embodiments, crystalline Formula I Form I has an XRPD pattern comprising degree 2θ-reflections (+/−0.2 degrees 2θ) at 5.3°, 20.6°, and 22.7° and one of the degree 2θ-reflections (+/−0.2 degrees 2θ) at 17.1° and 20.0°. In some embodiments, crystalline Formula I Form I has an XRPD pattern comprising degree 2θ-reflections (+/−0.2 degrees 2θ) at 5.3°, 20.6°, and 22.7° and two of the degree 2θ-reflections (+/−0.2 degrees 2θ) at 17.1° and 20.0°. In some embodiments, crystalline Formula I Form I has an XRPD pattern comprising degree 2θ-reflections (+/−0.2 degrees 2θ) at 5.3°, 20.6°, 22.7°, 17.1° and 20.0°. In some embodiments, crystalline Formula I Form I has an XRPD pattern comprising any three degree 2θ-reflections (+/−0.2 degrees 2θ) selected from the group consisting of 5.3°, 20.6°, 22.7°, 17.1° and 20.0°.

In some embodiments, crystalline Formula I Form I has an XRPD pattern comprising degree 2θ-reflections (+/−0.2 degrees 2θ) at 5.3°, 20.6°, 22.7°, 17.1° and 20.0° and one or more of the degree 2θ-reflections (+/−0.2 degrees 2θ) at 17.6°, 16.3°, and 13.7°. In some embodiments, crystalline Formula I Form I has an XRPD pattern comprising degree 2θ-reflections (+/−0.2 degrees 2θ) at 5.3°, 20.6°, 22.7°, 17.1° and 20.0° and one of the degree 2θ-reflections (+/−0.2 degrees 2θ) at 17.6°, 16.3°, and 13.7°. In some embodiments, crystalline Formula I Form I has an XRPD pattern comprising degree 2θ-reflections (+/−0.2 degrees 2θ) at 5.3°, 20.6°, 22.7°, 17.1° and 20.0° and two of the degree 2θ-reflections (+/−0.2 degrees 2θ) at 17.6°, 16.3°, and 13.7°. In some embodiments, crystalline Formula I Form I has an XRPD pattern comprising degree 2θ-reflections (+/−0.2 degrees 2θ) at 5.3°, 20.6°, 22.7°, 17.1°, 20.0°, 17.6°, 16.3°, and 13.7°. In some embodiments, crystalline Formula I Form I has an XRPD pattern comprising any three degree 2θ-reflections (+/−0.2 degrees 2θ) selected from the group consisting of 5.3°, 20.6°, 22.7°, 17.1°, 20.0°, 17.6°, 16.3°, and 13.7°.

Formula I Form II

In some embodiments, provided is crystalline Form II of Formula I (crystalline Formula I Form II), wherein the crystal structure exhibits an X-ray powder diffraction (XRPD) pattern substantially as shown in FIG. 5. Crystalline Formula I Form II may exhibit a differential scanning calorimetry (DSC) thermogram substantially as shown in FIG. 6. Crystalline Formula I Form II may exhibit a thermogravimetric analysis (TGA) graph substantially as shown in FIG. 7. Crystalline Formula I Form II may exhibit dynamic vapor sorption (DVS) graphs substantially as shown in FIG. 8.

Crystalline Formula I Form II may have a unit cell as determined by single crystal X-ray crystallography of the following dimensions: a=10.505 (2) Å; b=12.736 (3) Å; c=11.066 (2) Å; α=90°; β=100.105 (7)°; and γ=90°.

In some embodiments of crystalline Formula I Form II, at least one, at least two, at least three, at least four, at least five, or all of the following (a)-(e) apply: (a) crystalline Formula I Form II has a unit cell, as determined by crystal X-ray crystallography at a temperature of 100 K, of the following dimensions: a=10.505 (2) Å; b=12.736 (3) Å; c=11.066 (2) Å; α=90°; β=100.105 (7)°; and γ=90°; (b) crystalline Formula I Form II has an XRPD pattern substantially as shown in FIG. 5; (c) crystalline Formula I Form II has a DSC thermogram substantially as shown in FIG. 6; (d) crystalline Formula I Form II has a TGA graph substantially as shown in FIG. 7; (e) crystalline Formula I Form II has DVS graphs substantially as shown in FIG. 8. In some embodiments of crystalline Formula I Form II, at least one, at least two, at least three, at least four, at least five, or all of the following (a)-(f) apply: (a) crystalline Formula I Form II has a unit cell, as determined by crystal X-ray crystallography at a temperature of 100 K, of the following dimensions: a=10.505 (2) Å; b=12.736 (3) Å; c=11.066 (2) Å; α=90°; β=100.105 (7)°; and γ=90°; (b) crystalline Formula I Form II has an XRPD pattern substantially as shown in FIG. 5; (c) crystalline Formula I Form II has a DSC thermogram substantially as shown in FIG. 6; (d) crystalline Formula I Form II has a TGA graph substantially as shown in FIG. 7; (e) crystalline Formula I Form II has DVS graphs substantially as shown in FIG. 8; (f) crystalline Formula I Form II has a solid state NMR substantially as shown in FIG. 27.

In some embodiments, crystalline Formula I Form II has the following properties:
(a) a unit cell, as determined by crystal X-ray crystallography at a temperature of 100 K, of the following dimensions a=10.505 (2) Å; b=12.736 (3) Å; c=11.066 (2) Å; α=90°; β=100.105 (7)°; and γ=90°;
(b) an XRPD pattern substantially as shown in FIG. 5;
(c) a DSC thermogram substantially as shown in FIG. 6;
(d) a TGA graph substantially as shown in FIG. 7; and
(e) DVS graphs substantially as shown in FIG. 8.

In some embodiments, crystalline Formula I Form II has the following properties:
(a) a unit cell, as determined by crystal X-ray crystallography at a temperature of 100 K, of the following dimensions a=10.505 (2) Å; b=12.736 (3) Å; c=11.066 (2) Å; α=90°; β=100.105 (7)°; and γ=90°;
(b) an XRPD pattern substantially as shown in FIG. 5;
(c) a DSC thermogram substantially as shown in FIG. 6;
(d) a TGA graph substantially as shown in FIG. 7;
(e) DVS graphs substantially as shown in FIG. 8; and
(f) a solid state NMR substantially as shown in FIG. 27.

In some embodiments, crystalline Formula I Form II has the following properties:
an X-ray powder diffraction (XRPD) pattern having peaks at about 22.3°, 16.9°, 16.2°, 13.8°, 12.7°, 22.5°, 10.6° and 14.5° 2-θ±0.2° 2-θ;
a Differential Scanning Calorimetry (DSC) thermogram peak at 138° C.; and
a unit cell as determined by single crystal X-ray crystallography of the following dimensions: a=10.505 (2) Å; b=12.736 (3) Å; c=11.066 (2) Å; α=90°; β=100.105 (7)°; and γ=90°.

In some embodiments, crystalline Formula I Form II has an XRPD pattern displaying at least two, at least three, at least four, at least five, or at least six of the degree 2θ-reflections with the greatest intensity as the XRPD pattern substantially as shown in FIG. 5.

In some embodiments, crystalline Formula I Form II has an XRPD pattern comprising degree 2θ-reflections (+/−0.2 degrees 2θ) at 22.3°, 16.9°, and 16.2°. In some embodiments, crystalline Formula I Form II has an XRPD pattern comprising degree 2θ-reflections (+/−0.2 degrees 2θ) at 22.3°, 16.9°, and 16.2° and one or more of the degree 2θ-reflections (+/−0.2 degrees 2θ) at 13.8° and 12.7°. In some embodiments, crystalline Formula I Form II has an XRPD pattern comprising degree 2θ-reflections (+/−0.2 degrees 2θ) at 22.3°, 16.9°, and 16.2° and one of the degree 2θ-reflections (+/−0.2 degrees 2θ) at 13.8° and 12.7°. In some embodiments, crystalline Formula I Form II has an XRPD pattern comprising degree 2θ-reflections (+/−0.2 degrees 2θ) at 22.3°, 16.9°, and 16.2° and two of the degree 2θ-reflections (+/−0.2 degrees 2θ) at 13.8° and 12.7°. In some embodiments, crystalline Formula I Form II has an XRPD pattern comprising degree 2θ-reflections (+/−0.2 degrees 2θ) at 22.3°, 16.9°, 16.2°, 13.8° and 12.7°. In some embodiments, crystalline Formula I Form II has an XRPD pattern comprising any three degree 2θ-reflections (+/−0.2 degrees 2θ) selected from the group consisting of 22.3°, 16.9°, 16.2°, 13.8°, and 12.7°.

In some embodiments, crystalline Formula I Form II has an XRPD pattern further comprising degree 2θ-reflections (+/−0.2 degrees 2θ) at 22.5°, 10.6° and 14.5°. In some embodiments, crystalline Formula I Form II has an XRPD pattern comprising degree 2θ-reflections (+/−0.2 degrees 2θ) at 22.3°, 16.9°, 16.2°, 13.8° and 12.7° and one or more of the degree 2θ-reflections (+/−0.2 degrees 2θ) at 22.5°, 10.6° and 14.5°. In some embodiments, crystalline Formula I Form II has an XRPD pattern comprising degree 2θ-reflections (+/−0.2 degrees 2θ) at 22.3°, 16.9°, 16.2°, 13.8° and 12.7° and one of the degree 2θ-reflections (+/−0.2 degrees 2θ) at 22.5°, 10.6° and 14.5°. In some embodiments, crystalline Formula I Form II has an XRPD pattern comprising degree 2θ-reflections (+/−0.2 degrees 2θ) at 22.3°, 16.9°, 16.2°, 13.8° and 12.7° and two of the degree 2θ-reflections (+/−0.2 degrees 2θ) at 22.5°, 10.6° and 14.5°. In some embodiments, crystalline Formula I Form II has an XRPD pattern comprising degree 2θ-reflections (+/−0.2 degrees 2θ) at 22.3°, 16.9°, 16.2°, 13.8°, 12.7°, 22.5°, 10.6° and 14.5°. In some embodiments, crystalline Formula I Form II has an XRPD pattern comprising any three degree 2θ-reflections (+/−0.2 degrees 2θ) selected from the group consisting of 22.3°, 16.9°, 16.2°, 13.8°, 12.7°, 22.5°, 10.6° and 14.5°.

Formula I Form III

In some embodiments, provided is crystalline Form III of Formula I (crystalline Formula I Form III), wherein the crystal structure exhibits a calculated powder pattern substantially as shown in FIG. 9.

Crystalline Formula I Form III may have a unit cell as determined by single crystal X-ray crystallography of the following dimensions: a=10.5800 (4) Å; b=7.4526 (4) Å; c=21.5691 (12) Å; α=90°; β=92.500 (3)°; and γ=90°.

In some embodiments of crystalline Formula I Form III, at least one, at least two, at least three, at least four, at least five, at least six, at least seven, or all of the following (a)-(g) apply: (a) crystalline Form III has a calculated powder pattern substantially as shown in FIG. 9; (b) crystalline Formula I Form III has a unit cell, as determined by crystal X-ray crystallography at a temperature of 100 K, of the following dimensions: a=10.5800 (4) Å; b=7.4526 (4) Å; c=21.5691 (12) Å; α=90°; β=92.500 (3)°; and γ=90°; (c) crystalline Formula I Form III has a monoclinic crystal system; (d) crystalline Formula I Form III has a P 21 space group; (e) crystalline Formula I Form III has a volume of 3884.0(8) Å$^3$; (f) crystalline Formula I Form III has a Z value of 2; and (g) crystalline Formula I Form III has a density of 1.348 Mg/m$^3$.

In some embodiments, crystalline Formula I Form III has the following properties:
  (a) a calculated powder pattern substantially as shown in FIG. 9; and
  (b) a unit cell, as determined by crystal X-ray crystallography at a temperature of 100 K, of the following dimensions a=10.5800 (4) Å; b=7.4526 (4) Å; c=21.5691 (12) Å; α=90°; β=92.500 (3)°; and γ=90°.

In some embodiments, crystalline Formula I Form III has a calculated powder pattern displaying at least two, at least three, at least four, at least five, or at least six of the degree 2θ-reflections with the greatest intensity as the calculated powder pattern substantially as shown in FIG. 9.

In some embodiments, crystalline Formula I Form III has a calculated powder pattern comprising degree 2θ-reflections (+/−0.2 degrees 2θ) at 4.1°, 8.2°, 17.1°, and 23.8°. In some embodiments, crystalline Form Formula I III has a calculated powder pattern comprising any three degree 2θ-reflections (+/−0.2 degrees 2θ) selected from the group consisting of 4.1°, 8.2°, 17.1°, and 23.8°.

In some embodiments, crystalline Formula I Form III has a calculated powder pattern comprising degree 2θ-reflections (+/−0.2 degrees 2θ) at 4.1°, 8.2°, 17.1°, and 23.8° and one or more of the degree 2θ-reflections (+/−0.2 degrees 2θ) at 16.9°, 14.4° and 25.6°. In some embodiments, crystalline Formula I Form III has a calculated powder pattern comprising degree 2θ-reflections (+/−0.2 degrees 2θ) at 4.1°, 8.2°, 17.1°, and 23.8° and one of the degree 2θ-reflections (+/−0.2 degrees 2θ) at 16.9°, 14.4° and 25.6°. In some embodiments, crystalline Formula I Form III has a calculated powder pattern comprising degree 2θ-reflections (+/−0.2 degrees 2θ) at 4.1°, 8.2°, 17.1°, and 23.8° and two of the degree 2θ-reflections (+/−0.2 degrees 2θ) at 16.9°, 14.4° and 25.6°. In some embodiments, crystalline Formula I Form III has a calculated powder pattern comprising degree 2θ-reflections (+/−0.2 degrees 2θ) at 4.1°, 8.2°, 17.1°, 23.8°, 16.9°, 14.4° and 25.6°.

Formula I Form IV

In some embodiments, provided is crystalline Form IV of Formula I (crystalline Formula I Form IV), wherein the crystal structure exhibits an X-ray powder diffraction (XRPD) pattern substantially as shown in FIG. 10. Crystalline Formula I Form IV may exhibit a differential scanning calorimetry (DSC) thermogram substantially as shown in FIG. 11. Crystalline Formula I Form IV may exhibit a thermogravimetric analysis (TGA) graph substantially as shown in FIG. 12.

In some embodiments of crystalline Formula I Form IV, at least one, at least two, or all of the following (a)-(c) apply: (a) crystalline Formula I Form IV has an XRPD pattern substantially as shown in FIG. 10; (b) crystalline Formula I Form IV has a DSC thermogram substantially as shown in FIG. 11; (c) crystalline Formula I Form IV has a TGA graph substantially as shown in FIG. 12.

In some embodiments, crystalline Formula I Form IV has the following properties:
  (a) an XRPD pattern substantially as shown in FIG. 10;
  (b) a DSC thermogram substantially as shown in FIG. 11; and
  (c) a TGA graph substantially as shown in FIG. 12.

In some embodiments, crystalline Formula I Form IV has an XRPD pattern displaying at least two, at least three, at least four, at least five, or at least six of the degree 2θ-reflections with the greatest intensity as the XRPD pattern substantially as shown in FIG. 10.

In some embodiments, crystalline Formula I Form IV has an XRPD pattern comprising degree 2θ-reflections (+/−0.2 degrees 2θ) at 22.6°, 19.9°, and 14.1°. In some embodiments, crystalline Formula I Form IV has an XRPD pattern comprising degree 2θ-reflections (+/−0.2 degrees 2θ) at 22.6°, 19.9°, and 14.1° and one or more of the degree 2θ-reflections (+/−0.2 degrees 2θ) at 17.4°, 8.0°, and 12.5°. In some embodiments, crystalline Formula I Form IV has an XRPD pattern comprising degree 2θ-reflections (+/−0.2 degrees 2θ) at 22.6°, 19.9°, and 14.1° and one of the degree 2θ-reflections (+/−0.2 degrees 2θ) at 17.4°, 8.0°, and 12.5°. In some embodiments, crystalline Formula I Form IV has an XRPD pattern comprising degree 2θ-reflections (+/−0.2 degrees 2θ) at 22.6°, 19.9°, and 14.1° and two of the degree 2θ-reflections (+/−0.2 degrees 2θ) at 17.4°, 8.0°, and 12.5°. In some embodiments, crystalline Formula I Form IV has an XRPD pattern comprising degree 2θ-reflections (+/−0.2 degrees 2θ) at 22.6°, 19.9°, and 14.1° and three of the degree 2θ-reflections (+/−0.2 degrees 2θ) at 17.4°, 8.0°, and 12.5°. In some embodiments, crystalline Formula I Form IV has an XRPD pattern comprising degree 2θ-reflections (+/−0.2 degrees 2θ) at 22.6°, 19.9°, 14.1°, 17.4°, 8.0°, and 12.5°. In some embodiments, crystalline Formula I Form IV has an XRPD pattern comprising any three degree 2θ-reflections (+/−0.2 degrees 2θ) selected from the group consisting of 22.6°, 19.9°, 14.1°, 17.4°, 8.0°, and 12.5°.

B. Mixtures of Forms of Formula I

Mixture I

In some embodiments, provided is a mixture of Forms II and IV of Formula I (Mixture I), wherein the crystal structure exhibits an X-ray powder diffraction (XRPD) pattern substantially as shown in FIG. 13. Mixture I may exhibit a differential scanning calorimetry (DSC) thermogram substantially as shown in FIG. 14. Mixture I may exhibit a thermogravimetric analysis (TGA) graph substantially as shown in FIG. 15.

In some embodiments of Mixture I, at least one, at least two, or all of the following (a)-(c) apply: (a) Mixture I has an XRPD pattern substantially as shown in FIG. 13; (b) Mixture I has a DSC thermogram substantially as shown in FIG. 14; (c) Mixture I has a TGA graph substantially as shown in FIG. 15.

In some embodiments, Mixture I has the following properties:
  (a) an XRPD pattern substantially as shown in FIG. 13;
  (b) a DSC thermogram substantially as shown in FIG. 14; and
  (c) a TGA graph substantially as shown in FIG. 15.

In some embodiments, Mixture I has an XRPD pattern displaying at least two, at least three, or at least four of the degree 2θ-reflections with the greatest intensity as the XRPD pattern substantially as shown in FIG. 13.

In some embodiments, Mixture I has an XRPD pattern comprising degree 2θ-reflections (+/−0.2 degrees 2θ) at 15.9°, 22.6°, and 14.1°. In some embodiments, Mixture I has an XRPD pattern comprising degree 2θ-reflections (+/−0.2 degrees 2θ) at 15.9°, 22.6°, and 14.1° and the degree 2θ-reflection (+/−0.2 degrees 2θ) at 12.5°. In some embodiments, Mixture I has an XRPD pattern comprising degree 2θ-reflections (+/−0.2 degrees 2θ) at 15.9°, 22.6°, 14.1°, and 12.5°. In some embodiments, Mixture I has an XRPD pattern comprising any three degree 2θ-reflections (+/−0.2 degrees 2θ) selected from the group consisting of 15.9°, 22.6°, 14.1°, and 12.5°.

Mixture II

In some embodiments, provided is a mixture of Forms II and IV of Formula I (Mixture II), wherein the crystal structure exhibits an X-ray powder diffraction (XRPD) pattern substantially as shown in FIG. 16. Mixture II may exhibit a differential scanning calorimetry (DSC) thermogram substantially as shown in FIG. 17. Mixture II may exhibit a thermogravimetric analysis (TGA) graph substantially as shown in FIG. 18.

In some embodiments of Mixture II, at least one, at least two, or all of the following (a)-(c) apply: (a) Mixture II has an XRPD pattern substantially as shown in FIG. 16; (b) Mixture II has a DSC thermogram substantially as shown in FIG. 17; (c) Mixture II has a TGA graph substantially as shown in FIG. 18.

In some embodiments, Mixture II has the following properties:
  (a) an XRPD pattern substantially as shown in FIG. 16;
  (b) a DSC thermogram substantially as shown in FIG. 17; and
  (c) a TGA graph substantially as shown in FIG. 18.

In some embodiments, Mixture II has an XRPD pattern displaying at least two, at least three, at least four, at least five, at least six, at least seven, at least eight, at least nine, at least ten, at least eleven, at least twelve of the degree 2θ-reflections with the greatest intensity as the XRPD pattern substantially as shown in FIG. 16.

In some embodiments, Mixture II has an XRPD pattern comprising degree 2θ-reflections (+/−0.2 degrees 2θ) at 16.1°, 22.4°, and 12.7°. In some embodiments, Mixture II has an XRPD pattern comprising degree 2θ-reflections (+/−0.2 degrees 2θ) at 16.1°, 22.4°, and 12.7° and one or more of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, and 12.7° and one of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, and 12.7° and two of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, and 12.7° and three of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, 12.7°, 24.2°, 16.8°, and 8.1°. In some embodiments, Mixture II has an XRPD pattern comprising any three degree 2θ-reflections (+/−0.2 degrees 2θ) selected from the group consisting of 16.1°, 22.4°, 12.7°, 24.2°, 16.8°, 8.1°, 13.9°, 17.5°, 11.1°, 10.7°, 14.7°, and 19.8°.

Mixture III

In some embodiments, provided is a mixture of Forms II and IV of Formula I (Mixture III), wherein the crystal structure exhibits an X-ray powder diffraction (XRPD) pattern substantially as shown in FIG. 19. Mixture III may exhibit a differential scanning calorimetry (DSC) thermogram substantially as shown in FIG. 20. Mixture III may exhibit a thermogravimetric analysis (TGA) graph substantially as shown in FIG. 21.

In some embodiments of Mixture III, at least one, at least two, or all of the following (a)-(c) apply: (a) Mixture III has an XRPD pattern substantially as shown in FIG. 19; (b) Mixture III has a DSC thermogram substantially as shown in FIG. 20; (c) Mixture III has a TGA graph substantially as shown in FIG. 21.

In some embodiments, Mixture III has the following properties:
(a) an XRPD pattern substantially as shown in FIG. 19;
(b) a DSC thermogram substantially as shown in FIG. 20; and
(c) a TGA graph substantially as shown in FIG. 21.

In some embodiments, Mixture III has an XRPD pattern displaying at least two, at least three, at least four, or at least five of the degree 2θ-reflections with the greatest intensity as the XRPD pattern substantially as shown in FIG. 19.

In some embodiments, Mixture III has an XRPD pattern comprising degree 2θ-reflections (+/−0.2 degrees 2θ) at 16.7°, 12.6°, and 17.2°. In some embodiments, Mixture III has an XRPD pattern comprising degree 2θ-reflections (+/−0.2 degrees 2θ) at 16.7°, 12.6°, and 17.2° and one or more of the degree 2θ-reflections (+/−0.2 degrees 2θ) at 19.6° and 14.1°. In some embodiments, Mixture III has an XRPD pattern comprising degree 2θ-reflections (+/−0.2 degrees 2θ) at 16.7°, 12.6°, and 17.2° and one of the degree 2θ-reflections (+/−0.2 degrees 2θ) at 19.6° and 14.1°. In some embodiments, Mixture III has an XRPD pattern comprising degree 2θ-reflections (+/−0.2 degrees 2θ) at 16.7°, 12.6°, and 17.2° and two of the degree 2θ-reflections (+/−0.2 degrees 2θ) at 19.6° and 14.1°. In some embodiments, Mixture III has an XRPD pattern comprising degree 2θ-reflections (+/−0.2 degrees 2θ) at 16.7°, 12.6°, 17.2°, 19.6° and 14.1°. In some embodiments, Mixture III has an XRPD pattern comprising any three degree 2θ-reflections (+/−0.2 degrees 2θ) selected from the group consisting of 16.7°, 12.6°, 17.2°, 19.6° and 14.1°.

C. Formula I Maleate Form I

In some embodiments, provided is crystalline Formula I Maleate (crystalline Formula I Maleate Form I), wherein the crystal structure exhibits an X-ray powder diffraction (XRPD) pattern substantially as shown in FIG. 22. Crystalline Formula I Maleate Form I may exhibit a differential scanning calorimetry (DSC) thermogram substantially as shown in FIG. 23. Crystalline Formula I Maleate Form I may exhibit a thermogravimetric analysis (TGA) graph substantially as shown in FIG. 24. Crystalline Formula I Maleate Form I may exhibit dynamic vapor sorption (DVS) graphs substantially as shown in FIG. 25.

In some embodiments of crystalline Formula I Maleate Form I, at least one, at least two, at least three, or all of the following (a)-(d) apply: (a) crystalline Formula I Maleate Form I has an XRPD pattern substantially as shown in FIG. 22; (b) crystalline Formula I Maleate Form I has a DSC thermogram substantially as shown in FIG. 23; (c) crystalline Formula I Maleate Form I has a TGA graph substantially as shown in FIG. 24; and (d) crystalline Formula I Maleate Form I has DVS graphs substantially as shown in FIG. 25.

In some embodiments, crystalline Formula I Maleate Form I has the following properties:
(a) an XRPD pattern substantially as shown in FIG. 22;
(b) a DSC thermogram substantially as shown in FIG. 23;
(c) TGA graphs substantially as shown in FIG. 24; and
(d) DVS graphs substantially as shown in FIG. 25.

In some embodiments, crystalline Formula I Maleate Form I has an XRPD pattern displaying at least two, at least three, at least four, at least five, or at least six of the degree 2θ-reflections with the greatest intensity as the XRPD pattern substantially as shown in FIG. 22.

In some embodiments, crystalline Formula I Maleate Form I has an XRPD pattern comprising degree 2θ-reflections (+/−0.2 degrees 2θ) at 16.3°, 4.6°, and 9.0°. In some embodiments, crystalline Formula I Maleate Form I has an XRPD pattern comprising degree 2θ-reflections (+/−0.2 degrees 2θ) at 16.3°, 4.6°, and 9.0° and one or more of the degree 2θ-reflections (+/−0.2 degrees 2θ) 6.2° and 7.3°. In some embodiments, crystalline Formula I Maleate Form I has an XRPD pattern comprising degree 2θ-reflections (+/−0.2 degrees 2θ) at 16.3°, 4.6°, and 9.0° and one of the degree 2θ-reflections (+/−0.2 degrees 2θ) at 6.20 and 7.3°. In some embodiments, crystalline Formula I Maleate Form I has an XRPD pattern comprising degree 2θ-reflections (+/−0.2 degrees 2θ) at 16.3°, 4.6°, and 9.0° and two of the degree 2θ-reflections (+/−0.2 degrees 2θ) at 6.20 and 7.3°. In some embodiments, crystalline Formula I Maleate Form I has an XRPD pattern comprising degree 2θ-reflections (+/−0.2 degrees 2θ) at 16.3°, 4.6°, 9.0°, 6.2° and 7.3°. In some embodiments, crystalline Formula I Maleate Form I has an XRPD pattern comprising any three degree 2θ-reflections (+/−0.2 degrees 2θ) selected from the group consisting of 16.3°, 4.6°, 9.0°, 6.2° and 7.3°.

In some embodiments, crystalline Formula I Maleate Form I has an XRPD pattern comprising degree 2θ-reflections (+/−0.2 degrees 2θ) at 16.3°, 4.6°, 9.0°, 6.2° and 7.3° and one or more of the degree 2θ-reflections (+/−0.2 degrees 2θ) 17.8°, 15.1° and 14.7°. In some embodiments, crystalline Formula I Maleate Form I has an XRPD pattern comprising degree 2θ-reflections (+/−0.2 degrees 2θ) at 16.3°, 4.6°, 9.0°, 6.2° and 7.3° and one of the degree 2θ-reflections (+/−0.2 degrees 2θ) at 17.8°, 15.1° and 14.7°. In some embodiments, crystalline Formula I Maleate Form I has an XRPD pattern comprising degree 2θ-reflections (+/−0.2 degrees 2θ) at 16.3°, 4.6°, 9.0°, 6.2° and 7.3° and two of the degree 2θ-reflections (+/−0.2 degrees 2θ) at 17.8°, 15.1° and 14.7°. In some embodiments, crystalline Formula I Maleate Form I has an XRPD pattern comprising degree 2θ-reflections (+/−0.2 degrees 2θ) at 16.3°, 4.6°, 9.0°, 6.2°, 7.3°, 17.8°, 15.1° and 14.7°. In some embodiments, crystalline Formula I Maleate Form I has an XRPD pattern comprising any three degree 2θ-reflections (+/−0.2 degrees 2θ) selected from the group consisting of 16.3°, 4.6°, 9.0°, 6.2°, 7.3°, 17.8°, 15.1° and 14.7°.

IV. Pharmaceutical Compositions

For the purposes of administration, in some embodiments, the compounds described herein are administered as a raw chemical or are formulated as pharmaceutical compositions. Pharmaceutical compositions of the present invention comprise a therapeutically effective amount of a compound of Formula I, including forms thereof, and a pharmaceutically acceptable excipient. The compound of Formula I is present in the composition in an amount which is effective to treat a particular disease or condition of interest. The activity of compounds of Formula I can be determined by one skilled in the art, for example, as described herein. Appropriate therapeutically effective concentrations and dosages can be readily determined by one skilled in the art. In some embodiments, a compound of Formula I is present in the pharmaceutical composition in an amount from about 5 mg to about 300 mg. In some embodiments, a compound of Formula I is present in the pharmaceutical composition in an amount of about 100 mg to about 200 mg. In some embodiments, a compound of Formula I is present in the pharmaceutical composition in an amount of about 5 mg to about 100 mg. In some embodiments, a compound of Formula I is present in the pharmaceutical composition in an amount of about 5 mg to about 20 mg. In some embodiments, a compound of Formula I is present in the pharmaceutical composition in an amount of about 130 mg to about 160 mg.

In some embodiments, a compound of Formula I is present in the pharmaceutical composition in an amount of about 5 mg, 10 mg, 25 mg, 50 mg, 75, mg, 100 mg, 150 mg, 200 mg, 250 mg, or about 300 mg. In some embodiments, a compound of Formula I is present in the pharmaceutical composition in an amount of about 10 mg. In some embodiments, a compound of Formula I is present in the pharmaceutical composition in an amount of about 150 mg. In some embodiments, a compound of Formula I is present in the pharmaceutical composition in an amount of about 10 mg. In some embodiments, a compound of Formula I is present in the pharmaceutical composition in an amount of about 150 mg.

Administration of the compounds of the invention in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable excipient, and may be formulated into preparations in solid, semi-solid, liquid or gaseous forms, such as tablets, capsules, powders, granules, ointments, solutions, suppositories, injections, inhalants, gels, microspheres, and aerosols. The pharmaceutical compositions of the invention can be prepared by combining a compound of the invention with an appropriate pharmaceutically acceptable excipient, and may be formulated into preparations in solid, semi-solid, liquid or gaseous forms, such as solid dispersions and solid solutions. Typical routes of administering such pharmaceutical compositions include, without limitation, oral, topical, transdermal, inhalation, parenteral, sublingual, buccal, rectal, vaginal, and intranasal. In some embodiments, the pharmaceutical composition is prepared for parental administration. In a specific embodiment, the pharmaceutical composition is a solution. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention for treatment of a disease or condition of interest in accordance with the teachings of this invention.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. Alternatively, a pharmaceutical composition intended to be administered by injection can be prepared by combining a compound of the invention with sterile, reverse osmosis water so as to form a solution. A surfactant or other solubilizing excipient may be added to facilitate the formation of a homogeneous solution or suspension. Surfactants are compounds that non-covalently interact with the compound of the invention so as to facilitate dissolution or homogeneous suspension of the compound in the aqueous delivery system.

In other embodiments, a solid pharmaceutical composition intended for oral administration can be prepared by mixing a therapeutically effective amount of a compound of the invention with at least one suitable pharmaceutically acceptable excipient to form a solid preformulation composition, which then may be readily subdivided into equally effective unit dosage forms such as tablets, pills and capsules. Accordingly, in some embodiments, a pharmaceutical composition is provided, which includes a therapeutically effective amount of a compound of Formula I and a pharmaceutically acceptable excipient.

The compounds of the invention are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. In some embodiments, the compounds of the invention can be administered alone or in combination with other antiviral agents one time a day, or two times a day, or three times a day, or four times a day, for as long as the patient is infected, latently infected, or to prevent infection (e.g. for multiple years, months, weeks, or days).

The compositions of the present invention can include the compound of Formula I in any suitable purity. For example, the compound of Formula I can have a purity of at least 99.0%, or at least 99.1, 99.2, 99.3, 99.4, 99.5, 99.6, 99.7, 99.8 or at least 99.9%. In some embodiments, the present invention provides a composition having a compound of Formula I having a purity of at least 99.1%. In some embodiments, the present invention provides a composition having a compound of Formula I having a purity of at least 99.3%. In some embodiments, the present invention provides a composition having a compound of Formula I having a purity of at least 99.5%. In some embodiments, the present invention provides a composition having a compound of Formula I having a purity of at least 99.7%.

The impurities present in the compositions of the present invention can include unreacted starting material, undesirable side-products, and other materials. Representative impurities include Impurity A:

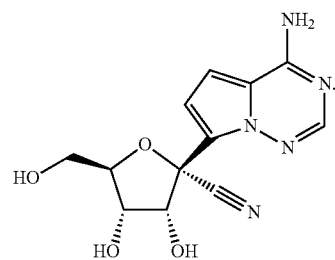 [SMILES: N#C[C@@]1(c2ccc3c(N)ncnn23)O[C@H](CO)[C@@H](O)[C@H]1O]

Impurity A can be present in the compositions of the present invention in amount less than about 0.5% (w/w), or less than about 0.45%, 0.40, 0.35, 0.30, 0.25, 0.20, 0.15, 0.10, 0.09, 0.08, 0.07, 0.06, 0.05, 0.04, 0.03, 0.02, or less than about 0.01% (w/w). In some embodiments, the composition of the compound of Formula I includes less than 0.10% (w/w) of Impurity A. In some embodiments, the composition of the compound of Formula I includes less than 0.05% (w/w) of Impurity A.

In some embodiments, a composition of a compound of Formula I can have a purity of at least 99.1%, wherein the composition includes less than 0.10% (w/w) of Impurity A. In some embodiments, a composition of a compound of Formula I can have a purity of at least 99.1%, wherein the composition includes less than 0.05% (w/w) of Impurity A. In some embodiments, a composition of a compound of Formula I can have a purity of at least 99.1%, wherein the composition includes less than 0.04% (w/w) of Impurity A. In some embodiments, a composition of a compound of Formula I can have a purity of at least 99.5%, wherein the composition includes less than 0.04% (w/w) of Impurity A. In some embodiments, a composition of a compound of Formula I can have a purity of at least 99.5%, wherein the composition includes less than 0.04% (w/w) of Impurity A.

Formula I

Provided are also compositions comprising at least one, at least two, at least three or all crystalline forms of Formula I as described herein. In a particular embodiment, a composition comprising one compound of Formula I described herein is provided. In a particular embodiment, a composition comprising two crystalline compounds of Formula I described herein is provided. In a particular embodiment, a composition comprising three crystalline compounds of Formula I described herein is provided. In a particular embodiment, a composition comprising four crystalline compounds of Formula I described herein is provided. In a particular embodiment, a composition comprising a mixture of crystalline Formula I Form II and Formula I Form IV described herein. In other embodiments, the compositions described herein may comprise substantially pure crystalline forms, or may be substantially free of other crystalline forms and/or impurities.

In some embodiments, the composition comprises a crystalline form of Formula I. In some embodiments are provided compositions comprising a crystalline form as described herein, wherein the compound of Formula I within the composition is substantially pure (i.e., substantially pure compound of Formula I described herein). In particular embodiments of compositions comprising a crystalline form of Formula I, at least about 50%, at least about 60%, at least about 70%, at least about 80%, at least about 85%, at least about 90%, at least about 95%, at least about 96%, at least about 97%, at least about 98%, or at least about 99% of Formula I present in the composition is one of the crystalline forms disclosed herein. In some embodiments, the composition includes at least about 50%, at least about 60%, at least about 70%, at least about 80%, at least about 85%, at least about 90%, at least about 95%, at least about 96%, at least about 97%, at least about 98%, or at least about 99% of one of the crystalline forms of Formula I.

In other embodiments of compositions comprising a crystalline form disclosed herein, less than about 50%, less than about 40%, less than about 30%, less than about 20%, less than about 10%, less than about 5%, less than about 4%, less than about 3%, less than about 2% or less than about 1% of Formula I present in the composition are other amorphous or crystal forms of Formula I and/or impurities.

In yet other embodiments of compositions comprising the crystalline forms disclosed herein, impurities make up less than about 5%, less than about 4%, less than about 3%, less than about 2% or less than about 1% of the total mass relative to the mass of the crystalline forms present. Impurities may, for example, include by-products from synthesizing Formula I, contaminants, degradation products, other crystalline forms, amorphous form, water, and solvents. In some embodiments, impurities include by-products from the process of synthesizing Formula I. In some embodiments, impurities include contaminants from the process of synthesizing Formula I. In some embodiments, impurities include degradation products of Formula I. In some embodiments, impurities include other crystalline forms of Formula I. In some embodiments, impurities include water or solvent. In some embodiments of compositions comprising a crystalline form disclosed herein, impurities are selected from the group consisting of by-products from synthesizing Formula I, contaminants, degradation products, other crystalline forms, water, solvents and combinations thereof.

Combination Therapy

In some embodiments, a method for treating an Arenaviridae virus infection in a human is provided, comprising administering to the human a therapeutically effective amount of a compound disclosed herein in combination with a therapeutically effective amount of one or more (e.g., one, two, three, one or two, or one to three) additional therapeutic agents. In some embodiments, a method for treating a Lassa virus infection in a human is provided, comprising administering to the human a therapeutically effective amount of a compound disclosed herein in combination with a therapeutically effective amount of one or more (e.g., one, two, three, one or two, or one to three) additional therapeutic agents. In some embodiments, a method for treating a Junin virus infection in a human is provided, comprising administering to the human a therapeutically effective amount of a compound disclosed herein in combination with a therapeutically effective amount of one or more (e.g., one, two, three, one or two, or one to three) additional therapeutic agents.

In some embodiments, the present invention provides a method for treating an Arenaviridae virus infection, comprising administering to a patient in need thereof a therapeutically effective amount of a compound or composition disclosed herein in combination with a therapeutically effective amount of one or more additional therapeutic agents which are suitable for treating an Arenaviridae virus infection. In some embodiments, the present invention provides a method for treating a Lassa virus infection, comprising administering to a patient in need thereof a therapeutically effective amount of a compound or composition disclosed herein in combination with a therapeutically effective amount of one or more additional therapeutic agents which are suitable for treating an Arenaviridae virus infection. In some embodiments, the present invention provides a method for treating a Lassa virus infection, comprising administering to a patient in need thereof a therapeutically effective amount of a compound or composition disclosed herein in combination with a therapeutically effective amount of one or more additional therapeutic agents which are suitable for treating a Lassa virus infection. In some embodiments, the present invention provides a method for treating a Junin virus infection, comprising administering to a patient in need thereof a therapeutically effective amount of a compound or composition disclosed herein in combination with a therapeutically effective amount of one or more additional therapeutic agents which are suitable for treating an Arenaviridae virus infection. In some embodiments, the present invention provides a method for treating a Junin virus infection, comprising administering to a patient in need thereof a therapeutically effective amount of a compound or composition disclosed herein in combination with a therapeutically effective amount of one or more additional therapeutic agents which are suitable for treating a Junin virus infection.

Some embodiments provide a compound disclosed herein in combination with one or more (e.g., one, two, three, one or two, or one to three) additional therapeutic agents for use in a method for treating an Arenaviridae virus infection in a human having the infection. Some embodiments provide a therapeutically effective amount of a compound disclosed herein in combination with therapeutically effective amount of one or more (e.g., one, two, three, one or two, or one to three) additional therapeutic agents for use in a method for treating a Lassa virus infection in a human having the infection. Some embodiments provide a therapeutically effective amount of a compound disclosed herein in combination with therapeutically effective amount of one or more (e.g., one, two, three, one or two, or one to three) additional therapeutic agents for use in a method for treating a Junin virus infection in a human having the infection. Some embodiments provide a therapeutically effective amount of a compound disclosed herein for use in a method for treating an Arenaviridae virus infection in a human having the infection, wherein the compound is administered in combination with therapeutically effective amount of one or more (e.g., one, two, three, one or two, or one to three) additional therapeutic agents. Some embodiments provide a compound disclosed herein for use in a method for treating a Lassa virus infection in a human having the infection, wherein a therapeutically effective amount of the compound is administered in combination with a therapeutically effective amount of one or more (e.g., one, two, three, one or two, or one to three) additional therapeutic agents. Some embodiments provide a compound disclosed herein for use in a method for treating a Junin virus infection in a human having the infection, wherein a therapeutically effective amount of the compound is administered in combination with a therapeutically effective amount of one or more (e.g., one, two, three, one or two, or one to three) additional therapeutic agents. In some embodiments, the present invention provides a compound disclosed herein in combination with one or more additional therapeutic agents which are suitable for treating an Arenaviridae virus infection, for use in a method for treating an Arenaviridae virus infection. In some embodiments, the present invention provides a compound disclosed herein for use in a method for treating an Arenaviridae virus infection, wherein a therapeutically effective amount of the compound is administered in combination with a therapeutically effective amount of one or more additional therapeutic agents which are suitable for treating an Arenaviridae virus infection. In some embodiments, the present invention provides a compound disclosed herein in combination with one or more additional therapeutic agents which are suitable for treating a Lassa virus infection, for use in a method for treating a Lassa virus infection. In some embodiments, the present invention provides a compound disclosed herein for use in a method for treating a Lassa virus infection, wherein a therapeutically effective amount of the compound is administered in combination with a therapeutically effective amount of one or more additional therapeutic agents which are suitable for treating a Lassa virus infection. In some embodiments, the present invention provides a compound disclosed herein in combination with one or more additional therapeutic agents which are suitable for treating a Junin virus infection, for use in a method for treating a Junin virus infection. In some embodiments, the present invention provides a compound disclosed herein for use in a method for treating a Junin virus infection, wherein a therapeutically effective amount of the compound is administered in combination with a therapeutically effective amount of one or more additional therapeutic agents which are suitable for treating a Junin virus infection.

In some embodiments, a method for treating a Coronaviridae virus infection in a human is provided, comprising administering to the human a therapeutically effective amount of a compound disclosed herein in combination with a therapeutically effective amount of one or more (e.g., one, two, three, one or two, or one to three) additional therapeutic agents. In some embodiments, a method for treating a SARS virus infection in a human is provided, comprising administering to the human a therapeutically effective amount of a compound disclosed herein in combination with a therapeutically effective amount of one or more (e.g., one, two, three, one or two, or one to three) additional therapeutic agents. In some embodiments, a method for treating a MERS virus infection in a human is provided, comprising administering to the human a therapeutically effective amount of a compound disclosed herein in combination with a therapeutically effective amount of one or more (e.g., one, two, three, one or two, or one to three) additional therapeutic agents.

In some embodiments, the present invention provides a method for treating a Coronaviridae virus infection, comprising administering to a patient in need thereof a therapeutically effective amount of a compound or composition disclosed herein in combination with a therapeutically effective amount of one or more additional therapeutic agents which are suitable for treating a Coronaviridae virus infection. In some embodiments, the present invention provides a method for treating a SARS virus infection, comprising administering to a patient in need thereof a therapeutically effective amount of a compound or composition disclosed herein in combination with a therapeutically effective amount of one or more additional therapeutic agents which are suitable for treating a Coronaviridae virus infection. In some embodiments, the present invention provides a method for treating a SARS virus infection, comprising administering to a patient in need thereof a therapeutically effective amount of a compound or composition disclosed herein in combination with a therapeutically effective amount of one or more additional therapeutic agents which are suitable for treating a SARS virus infection. In some embodiments, the present invention provides a method for treating a MERS virus infection, comprising administering to a patient in need thereof a therapeutically effective amount of a compound or composition disclosed herein in combination with a therapeutically effective amount of one or more additional therapeutic agents which are suitable for treating a Coronaviridae virus infection. In some embodiments, the present invention provides a method for treating a MERS virus infection, comprising administering to a patient in need thereof a therapeutically effective amount of a compound or composition disclosed herein in combination with a therapeutically effective amount of one or more additional therapeutic agents which are suitable for treating a MERS virus infection.

Some embodiments provide a compound disclosed herein in combination with one or more (e.g., one, two, three, one or two, or one to three) additional therapeutic agents for use in a method for treating a Coronaviridae virus infection in a human having the infection. Some embodiments provide a therapeutically effective amount of a compound disclosed herein in combination with therapeutically effective amount of one or more (e.g., one, two, three, one or two, or one to three) additional therapeutic agents for use in a method for treating a SARS virus infection in a human having the infection. Some embodiments provide a therapeutically effective amount of a compound disclosed herein in combination with therapeutically effective amount of one or more (e.g., one, two, three, one or two, or one to three) additional therapeutic agents for use in a method for treating a MERS virus infection in a human having the infection. Some embodiments provide a therapeutically effective amount of a compound disclosed herein for use in a method for treating a Coronaviridae virus infection in a human having the infection, wherein the compound is administered in combination with therapeutically effective amount of one or more (e.g., one, two, three, one or two, or one to three) additional therapeutic agents. Some embodiments provide a compound disclosed herein for use in a method for treating a SARS virus infection in a human having the infection, wherein a therapeutically effective amount of the compound is administered in combination with a therapeutically effective amount of one or more (e.g., one, two, three, one or two, or one to three) additional therapeutic agents. Some embodiments provide a compound disclosed herein for use in a method for treating a MERS virus infection in a human having the infection, wherein a therapeutically effective amount of the compound is administered in combination with a therapeutically effective amount of one or more (e.g., one, two, three, one or two, or one to three) additional therapeutic agents. In some embodiments, the present invention provides a compound disclosed herein in combination with one or more additional therapeutic agents which are suitable for treating a Coronaviridae virus infection, for use in a method for treating a Coronaviridae virus infection. In some embodiments, the present invention provides a compound disclosed herein for use in a method for treating a Coronaviridae virus infection, wherein a therapeutically effective amount of the compound is administered in combination with a therapeutically effective amount of one or more additional therapeutic agents which are suitable for treating a Coronaviridae virus infection. In some embodiments, the present invention provides a compound disclosed herein in combination with one or more additional therapeutic agents which are suitable for treating a SARS virus infection, for use in a method for treating a SARS virus infection. In some embodiments, the present invention provides a compound disclosed herein for use in a method for treating a SARS virus infection, wherein a therapeutically effective amount of the compound is administered in combination with a therapeutically effective amount of one or more additional therapeutic agents which are suitable for treating a SARS virus infection. In some embodiments, the present invention provides a compound disclosed herein in combination with one or more additional therapeutic agents which are suitable for treating a MERS virus infection, for use in a method for treating a MERS virus infection. In some embodiments, the present invention provides a compound disclosed herein for use in a method for treating a MERS virus infection, wherein a therapeutically effective amount of the compound is administered in combination with a therapeutically effective amount of one or more additional therapeutic agents which are suitable for treating a MERS virus infection.

In some embodiments, a method for treating a Filoviridae virus infection in a human is provided, comprising administering to the human a therapeutically effective amount of a compound disclosed herein in combination with a therapeutically effective amount of one or more (e.g., one, two, three, one or two, or one to three) additional therapeutic agents. In some embodiments, a method for treating an ebolavirus infection in a human is provided, comprising administering to the human a therapeutically effective amount of a compound disclosed herein in combination with a therapeutically effective amount of one or more (e.g., one, two, three, one or two, or one to three) additional therapeutic agents.

In some embodiments, the present invention provides a method for treating a Filoviridae virus infection, comprising administering to a patient in need thereof a therapeutically effective amount of a compound or composition disclosed herein in combination with a therapeutically effective amount of one or more additional therapeutic agents which are suitable for treating a Filoviridae virus infection. In some embodiments, the present invention provides a method for treating an ebolavirus infection, comprising administering to a patient in need thereof a therapeutically effective amount of a compound or composition disclosed herein in combination with a therapeutically effective amount of one or more additional therapeutic agents which are suitable for treating an ebolavirus infection.

Some embodiments provide a compound disclosed herein in combination with one or more (e.g., one, two, three, one or two, or one to three) additional therapeutic agents for use in a method for treating a Filoviridae virus infection in a human having the infection. Some embodiments provide a therapeutically effective amount of a compound disclosed herein in combination with therapeutically effective amount of one or more (e.g., one, two, three, one or two, or one to three) additional therapeutic agents for use in a method for treating an ebolavirus infection in a human having the infection. Some embodiments provide a therapeutically effective amount of a compound disclosed herein for use in a method for treating a Filoviridae virus infection in a human having the infection, wherein the compound is administered in combination with therapeutically effective amount of one or more (e.g., one, two, three, one or two, or one to three) additional therapeutic agents. Some embodiments provide a compound disclosed herein for use in a method for treating an ebolavirus infection in a human having the infection, wherein a therapeutically effective amount of the compound is administered in combination with a therapeutically effective amount of one or more (e.g., one, two, three, one or two, or one to three) additional therapeutic agents. In some embodiments, the present invention provides a compound disclosed herein in combination with one or more additional therapeutic agents which are suitable for treating a Filoviridae virus infection, for use in a method for treating a Filoviridae virus infection. In some embodiments, the present invention provides a compound disclosed herein for use in a method for treating a Filoviridae virus infection, wherein a therapeutically effective amount of the compound is administered in combination with a therapeutically effective amount of one or more additional therapeutic agents which are suitable for treating a Filoviridae virus infection.

In some embodiments, a method for treating a Flaviviridae virus infection in a human is provided, comprising administering to the human a therapeutically effective amount of a compound disclosed herein in combination with a therapeutically effective amount of one or more (e.g., one, two, three, one or two, or one to three) additional therapeutic agents. In some embodiments, a method for treating a Zika virus infection in a human is provided, comprising administering to the human a therapeutically effective amount of a compound disclosed herein in combination with a therapeutically effective amount of one or more (e.g., one, two, three, one or two, or one to three) additional therapeutic agents.

In some embodiments, the present invention provides a method for treating a Flaviviridae virus infection, comprising administering to a patient in need thereof a therapeutically effective amount of a compound or composition disclosed herein in combination with a therapeutically effective amount of one or more additional therapeutic agents which are suitable for treating a Flaviviridae virus infection. In some embodiments, the present invention provides a method for treating a Zika virus infection, comprising administering to a patient in need thereof a therapeutically effective amount of a compound or composition disclosed herein in combination with a therapeutically effective amount of one or more additional therapeutic agents which are suitable for treating a Zika virus infection.

Some embodiments provide a compound disclosed herein in combination with one or more (e.g., one, two, three, one or two, or one to three) additional therapeutic agents for use in a method for treating a Flaviviridae virus infection in a human having the infection. Some embodiments provide a therapeutically effective amount of a compound disclosed herein in combination with therapeutically effective amount of one or more (e.g., one, two, three, one or two, or one to three) additional therapeutic agents for use in a method for treating a Zika virus infection in a human having the infection. Some embodiments provide a therapeutically effective amount of a compound disclosed herein for use in a method for treating a Flaviviridae virus infection in a human having the infection, wherein the compound is administered in combination with therapeutically effective amount of one or more (e.g., one, two, three, one or two, or one to three) additional therapeutic agents. Some embodiments provide a compound disclosed herein for use in a method for treating a Zika virus infection in a human having the infection, wherein a therapeutically effective amount of the compound is administered in combination with a therapeutically effective amount of one or more (e.g., one, two, three, one or two, or one to three) additional therapeutic agents. In some embodiments, the present invention provides a compound disclosed herein in combination with one or more additional therapeutic agents which are suitable for treating a Flaviviridae virus infection, for use in a method for treating a Flaviviridae virus infection. In some embodiments, the present invention provides a compound disclosed herein for use in a method for treating a Flaviviridae virus infection, wherein a therapeutically effective amount of the compound is administered in combination with a therapeutically effective amount of one or more additional therapeutic agents which are suitable for treating a Flaviviridae virus infection.

In some embodiments, a method for treating a Paramyxoviridae virus infection in a human is provided, comprising administering to the human a therapeutically effective amount of a compound disclosed herein in combination with a therapeutically effective amount of one or more (e.g., one, two, three, one or two, or one to three) additional therapeutic agents. In some embodiments, a method for treating an RSV virus infection in a human is provided, comprising administering to the human a therapeutically effective amount of a compound disclosed herein in combination with a therapeutically effective amount of one or more (e.g., one, two, three, one or two, or one to three) additional therapeutic agents.

In some embodiments, the present invention provides a method for treating a Paramyxoviridae virus infection, comprising administering to a patient in need thereof a therapeutically effective amount of a compound or composition disclosed herein in combination with a therapeutically effective amount of one or more additional therapeutic agents which are suitable for treating a Paramyxoviridae virus infection. In some embodiments, the present invention provides a method for treating an RSV infection, comprising administering to a patient in need thereof a therapeutically effective amount of a compound or composition disclosed herein in combination with a therapeutically effective amount of one or more additional therapeutic agents which are suitable for treating a RSV infection.

Some embodiments provide a compound disclosed herein in combination with one or more (e.g., one, two, three, one or two, or one to three) additional therapeutic agents for use in a method for treating a Paramyxoviridae virus infection in a human having the infection. Some embodiments provide a therapeutically effective amount of a compound disclosed herein in combination with therapeutically effective amount of one or more (e.g., one, two, three, one or two, or one to three) additional therapeutic agents for use in a method for treating an RSV infection in a human having the infection. Some embodiments provide a therapeutically effective amount of a compound disclosed herein for use in a method for treating a Paramyxoviridae virus infection in a human having the infection, wherein the compound is administered in combination with therapeutically effective amount of one or more (e.g., one, two, three, one or two, or one to three) additional therapeutic agents. Some embodiments provide a compound disclosed herein for use in a method for treating an RSV infection in a human having the infection, wherein a therapeutically effective amount of the compound is administered in combination with a therapeutically effective amount of one or more (e.g., one, two, three, one or two, or one to three) additional therapeutic agents. In some embodiments, the present invention provides a compound disclosed herein in combination with one or more additional therapeutic agents which are suitable for treating a Paramyxoviridae virus infection, for use in a method for treating a Paramyxoviridae virus infection. In some embodiments, the present invention provides a compound disclosed herein for use in a method for treating a Paramyxoviridae virus infection, wherein a therapeutically effective amount of the compound is administered in combination with a therapeutically effective amount of one or more additional therapeutic agents which are suitable for treating a Paramyxoviridae virus infection.

A therapeutically effective amount of a compound of Formula I as disclosed herein may be combined with a therapeutically effective amount of one or more additional therapeutic agents in any dosage amount of the compound of Formula I (e.g., from 5 mg to 300 mg of compound).

In some embodiments, pharmaceutical compositions comprising a therapeutically effective amount of a compound disclosed herein in combination with a therapeutically effective amount of one or more (e.g., one, two, three, one or two, or one to three) additional therapeutic agents, and a pharmaceutically acceptable excipient are provided.

In some embodiments, combination pharmaceutical agents comprising a therapeutically effective amount of a compound disclosed herein in combination with a therapeutically effective amount of one or more (e.g., one, two, three, one or two, or one to three) additional therapeutic agents are provided.

In some embodiments, kits comprising a therapeutically effective amount of a compound disclosed herein in combination with a therapeutically effective amount of one or more (e.g., one, two, three, one or two, or one to three) additional therapeutic agents are provided.

In some embodiments, the additional therapeutic agent used in combination with a compound disclosed herein is active against virus infections.

In some embodiments, the additional therapeutic agent used in combination with a compound disclosed herein is active against Arenaviridae virus infections, particularly Lassa virus and Junin virus infections.

In some embodiments a therapeutically effective amount of a compound of Formula I is formulated as a solution, which may optionally contain a therapeutically effective amount of one or more other compounds useful for treating an Arenaviridae virus infection. In some embodiments, the solution can contain another active ingredient for treating an Arenaviridae virus infection.

In some embodiments, the additional therapeutic agent used in combination with a compound disclosed herein is active against Coronaviridae virus infections, particularly SARS virus and MERS virus infections.

In some embodiments a therapeutically effective amount of a compound of Formula I is formulated as a solution, which may optionally contain a therapeutically effective amount of one or more other compounds useful for treating a Coronaviridae virus infection. In some embodiments, the solution can contain another active ingredient for treating a Coronaviridae virus infection.

In some embodiments, the additional therapeutic agent used in combination with a compound disclosed herein is active against Filoviridae virus infections, particularly Marburg virus, ebolavirus and/or Cueva virus infections Non-limiting examples of these other active therapeutic agents are ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), and rVSV-EBOV, and mixtures thereof. The compounds and compositions of the present invention may also be used in combination with phosphoramidate morpholino oligomers (PMOs), which are synthetic antisense oligonucleotide analogs designed to interfere with translational processes by forming base-pair duplexes with specific RNA sequences. Examples of PMOs include AVI-7287, AVI-7288, AVI-7537, AVI-7539, AVI-6002, and AVI-6003. The compounds and compositions of the present invention are also intended for use with general care provided patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

In some embodiments a therapeutically effective amount of a compound of Formula I is formulated as a solution, which may optionally contain a therapeutically effective amount of one or more other compounds useful for treating a Filoviridae virus infection. In some embodiments, the solution can contain another active ingredient for treating a Filoviridae virus infection.

In some embodiments, the additional therapeutic agent used in combination with a compound disclosed herein is active against Flaviviridae virus infections, particularly Zika virus infections. Non-limiting examples of these other active therapeutic agents are amodiaquine, chloroquine, ribavirin, interferon α, BCX4430, NITD008, and monoclonal antibodies.

In some embodiments a therapeutically effective amount of a compound of Formula I is formulated as a solution, which may optionally contain a therapeutically effective amount of one or more other compounds useful for treating a Flaviviridae virus infection. In some embodiments, the solution can contain another active ingredient for treating a Flaviviridae virus infection.

In some embodiments, the additional therapeutic agent used in combination with a compound disclosed herein is active against Paramyxoviridae virus infections, particularly RSV infections. Non-limiting examples of these other active therapeutic agents are ribavirin, albuterol, epinephrine, and palivizumab.

In some embodiments a therapeutically effective amount of a compound of Formula I is formulated as a solution, which may optionally contain a therapeutically effective amount of one or more other compounds useful for treating a Paramyxoviridae virus infection. In some embodiments, the solution can contain another active ingredient for treating a Paramyxoviridae virus infection.

In some embodiments, when a compound disclosed herein is combined with one or more additional therapeutic agents as described above, the components of the composition are administered as a simultaneous or sequential regimen. When administered sequentially, the combination may be administered in two or more administrations.

In some embodiments, a therapeutically effective amount of a compound disclosed herein is combined with a therapeutically effective amount of one or more additional therapeutic agents in a unitary dosage form for simultaneous administration to a patient, for example as a solid dosage form for oral administration.

In some embodiments, a therapeutically effective amount of a compound disclosed herein is administered with one or more additional therapeutic agents. Co-administration of a therapeutically effective amount of a compound disclosed herein with a therapeutically effective amount of a one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient.

Co-administration includes administration of unit dosages comprising a therapeutically effective amount of one or more compounds disclosed herein before or after administration of unit dosages of a therapeutically effective amount of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

V. Methods of Treating

In some embodiments, the present invention is directed to methods of treating a virus selected from the group consisting of Arenaviridae, Coronaviridae, Filoviridae, Flaviviridae, and Paramyxoviridae.

In some embodiments, the present invention is directed to methods of treating an Arenaviridae virus infection by administering a compound of Formula I provided herein. In some embodiments, the present invention is directed to methods of treating an Arenaviridae species infections selected from the group of Allpahuayo virus (ALLV), Amapari virus (AMAV), Bear Canyon virus (BCNV), Catarina virus, Chapare virus, Cupixi virus (CPXV), Dandenong virus, Flexal virus (FLEV), Guanarito virus (GTOV), Ippy virus (IPPYV), Junin virus (JUNV), Kodoko virus, Lassa virus (LASV), Latino virus (LATV), Lymphocytic choriomeningitis virus (LCMV), Lujo virus, Machupo virus (MACV), Mobala virus (MOBV), Morogoro virus, Mopeia virus (MOPV), Oliveros virus (OLVV), Parana virus (PARV), Pichinde virus (PICV), Pinhal virus, Pirital virus (PIRV), Sabia virus (SABV), Skinner Tank virus, Tacaribe virus (TCRV), Tamiami virus (TAMV), and Whitewater Arroyo virus (WWAV) by administering a compound of Formula I provided herein. In some embodiments, the present invention is directed to methods of treating a Lassa virus infection by administering a compound of Formula I provided herein. In some embodiments, the present invention is directed to methods of treating a Junin virus infection by administering a compound of Formula I provided herein.

In some embodiments, the present invention is directed to methods of treating a Coronaviridae virus infection by administering a compound of Formula I provided herein. In some embodiments, the present invention is directed to methods of treating a Middle East Respiratory Syndrome (MERS) infection by administering a compound of Formula I provided herein. In some embodiments, the present invention is directed to methods of treating a Severe Acute Respiratory Syndrome (SARS) infection by administering a compound of Formula I provided herein.

In some embodiments, the present invention is directed to methods of treating a Filoviridae virus infection by administering a compound of Formula I provided herein. In some embodiments, the present invention is directed to methods of treating an ebolavirus infection by administering a compound of Formula I provided herein. In some embodiments, the present invention is directed to methods of treating an ebolavirus infection selected from the group consisting of: Zaire (i.e. Ebola virus, EBOV), Sudan, Tai Forest, Bundibugyo, and Reston; by administering a compound of Formula I provided herein. In some embodiments, the present invention is directed to methods of treating a Marburg virus infection by administering a compound of Formula I provided herein.

In some embodiments, the present invention is directed to methods of treating a Flaviviridae virus infection by administering a compound of Formula I provided herein. In some embodiments, the present invention is directed to methods of treating a Zika virus infection by administering a compound of Formula I provided herein.

In some embodiments, the present invention is directed to a compound of Formula I provided herein for use in methods of treating an Arenaviridae virus infection. In some embodiments, the present invention is directed to a compound of Formula I provided herein for use in methods of treating an Arenaviridae species infections selected from the group of Allpahuayo virus (ALLV), Amapari virus (AMAV), Bear Canyon virus (BCNV), Catarina virus, Chapare virus, Cupixi virus (CPXV), Dandenong virus, Flexal virus (FLEV), Guanarito virus (GTOV), Ippy virus (IPPYV), Junin virus (JUNV), Kodoko virus, Lassa virus (LASV), Latino virus (LATV), Lymphocytic choriomeningitis virus (LCMV), Lujo virus, Machupo virus (MACV), Mobala virus (MOBV), Morogoro virus, Mopeia virus (MOPV), Oliveros virus (OLVV), Parana virus (PARV), Pichinde virus (PICV), Pinhal virus, Pirital virus (PIRV), Sabia virus (SABV), Skinner Tank virus, Tacaribe virus (TCRV), Tamiami virus (TAMV), and Whitewater Arroyo virus (WWAV) by administering a compound of Formula I provided herein. In some embodiments, the present invention is directed to a compound of Formula I provided herein for use in methods of treating a Lassa virus infection. In some embodiments, the present invention is directed to a compound of Formula I provided herein for use in methods of treating a Junin virus infection.

In some embodiments, the present invention is directed to a compound of Formula I provided herein for use in methods of treating a Coronaviridae virus infection. In some embodiments, the present invention is directed to a compound of Formula I provided herein for use in methods of treating a Middle East Respiratory Syndrome (MERS) infection. In some embodiments, the present invention is directed to a compound of Formula I provided herein for use in methods of treating an Severe Acute Respiratory Syndrome (SARS) infection.

In some embodiments, the present invention is directed to a of Formula I provided herein for use in methods of treating a Filoviridae virus infection. In some embodiments, the present invention is directed to a of Formula I provided herein for use in methods of treating an ebolavirus infection. In some embodiments, the present invention is directed to a compound of Formula I provided herein for use in methods of treating an ebolavirus infection selected from the group consisting of: Zaire (i.e. Ebola virus, EBOV), Sudan, Tai Forest, Bundibugyo, and Reston. In some embodiments, the present invention is directed to a compound of Formula I provided herein for use in methods of treating a Marburg virus infection.

In some embodiments, the present invention is directed to a compound of Formula I provided herein for use in methods of treating a Flaviviridae virus infection. In some embodiments, the present invention is directed to a compound of Formula I provided herein for use in methods of treating a Zika virus infection.

In some embodiments, the present invention is directed to the use of a compound of Formula I provided herein in the manufacture of a medicament for treating an Arenaviridae virus infection. In some embodiments, the present invention is directed to the use of a compound of Formula I provided herein in the manufacture of a medicament for treating an Arenaviridae species infections selected from the group of: Allpahuayo virus (ALLV), Amapari virus (AMAV), Bear Canyon virus (BCNV), Catarina virus, Chapare virus, Cupixi virus (CPXV), Dandenong virus, Flexal virus (FLEV), Guanarito virus (GTOV), Ippy virus (IPPYV), Junin virus (JUNV), Kodoko virus, Lassa virus (LASV), Latino virus (LATV), Lymphocytic choriomeningitis virus (LCMV), Lujo virus, Machupo virus (MACV), Mobala virus (MOBV), Morogoro virus, Mopeia virus (MOPV), Oliveros virus (OLVV), Parana virus (PARV), Pichinde virus (PICV), Pinhal virus, Pirital virus (PIRV), Sabia virus (SABV), Skinner Tank virus, Tacaribe virus (TCRV), Tamiami virus (TAMV), and Whitewater Arroyo virus (WWAV). In some embodiments, the present invention is directed to the use of a compound of Formula I provided herein in the manufacture of a medicament for treating a Lassa virus infection. In some embodiments, the present invention is directed to the use of a compound of Formula I provided herein in the manufacture of a medicament for treating a Junin virus infection.

In some embodiments, the present invention is directed to the use of a compound of Formula I provided herein in the manufacture of a medicament for treating a Coronaviridae infection. In some embodiments, the present invention is directed to the use of a compound of Formula I provided herein in the manufacture of a medicament for treating a MERS infection. In some embodiments, the present invention is directed to the use of a compound of Formula I provided herein in the manufacture of a medicament for treating a SARS infection.

In some embodiments, the present invention is directed to the use of a compound of Formula I provided herein in the manufacture of a medicament for treating a Filoviridae virus infection. In some embodiments, the present invention is directed to the use of a compound of Formula I provided herein in the manufacture of a medicament for treating an ebolavirus infection. In some embodiments, the present invention is directed to the use of a compound of Formula I provided herein in the manufacture of a medicament for treating an ebolavirus infection selected from the group consisting of: Zaire (i.e. Ebola virus, EBOV), Sudan, Tai Forest, Bundibugyo, and Reston. In some embodiments, the present invention is directed to the use of a compound of Formula I provided herein in the manufacture of a medicament for treating a Marburg virus infection.

In some embodiments, the present invention is directed to the use of a compound of Formula I provided herein in the manufacture of a medicament for treating a Flaviviridae virus infection. In some embodiments, the present invention is directed to the use of a compound of Formula I provided herein in the manufacture of a medicament for treating a Zika virus infection.

VI. XRPD Data

In some embodiments, the crystalline forms are characterized by the interlattice plane intervals determined by an X-ray powder diffraction pattern (XRPD). The diffractogram of XRPD is typically represented by a diagram plotting the intensity of the peaks versus the location of the peaks, i.e., diffraction angle 2θ (two-theta) in degrees. The characteristic peaks of a given XRPD can be selected according to the peak locations and their relative intensity to conveniently distinguish this crystalline structure from others.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θ of about "8.7±0.3" denotes a range from about 8.7+0.3, i.e., about 9.0, to about 8.7-0.3, i.e., about 8.4. Depending on the sample preparation techniques, the calibration techniques applied to the instruments, human operational variation, and etc., those skilled in the art recognize that the appropriate error of margins for a XRPD can be ±0.5; ±0.4; ±0.3; ±0.2; ±0.1; ±0.05; or less. In some embodiments of the invention, the XRPD margin of error is ±0.2. In some embodiments of the invention, the XRPD margin of error is ±0.5.

Additional details of the methods and equipment used for the XRPD analysis are described in the Examples section.

The XRPD peaks for crystalline Formula I Form I are shown below in Table 1A.

TABLE 1A

XRPD peaks for crystalline Formula I Form I
Formula I
Form I

| Peak Position [°2θ] | Relative Intensity [%] |
|---|---|
| 5.3 | 100.0 |
| 20.6 | 98.5 |
| 17.6 | 74.8 |
| 16.3 | 68.1 |
| 13.7 | 67.3 |
| 21.0 | 63.3 |
| 22.1 | 61.8 |
| 17.1 | 61.0 |
| 10.7 | 49.7 |
| 14.3 | 44.0 |
| 21.3 | 38.0 |
| 12.9 | 32.3 |
| 19.2 | 30.0 |
| 25.7 | 25.4 |
| 8.6 | 25.2 |
| 22.7 | 24.8 |
| 25.4 | 22.8 |
| 24.0 | 21.3 |
| 19.5 | 17.6 |
| 27.0 | 15.5 |
| 20.0 | 15.1 |
| 23.3 | 14.7 |
| 28.7 | 13.5 |
| 29.0 | 13.4 |
| 32.1 | 8.1 |
| 32.7 | 8.1 |
| 34.8 | 7.7 |
| 11.1 | 6.5 |
| 31.3 | 5.1 |
| 35.7 | 4.5 |
| 30.5 | 4.0 |

The XRPD peaks for crystalline Formula I Form II are shown below in Table 1B.

TABLE 1B

XRPD peaks for crystalline Formula I Form II
Formula I
Form II

| Peak Position [°2θ] | Relative Intensity [%] |
|---|---|
| 22.3 | 100.0 |
| 16.2 | 66.8 |

TABLE 1B-continued

XRPD peaks for crystalline Formula I Form II
Formula I
Form II

| Peak Position [°2θ] | Relative Intensity [%] |
|---|---|
| 22.5 | 26.6 |
| 13.8 | 24.6 |
| 12.7 | 21.1 |
| 16.9 | 19.3 |
| 10.6 | 13.6 |
| 14.5 | 12.2 |
| 24.3 | 11.5 |
| 24.0 | 10.5 |
| 17.6 | 10.1 |
| 23.4 | 8.3 |
| 8.1 | 7.6 |
| 11.0 | 7.0 |
| 26.8 | 5.9 |
| 28.9 | 5.8 |
| 19.6 | 5.7 |
| 27.8 | 4.7 |
| 26.4 | 4.3 |
| 28.7 | 4.2 |
| 29.8 | 4.2 |
| 33.0 | 3.7 |
| 18.8 | 3.5 |
| 18.3 | 3.3 |
| 32.1 | 3.1 |
| 25.3 | 2.8 |
| 32.6 | 2.5 |
| 8.6 | 2.3 |
| 34.2 | 2.1 |
| 35.9 | 2.0 |
| 27.2 | 1.9 |
| 28.1 | 1.8 |
| 38.9 | 1.7 |
| 34.6 | 1.6 |
| 17.1 | 1.6 |
| 35.2 | 1.6 |
| 21.4 | 1.5 |
| 30.6 | 1.5 |
| 25.6 | 1.3 |
| 18.5 | 1.3 |
| 31.7 | 1.1 |
| 36.5 | 0.9 |
| 37.1 | 0.4 |

Calculated powder pattern peaks for crystalline Formula I Form III are shown below in Table 1C.

TABLE 1C

Calculated powder pattern peaks for crystalline
Formula I Form III
Formula I
Form III

| Peak Position [°2θ] | Relative Intensity [%] |
|---|---|
| 4.1 | 100.0 |
| 17.1 | 64.8 |
| 8.2 | 49.2 |
| 16.9 | 30.3 |
| 23.8 | 25.1 |
| 14.4 | 19.7 |
| 14.6 | 18.6 |
| 25.6 | 15.9 |
| 15.2 | 15.5 |
| 25.3 | 12.0 |
| 20.3 | 11.3 |
| 8.4 | 10.8 |
| 19.3 | 10.7 |
| 26.9 | 10.4 |
| 25.7 | 9.3 |
| 21.7 | 8.0 |

TABLE 1C-continued

Calculated powder pattern peaks for crystalline
Formula I Form III
Formula I
Form III

| Peak Position [°2θ] | Relative Intensity [%] |
|---|---|
| 24.2 | 7.8 |
| 22.5 | 6.9 |
| 28.1 | 6.9 |
| 20.6 | 6.7 |
| 16.5 | 6.3 |
| 24.4 | 5.7 |
| 21.9 | 5.1 |
| 21.1 | 5.0 |
| 36.1 | 4.9 |
| 32.2 | 4.3 |
| 9.1 | 3.9 |
| 21.3 | 3.3 |
| 18.4 | 3.3 |
| 28.4 | 3.0 |
| 12.0 | 2.8 |
| 36.4 | 2.7 |
| 33.4 | 2.6 |
| 28.9 | 2.6 |
| 35.2 | 2.3 |
| 33.2 | 2.3 |
| 31.4 | 2.2 |
| 37.2 | 2.1 |
| 36.9 | 2.1 |
| 32.1 | 2.1 |
| 24.8 | 1.9 |
| 30.5 | 1.9 |
| 19.0 | 1.8 |
| 33.1 | 1.8 |
| 22.3 | 1.8 |
| 32.6 | 1.7 |
| 27.5 | 1.7 |
| 31.8 | 1.5 |
| 29.3 | 1.5 |
| 39.2 | 1.4 |
| 25.0 | 1.4 |
| 26.5 | 1.4 |
| 26.1 | 1.3 |
| 29.1 | 1.3 |
| 39.4 | 1.2 |
| 18.8 | 1.1 |
| 34.6 | 0.9 |
| 29.5 | 0.8 |
| 12.6 | 0.7 |
| 35.7 | 0.6 |
| 34.0 | 0.6 |
| 38.3 | 0.6 |
| 30.2 | 0.5 |
| 37.7 | 0.4 |
| 23.0 | 0.3 |
| 29.7 | 0.3 |
| 11.5 | 0.2 |
| 5.4 | 0.1 |

The XRPD peaks for crystalline Formula I Form IV are shown below in Table 1D.

TABLE 1D

XRPD peaks for crystalline Formula I Form IV
Formula I
Form IV

| Peak Position [°2θ] | Relative Intensity [%] |
|---|---|
| 15.9 | 100 |
| 22.6 | 20.11 |
| 23.9 | 8.9 |
| 24.3 | 7.2 |
| 19.9 | 6.91 |

TABLE 1D-continued

XRPD peaks for crystalline Formula I Form IV
Formula I
Form IV

| Peak Position [°2θ] | Relative Intensity [%] |
|---|---|
| 14.1 | 6.59 |
| 24.9 | 5.84 |
| 16.3 | 5.7 |
| 17.4 | 5.42 |
| 7.9 | 5.04 |
| 32.0 | 3.84 |
| 12.5 | 3.12 |
| 23.0 | 2.97 |
| 10.6 | 2.5 |
| 16.6 | 2.5 |
| 32.8 | 2.42 |
| 28.3 | 2.23 |
| 26.5 | 2.17 |
| 29.1 | 1.88 |
| 14.9 | 1.61 |
| 27.3 | 1.24 |
| 20.8 | 1.03 |
| 11.3 | 0.97 |
| 19.2 | 0.58 |
| 39.2 | 0.39 |
| 34.8 | 0.35 |
| 36.0 | 0.32 |
| 30.2 | 0.3 |
| 36.8 | 0.29 |
| 33.8 | 0.24 |
| 31.2 | 0.16 |

The XRPD peaks for a mixture of Forms II and Form IV of Formula I (Mixture I) prepared by a process comprising combining Formula I with a solvent, wherein the solvent is isopropyl acetate are shown below in Table 1E.

TABLE 1E

XRPD peaks for a mixture of Forms II and Form IV of Formula I (Mixture I) prepared by a process comprising combining Formula I with a solvent, wherein the solvent is isopropyl acetate
Mixture I

| Peak Position [°2θ] | Relative Intensity [%] |
|---|---|
| 12.5 | 21.8 |
| 14.1 | 30.9 |
| 15.9 | 100.0 |
| 22.6 | 66.4 |

The XRPD peaks for a mixture of Forms II and Form IV of Formula I (Mixture II) prepared by a process comprising combining Formula I with a solvent, wherein the solvent is isopropyl acetate are below in Table 1F.

TABLE 1F

XRPD peaks for a mixture of Forms II and Form IV of Formula I (Mixture II) prepared by a process comprising combining Formula I with a solvent, wherein the solvent is isopropyl acetate.
Mixture II

| Peak Position [°2θ] | Relative Intensity [%] |
|---|---|
| 16.1 | 100.0 |
| 22.4 | 89.3 |
| 12.7 | 33.8 |
| 13.9 | 25.3 |
| 24.2 | 24.1 |
| 17.5 | 21.7 |
| 16.8 | 19.0 |

TABLE 1F-continued

XRPD peaks for a mixture of Forms II and Form IV of Formula I (Mixture II) prepared by a process comprising combining Formula I with a solvent, wherein the solvent is isopropyl acetate.
Mixture II

| Peak Position [°2θ] | Relative Intensity [%] |
|---|---|
| 11.1 | 17.3 |
| 10.7 | 16.8 |
| 14.7 | 14.3 |
| 19.8 | 9.8 |
| 8.1 | 7.6 |
| 25.1 | 6.2 |
| 28.8 | 6.1 |
| 26.5 | 6.1 |
| 21.0 | 5.5 |
| 18.9 | 5.1 |
| 29.9 | 5.0 |
| 32.3 | 4.3 |
| 8.7 | 3.0 |
| 33.3 | 3.0 |
| 34.5 | 2.9 |
| 27.9 | 1.7 |
| 36.2 | 1.0 |

The XRPD peaks for a mixture of Forms II and Form IV of Formula I (Mixture III) prepared by a process comprising combining Formula I with a solvent at a temperature, wherein the solvent is isopropyl alcohol and water and the temperature is 20° C. are below in Table 1G.

TABLE 1G

XRPD peaks for a mixture of Forms II and Form IV of Formula I (Mixture III) prepared by a process comprising combining Formula I with a solvent at a temperature, wherein the solvent is isopropyl alcohol and water and the temperature is 20° C.
Mixture III

| Peak Position [°2θ] | Relative Intensity [%] |
|---|---|
| 12.6 | 28.7 |
| 14.1 | 8.1 |
| 16.7 | 30.8 |
| 17.2 | 13.9 |
| 19.6 | 10.4 |

The XRPD peaks for crystalline Formula I Maleate Form I are below in Table 1H.

TABLE 1H

XRPD peaks for crystalline Formula I Form I Maleate
Formula I Maleate Form I

| Peak Position [°2θ] | Relative Intensity [%] |
|---|---|
| 7.3 | 100.0 |
| 9.0 | 99.1 |
| 17.8 | 69.0 |
| 15.1 | 67.4 |
| 14.7 | 54.7 |
| 22.0 | 54.6 |
| 18.6 | 53.9 |
| 19.1 | 42.3 |
| 25.7 | 39.6 |
| 6.2 | 38.8 |
| 4.6 | 37.8 |
| 12.4 | 37.8 |
| 20.3 | 34.4 |
| 13.3 | 32.1 |
| 9.9 | 31.3 |
| 16.3 | 27.3 |

TABLE 1H-continued

XRPD peaks for crystalline Formula I Form I Maleate
Formula I Maleate Form I

| Peak Position [°2θ] | Relative Intensity [%] |
|---|---|
| 23.9 | 26.5 |
| 23.0 | 23.3 |
| 21.1 | 18.4 |
| 11.2 | 12.8 |
| 29.3 | 12.0 |
| 27.4 | 11.8 |
| 28.2 | 11.0 |
| 31.5 | 4.7 |

VII. Preparation of the Crystalline Forms

A. Formula I

One method of synthesizing (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (e.g. a compound of Formula I) has been previously described in co-pending U.S. patent application Ser. No. 14/926,062, and related co-pending PCT patent application no. US2015/057933, filed Oct. 29, 2015 entitled "METHODS FOR TREATING FILOVIRIDAE VIRUS INFECTIONS." This reference is hereby incorporated herein by reference in its entirety, and specifically with respect to the synthesis of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate.

For example, in one aspect, provided is a method of producing a composition comprising one or more crystalline forms of Formula I, wherein the method comprises combining a compound of Formula I with a suitable solvent or a mixture of suitable solvents to produce a composition comprising one or more crystalline forms of the compound of Formula I. In another aspect, provided is another method of producing a composition comprising one or more crystalline forms of Formula I, wherein the method comprises combining Formula I with a suitable solvent or a mixture of suitable solvents.

The choice of a particular solvent or combination of solvents or method of combining solvents affects the formation favoring one crystalline form of Formula I over another. Solvents suitable for crystal formation may include, for example, water, isopropyl ether, isopropyl acetate, isopropyl alcohol, ethanol, dichloromethane, 2-methyltetrahydrofuran, methyl tert-butyl ether, heptane, acetonitrile, and any mixtures thereof.

The presence of impurities affects the formation favoring one crystalline form of Formula I over another. In some embodiments, the form is prepared by a process comprising Formula I having impurities. In another embodiment, the form is prepared by a process comprising substantially pure Formula I.

In another aspect, provided is also one or more crystalline forms of Formula I produced according to any of the methods described herein.

It should be understood that the methods for preparing the crystalline forms described herein (including any one or more of crystalline Forms I to IV and/or Mixtures I, II, and/or III) may yield quantity and quality differences compared to the methods for preparing Formula I produced on laboratory scale.

Formula I Form I

In some embodiments, provided is a method of producing a composition comprising crystalline Form I, wherein the method comprises combining Formula I with a solvent to produce a composition comprising crystalline Formula I Form I, wherein the solvent is isopropyl ether.

Provided is crystalline Formula I Form I produced by combining Formula I with a solvent, wherein the solvent is isopropyl ether.

Formula I Form II

In some embodiments, provided is a method of producing a composition comprising crystalline Formula I Form II, wherein the method comprises combining Formula I with a solvent to produce a composition comprising crystalline Formula I Form II, wherein the solvent is ethanol and water.

Provided is crystalline Formula I Form II produced by combining Formula I with a solvent, wherein the solvent is ethanol and water.

In some embodiments, provided is a method of producing a composition comprising crystalline Formula I Form II, wherein the method comprises combining Formula I with a solvent at a temperature to produce a composition comprising crystalline Formula I Form II, wherein the solvent is isopropyl alcohol and water and the temperature is 50° C.

Provided is crystalline Formula I Form II produced by combining Formula I with a solvent at a temperature, wherein the solvent is isopropyl alcohol and water and the temperature is 50° C.

In some embodiments, provided is a method of producing crystalline Formula I Form II by contacting Formula I of the invention and a solvent mixture of isopropanol and water, wherein Formula I remains substantially insoluble in the solvent mixture, under conditions suitable to prepare crystalline Formula I Form II. Formula I used in the method of the present invention can be crystalline Formula I, such as crystalline Form I, crystalline Form II, crystalline Form III, crystalline Form IV, or mixtures thereof, such as Mixture I, Mixture II or Mixture III. In some embodiments, Formula I can be crystalline Formula I. In some embodiments, Formula I can be a mixture of Formula I Form II and Formula I Form IV. In some embodiments, Formula I can be Mixture I, Mixture II or Mixture III. In some embodiments, Formula I can be Mixture II. In some embodiments, Form II is prepared substantially free of Form IV. In some embodiments, Formula I includes a mixture of Form II and Form IV, the solvent mixture includes isopropanol and water, wherein Formula I remains substantially insoluble in the solvent mixture, thereby preparing crystalline Form II substantially free of crystalline Form IV.

The isopropanol and water can be present in the solvent mixture in any suitable ratio where the volume of water is at least as great as the volume of isopropanol. Representative ratios of the isopropanol and water include from 1:1 to about 1:5 (V/V), or from 1:1 to about 1:4 (V/V), or from 1:1 to about 1:3 (V/V), or from 1:1 to about 1:2 (V/V), or from about 1:1.5 to about 1:2 (V/V). Representative ratios of the isopropanol and water include at least 1:1 (V/V), as well as 1:1.1, 1:1.2, 1:1.3, 1:1.4, 1:1.5, 1:1.6, 1:1.7, 1:1.8, 1:1.9, 1:2, 1:2.5, 1:3, 1:4, or 1:5 (V/V). Other ratios of the isopropanol and water include 2:2, 2:3, 2:4, 2:5, 2:6, 2:7, 2:8, 2:9, 2:10, 3:3, 3:4, 3:5, 3:6, 3:7, 3:8, 3:9 or 3:10 (V/V). In some embodiments, the solvent mixture includes isopropanol and water in a ratio of from 1:1 to about 1:2 (V/V). In some embodiments, the solvent mixture includes isopropanol and water in a ratio of from about 2:3 to about 1:2 (V/V). In some embodiments, the solvent mixture includes isopropanol and water in a ratio of at least 1:1 (V/V), wherein the water is present in a volume not less than the volume of isopropanol. In some embodiments, the solvent mixture includes isopropanol and water in a ratio of about 3:4 (V/V). In some embodiments, the solvent mixture includes isopropanol and water in a ratio of about 3:5 (V/V). In some embodiments, the solvent mixture includes isopropanol and water in a ratio of about 1:2 (V/V).

The method of making crystalline Formula I Form II can be performed at any suitable temperature. Representative temperatures for preparation of crystalline Formula I Form II about 20° C., or 25, 30, 35, 40, 45, 50, 51, 52, 53, 54, 55, 56, 57, 58, 59, 60, 65, 70, 75 or about 80° C. Representative temperatures ranges include 20° C. to 80° C., or 25° C. to 70° C., 30° C. to 60° C., 40° C. to 60° C., 45° C. to 60° C., or 45° C. to 55° C. In some embodiments, the contacting step is performed at a temperature of from about 30° C. to about 60° C. In some embodiments, the contacting step is performed at a temperature of from about 45° C. to about 60° C. In some embodiments, the contacting step is performed at a temperature of about 50° C.

In some embodiments, the contacting step is performed at a temperature of from about 30° C. to about 60° C. wherein the solvent mixture includes isopropanol and water in a ratio of at least 1:1 (V/V), wherein the water is present in a volume not less than the volume of isopropanol. In some embodiments, the contacting step is performed at a temperature of from about 45° C. to about 60° C. wherein the solvent mixture includes isopropanol and water in a ratio of from 1:1 to about 1:3 (V/V). In some embodiments, the contacting step is performed at a temperature of from about 45° C. to about 60° C. wherein the solvent mixture includes isopropanol and water in a ratio of from about 2:3 to about 2:5 (V/V). In some embodiments, the contacting step is performed at a temperature of from about 45° C. to about 60° C. wherein the solvent mixture includes isopropanol and water in a ratio of about 3:4 (V/V). In some embodiments, the contacting step is performed at a temperature of from about 45° C. to about 60° C. wherein the solvent mixture includes isopropanol and water in a ratio of about 3:5 (V/V). In some embodiments, the contacting step is performed at a temperature of about 50° C. wherein the solvent mixture includes isopropanol and water in a ratio of about 1:2 (V/V).

In some embodiments, the crystalline Form II is prepared substantially free of Form IV. In some embodiments, the Mixture II comprises Formula I Form II and Formula I Form IV, such that the crystalline Form II is prepared substantially free of Formula I Form IV.

In some embodiments, provided is a method of producing crystalline Form II, comprising contacting Formula I and a solvent mixture, wherein Formula I comprises Form II and Form IV, wherein the solvent mixture comprises isopropanol and water in a ratio of about 3:5 (V/V) and is at a temperature of about 50° C., and wherein Formula I remains substantially insoluble in the solvent mixture, thereby preparing crystalline Form II substantially free of crystalline Form IV.

In some embodiments, provided is a method of producing a composition comprising crystalline Formula I Form II, wherein the method comprises combining Formula I with a solvent to produce a composition comprising crystalline Formula I Form II, wherein the solvent is 1-propanol.

Provided is crystalline Formula I Form II produced by combining Formula I with a solvent, wherein the solvent is 1-propanol.

In some embodiments, provided is a method of producing a composition comprising crystalline Formula I Form II, wherein the method comprises combining Formula I with a solvent to produce a composition comprising crystalline Formula I Form II, wherein the solvent is tetrahydrofuran.

Provided is crystalline Formula I Form II produced by combining Formula I with a solvent, wherein the solvent is tetrahydrofuran.

In some embodiments, provided is a method of producing a composition comprising crystalline Formula I Form II, wherein the method comprises combining Formula I with a solvent to produce a composition comprising crystalline Formula I Form II, wherein the solvent is 2-propanol.

Provided is crystalline Formula I Form II produced by combining Formula I with a solvent, wherein the solvent is 2-propanol.

In some embodiments, provided is a method of producing a composition comprising crystalline Formula I Form II, wherein the method comprises combining Formula I with a solvent to produce a composition comprising crystalline Formula I Form II, wherein the solvent is acetonitrile.

Provided is crystalline Formula I Form II produced by combining Formula I with a solvent, wherein the solvent is acetonitrile.

In some embodiments, provided is a method of producing a composition comprising crystalline Formula I Form II, wherein the method comprises combining Formula I with a solvent to produce a composition comprising crystalline Formula I Form II, wherein the solvent is dichloromethane.

Provided is crystalline Formula I Form II produced by combining Formula I with a solvent, wherein the solvent is dichloromethane.

In some embodiments, provided is a method of producing a composition comprising crystalline Formula I Form II, wherein the method comprises combining Formula I with a solvent to produce a composition comprising crystalline Formula I Form II, wherein the solvent is ethanol.

Provided is crystalline Formula I Form II produced by combining Formula I with a solvent, wherein the solvent is ethanol.

In some embodiments, provided is a method of producing a composition comprising crystalline Formula I Form II, wherein the method comprises combining Formula I with a solvent to produce a composition comprising crystalline Formula I Form II, wherein the solvent is methyl tert-butyl ether.

Provided is crystalline Formula I Form II produced by combining Formula I with a solvent, wherein the solvent is methyl tert-butyl ether.

In some embodiments, provided is a method of producing a composition comprising crystalline Formula I Form II, wherein the method comprises combining Formula I with a solvent to produce a composition comprising crystalline Formula I Form II, wherein the solvent is 2-methytetrahydrofuran.

Provided is crystalline Formula I Form II produced by combining Formula I with a solvent, wherein the solvent is 2-methytetrahydrofuran.

In some embodiments, provided is a method of producing a composition comprising crystalline Formula I Form II, wherein the method comprises combining Formula I with a solvent to produce a composition comprising crystalline Formula I Form II, wherein the solvent is ethyl acetate and water.

Provided is crystalline Formula I Form II produced by combining Formula I with a solvent, wherein the solvent is ethyl acetate and water.

In some embodiments, provided is a method of producing a composition comprising crystalline Formula I Form II, wherein the method comprises combining Formula I with a solvent to produce a composition comprising crystalline Formula I Form II, wherein the solvent is methyl ethyl ketone.

Provided is crystalline Formula I Form II produced by combining Formula I with a solvent, wherein the solvent is methyl ethyl ketone.

Formula I Form III

In some embodiments, provided is a method of producing a composition comprising crystalline Form III, wherein the method comprises combining Formula I with a solvent to produce a composition comprising crystalline Form III, wherein the solvent is dichloromethane.

Provided is crystalline Form III produced by combining Formula I with a solvent, wherein the solvent is dichloromethane.

Formula I Form IV

In some embodiments, provided is a method of producing a composition comprising crystalline Formula I Form IV, wherein the method comprises combining Formula I with a solvent to produce a composition comprising crystalline Formula I Form IV, wherein the solvent is 2-methyltetrahydrofuran and methyl tert-butyl ether.

Provided is crystalline Formula I Form IV produced by combining Formula I with a solvent, wherein the solvent is 2-methyltetrahydrofuran and methyl tert-butyl ether.

In some embodiments, provided is a method of producing a composition comprising crystalline Formula I Form IV, wherein the method comprises combining Formula I with a solvent to produce a composition comprising crystalline Formula I Form IV, wherein the solvent is 2-methyltetrahydrofuran and heptane.

Provided is crystalline Formula I Form IV produced by combining Formula I with a solvent, wherein the solvent is 2-methyltetrahydrofuran and heptane.

B. Mixtures of Forms of Formula I

In some embodiments, the present invention is directed to a mixture of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate crystalline forms (Formula I Mixture).

In some embodiments, the present invention is directed to a mixture of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form II and (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form IV.

In some embodiments, the present invention is directed to a mixture of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate crystalline forms prepared by a process comprising combining Formula I with a solvent, wherein the solvent is selected from isopropyl acetate and mixtures of isopropyl alcohol and water. In some embodiments, the present invention is directed to a mixture of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form II and (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form IV prepared by a process comprising combining Formula I with a solvent, wherein the solvent is isopropyl acetate and isopropyl alcohol. In some embodiments, the present invention is directed to a mixture of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form II and (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form IV prepared by a process comprising combining Formula I with a solvent, wherein the solvent is isopropyl acetate. In some embodiments, the present invention is directed to a mixture of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form II and (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate Form IV prepared by a process comprising combining Formula I with a solvent, wherein the solvent is a mixture of isopropyl alcohol and water.

Mixtures of Form II and Form IV of Formula I can be prepared by using a variety of solvents or mixtures thereof. Representative solvents include, but are not limited to, water, isopropanol (IPA), isoproyl acetate (IPAc), tetrahydrofuran (THF), 2-methyltetrahydrofuran (MeTHF), methyl t-butyl ether (MTBE), and combinations thereof. Mixtures of Form II and Form IV can result in Form II and Form IV being present in different amounts. Representative mixtures of Form II and Form IV include Mixture I, Mixture II and Mixture III, among others.

In some embodiments, provided is a method of producing a mixture of Form II and Form IV, wherein the method comprises combining Formula I with a solvent, wherein the solvent is isopropyl acetate.

Provided is a mixture of Form II and Form IV produced by combining Formula I with a solvent, wherein the solvent is isopropyl acetate. Provided is a mixture of Form II and Form IV produced by combining Formula I with a solvent, wherein the solvent is a mixture of isopropyl alcohol and water. Provided is a mixture of Form II and Form IV produced by combining Formula I with a solvent, wherein the solvent is a mixture of 2-methyltetrahydrofuran and methyl t-butyl ether.

When the solvent includes a mixture of solvents, the solvent mixture can include a solvent suitable for dissolving the starting material and an antisolvent that is substantially unable to dissolve the starting material. The solvent and antisolvent can be present in any suitable ratio. Representative ratios of the solvent and antisolvent include from 10:1 to 1:10, or 5:1 to 1:5, 4:1 to 1:4, 3:1 to 1:3, or 2:1 to 1:2 (V/V). The ratio of solvent to antisolvent can also change during the crystallization process, such as by starting at a ratio of solvent to antisolvent of 10:1, 9:1, 8:1, 7:1, 6:1, 5:1, 4:1, 3:1 or 2:1, and then adding additional antisolvent to change the ratio of solvent to antisolvent to 1:2, 1:3, 1:4, 1:5, 1:6, 1:7, 1:8, 1:9 or 1:10. In some embodiments, the initial ratio of solvent to antisolvent can be about 3:1 (V/V), and the final ratio of solvent to antisolvent can be about 1:2 (V/V). In some embodiments, the initial ratio of isopropyl alcohol to water can be about 3:1 (V/V), and the final ratio can be about 1:2 (V/V). In some embodiments, the initial ratio of solvent to antisolvent can be about 8:1 (V/V), and the final ratio of solvent to antisolvent can be about 1:2 (V/V). In some embodiments, the initial ratio of 2-methyltetrahydrofuran (MeTHF) to methyl t-butylether (MTBE) can be about 8:1 (V/V), and the final ratio can be about 1:2 (V/V).

Mixture I

In some embodiments, provided is a method of producing Mixture I wherein the method comprises combining Formula I with a solvent, wherein the solvent is isopropyl acetate.

Provided is Mixture I produced by combining Formula I with a solvent, wherein the solvent is isopropyl acetate.

Mixture II

In some embodiments, provided is a method of producing Mixture II, wherein the method comprises combining Formula I with a solvent, wherein the solvent is isopropyl acetate.

Provided is Mixture II produced by combining Formula I with a solvent, wherein the solvent is isopropyl acetate.

Mixture III

In some embodiments, provided is a method of producing Mixture III, wherein the method comprises combining Formula I with a solvent at a temperature, wherein the solvent is isopropyl alcohol and water and the temperature is about 20° C.

Provided is Mixture III produced by combining Formula I with a solvent at a temperature, wherein the solvent is isopropyl alcohol and water and the temperature is about 20° C.

C. Formula I Maleate

In some embodiments, provided is a method of producing a composition comprising crystalline Formula I Maleate Form I, wherein the method comprises combining Formula I with maleic acid in a solvent to produce a composition comprising crystalline Formula I Maleate Form I, wherein the solvent is methanol and isopropyl acetate.

Provided is Formula I Maleate Form I produced by combining Formula I with maleic acid in a solvent to produce a composition comprising crystalline Formula I Maleate, wherein the solvent is methanol and isopropyl acetate.

VIII. Uses in Manufacturing of Drug Product

Provided are also a use of the crystalline forms described herein in the manufacture of a drug product. The one or more of the compounds of Formula I described herein may be used as an intermediate in the manufacturing process to produce the drug product.

In some embodiments, a compound of Formula I is used in the manufacture of an active pharmaceutical ingredient. In some embodiments, Formula I Form I is used in the manufacture of an active pharmaceutical ingredient. In some embodiments, Formula I Form II is used in the manufacture of an active pharmaceutical ingredient. In some embodiments, Formula I Form III is used in the manufacture of an active pharmaceutical ingredient. In some embodiments, Formula I Form IV is used in the manufacture of an active pharmaceutical ingredient. In some embodiments, a mixture of forms of Formula I is used in the manufacture of an active pharmaceutical ingredient. In some embodiments, a mixture of Formula I Form II and Formula I Form IV is used in the manufacture of an active pharmaceutical ingredient. In some embodiments, Mixture I is used in the manufacture of an active pharmaceutical ingredient. In some embodiments, Mixture II is used in the manufacture of an active pharmaceutical ingredient. In some embodiments, Mixture III is used in the manufacture of an active pharmaceutical ingredient. In some embodiments, Formula I Maleate Form I is used in the manufacture of an active pharmaceutical ingredient.

IX. Articles of Manufacture and Kits

Compositions comprising one or more of the compounds of Formula I described herein and formulated in one or more pharmaceutically acceptable excipients or other ingredients can be prepared, placed in an appropriate container, and labeled for treatment of an indicated condition. Accordingly, there also is contemplated an article of manufacture, such as a container comprising a dosage form of one or more of the compounds of Formula I described herein and a label containing instructions for use of the compound(s).

In some embodiments, the article of manufacture is a container comprising a dosage form of one or more of the compounds of Formula I described herein, and one or more pharmaceutically acceptable excipients or other ingredients. In some embodiments of the articles of manufacture described herein, the dosage form is a solution.

Kits also are contemplated. For example, a kit can comprise a dosage form of a pharmaceutical composition and a package insert containing instructions for use of the composition in treatment of a medical condition. In another embodiment a kit may comprise multiple individual dosage forms, each comprising a therapeutically effective amount of a compound as described herein, and instructions for their administration to a human in need thereof. Each of the individual dosage forms may comprise a therapeutically effective amount of a compound as described herein in combination with at least one pharmaceutically effective excipient. The individual dosage forms may be in the form of, as examples, a solution, a tablet, a pill, a capsule, a sachet, a sublingual medicament, a lyophilized powder, a spray-dried powder, or a liquid composition for oral, parenteral, or topical administration. The instructions for use in the kit may be for treating an Arenaviridae virus infection, a Coronaviridae virus infection, a Filoviridae virus infection, a Flaviviridae virus infection, or a Paramyxoviridae virus infection, including the species of each described herein. In some embodiments, the instructions for use in the kit may be for treating a Lassa virus infection in a human. In some embodiments, the instructions for use in the kit may be for treating a Junin virus infection in a human. In some embodiments, the instructions for use in the kit may be for treating a SARS virus infection in a human. In some embodiments, the instructions for use in the kit may be for treating a MERS virus infection in a human. In some embodiments, the instructions for use in the kit may be for treating an ebolavirus infection in a human. In some embodiments, the instructions for use in the kit may be for treating a Zika virus infection in a human. In some embodiments, the instructions for use in the kit may be for treating an RSV infection in a human. The instructions may be directed to any of the viral infections and methods described herein. The instructions may be for prophylaxis or the treatment of an existing viral infection.

In some embodiments, the crystalline or salt forms described herein may potentially exhibit improved properties. For example, In some embodiments, the crystalline or salt forms described herein may potentially exhibit improved stability. Such improved stability could have a potentially beneficial impact on the manufacture of the compound of Formula I, such as for example offering the ability to store process intermediate for extended periods of time. Improved stability could also potentially benefit a composition or pharmaceutical composition of the compound of Formula I. In some embodiments, the crystalline or salt described herein may also potentially result in improved yield of the compound of Formula I, or potentially result in an improvement of the quality of the compound of Formula I. In some embodiments, the crystalline, salt and solvate forms described herein may also exhibit improved pharmacokinetic properties and/or potentially improved bioavailability.

X. Methods

Example 1. Formula I Form I

Formula I (56.2 mg) was added to a glass vial. Isopropyl ether (about 0.5 mL) was added, the vial was capped, and the suspension was stirred at about 21° C. for about 4 days. Formula I Form I was isolated as a solid from the suspension by centrifuge/filtration and characterized as discussed below.

Example 2. Formula I Form II

Formula I (0.03 to 0.07 g) was added to a reaction vessel and dosed with about 0.1 to 0.4 g of ethanol and water mixtures with water activity ranging from 0.2 to 0.8. The vessel was sealed and agitated for about two weeks at room temperature. Formula I Form II was isolated and characterized as discussed below.

In an alternative method, Formula I (3.7 g) was added to a reaction vessel. Isopropyl alcohol (about 11 mL) and water (about 4 mL) were added and the suspension was heated to about 50° C. until dissolution was achieved. Water (about 2 mL) was added over about 1 hour at about 50° C., and then about 37 mg of Formula I Form II seeds were added. Water (about 6 mL) was added over about 2.5 hours at about 50° C., and the suspension was stirred at about 50° C. for about 1.5 hours. Water (about 11 mL) was added over about 6 hours, and the suspension was stirred at about 50° C. for about 9 hours. The suspension was cooled to about 20° C. over about 6 hours, and the suspension was stirred at about 20° C. for about 17 hours. Formula I Form II was isolated as a solid from the suspension by filtration and characterized as discussed below.

In an alternative method, crystalline Formula I (7.0 g) was added to a reaction vessel. Isopropyl alcohol (about 21 mL) and water (about 35 mL) were added and the suspension was heated to about 50° C. The suspension was stirred at about 50° C. for about 18 hours, and was then cooled to about 20° C. over about 3 hours, and stirred at about 20° C. for about 3 hours. Formula I Form II was isolated as a solid from the suspension by filtration and characterized as discussed below.

Example 3. Formula I Form III

Formula I (41.2 mg) was dissolved in a flask with dichloromethane (97.9 mg) at about 21° C. The flask was capped for a few days. Formula I Form III was observed.

Example 4. Formula I Form IV

MeTHF/MTBE

A crude solution of Formula I (8.0 g) in 2-methyltetrahydrofuran (32 mL) was stirred in a reaction vessel at about 20° C., and methyl tert-butyl ether (4 mL) was added over about 1 hour. Seeds containing a mixture of Form II and Form IV were added and the suspension was stirred at about 20° C. Methyl tert-butyl ether (64 mL) was added over the period of about 5 days at about 20° C., and the suspension was stirred at about 20° C. for 2 days. Formula I Form IV was isolated as a solid from the suspension by filtration and dried.

MeTHF/MTBE

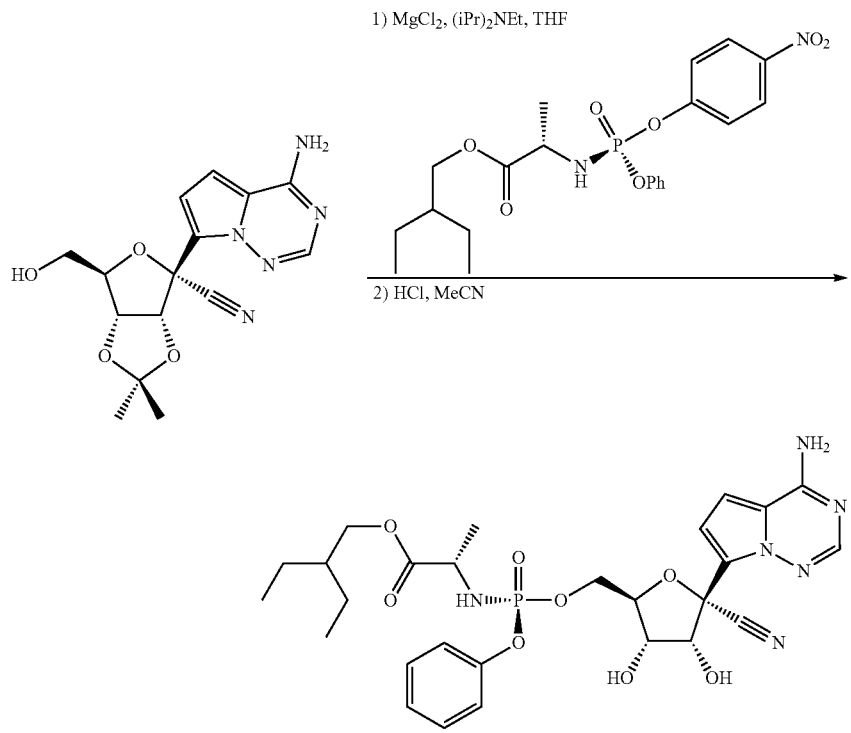

(3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (10 g, 30 mmol), 2-ethylbutyl ((S)-(4-nitrophenoxy)(phenoxy)phosphoryl)-L-alaninate (14 g, 32 mmol), and magnesium chloride (4.4 g, 46 mmol) were added to a reaction vessel. Tetrahydrofuran (about 100 mL) was added, followed by the addition of N,N-diisopropylethylamine (13 mL, 76 mmol) at about 25° C. After about 3 h, the reaction mixture was charged into a pre-cooled (about 10° C.) mixture of methyl tert-butyl ether (about 100 mL) and aqueous citric acid (10 wt %, about 100 mL). The organic and aqueous layers were separated, and the organic layer was washed with aqueous potassium carbonate (10 wt %, about 150 mL), aqueous potassium carbonate (10 wt %, two times about 100 mL), aqueous ammonium chloride (10 wt %, about 100 mL), and aqueous sodium chloride (15 wt %, about 100 mL). The solvent of the organic layer was exchanged to acetonitrile and the volume was adjusted to about 100 mL. The acetonitrile solution was cooled to about 0° C. and concentrated hydrochloric acid (about 20 mL) was added. After about 3 h, the reaction mixture was charged into a precooled (about 10° C.) mixture of 2-methyltetrahydrofuran (about 100 mL) and aqueous potassium bicarbonate (20 wt %, about 100 mL), and rinsed forward with 2-methyltetrahydrofuran (about 50 mL). The organic and aqueous layers were separated, and the organic layer was washed with aqueous potassium bicarbonate (20 wt %, about 40 mL), and aqueous sodium chloride (15 wt %, about 100 mL). The organic layer was concentrated to about 50 mL, and 2-methyltetrahydrofuran (about 50 mL) was charged. The organic layer was then washed with aqueous sodium chloride (15 wt %, about 50 mL). The organic layer was concentrated and distilled from 2-methyltetrahydrofuran until the solution reached a target water content of no more than 0.2%. The 2-methyltetrahydrofuran solution (about 200 mL) was polish filtered and a portion (about a third) of the 2-methyltetrahydrofuran solution was then concentrated to about 23 mL. Formula I Form IV seeds (about 40 mg) were added at about 20° C., and methyl tert-butyl ether (about 43 mL) was added over about 8 h. The suspension was stirred at about 20° C. for about a week. Formula I Form IV was isolated as a solid from the suspension by filtration and characterized as discussed below.

MeTHF/Heptane

In an alternative method, (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (3.0 g, 9.0 mmol), 2-ethylbutyl ((S)-(4-nitrophenoxy)(phenoxy)phosphoryl)-L-alaninate (4.3 g, 9.5 mmol), and magnesium chloride (1.3 g, 14 mmol) were added to a reaction vessel. Tetrahydrofuran (about 30 mL) was added, followed by the addition of N,N-diisopropylethylamine (3.9 mL, 23 mmol) at about 25° C. After about 16 h, the reaction mixture was charged into a pre-cooled (about 3° C.) mixture of 2-methyltetrahydrofuran (about 30 mL) and aqueous citric acid (10 wt %, about 30 mL). The organic and aqueous layers were separated, and the organic layer was washed with aqueous potassium carbonate (10 wt %, about 45 mL), aqueous potassium carbonate (10 wt %, two times about 30 mL), and aqueous ammonium chloride (10 wt %, about 30 mL). The solvent of the organic layer was exchanged to acetonitrile and the volume was adjusted to about 32 mL. The acetonitrile solution was cooled to about 0° C. and concentrated hydrochloric acid (about 6 mL) was added. After about 2 h, the reaction mixture was charged into a precooled (about 12° C.) mixture of 2-methyltetrahydrofuran (about 30 mL) and aqueous potassium bicarbonate (20 wt %, about 30 mL). The organic and aqueous layers were separated, and the organic layer was washed with aqueous potassium bicarbonate (20 wt %, about 12 mL), and aqueous sodium chloride (15 wt %, about 30 mL). The organic layer was concentrated to about 12 mL and 2-methyltetrahydrofuran (about 15 mL) was charged. The organic layer was then washed with aqueous sodium chloride (15 wt %, about 15 mL). The organic layer was concentrated and distilled from 2-methyltetrahydrofuran until the solution reached a target water content of no more than 0.2%. The 2-methyltetrahydrofuran solution (about 60 mL) was polish filtered and then concentrated to about 24 mL, and the solution was stirred at about 20° C. Seeds containing a mixture of Form II and Form IV (about 30 mg) were added, and heptane (about 18 mL) was slowly charged to the suspension. The suspension was stirred at about 21° C. for about 1 day, and then after about 2 weeks, Formula I Form IV was isolated as a solid from the suspension by filtration and characterized as discussed below.

Example 5. Mixture I, A Mixture of Form II and Form IV

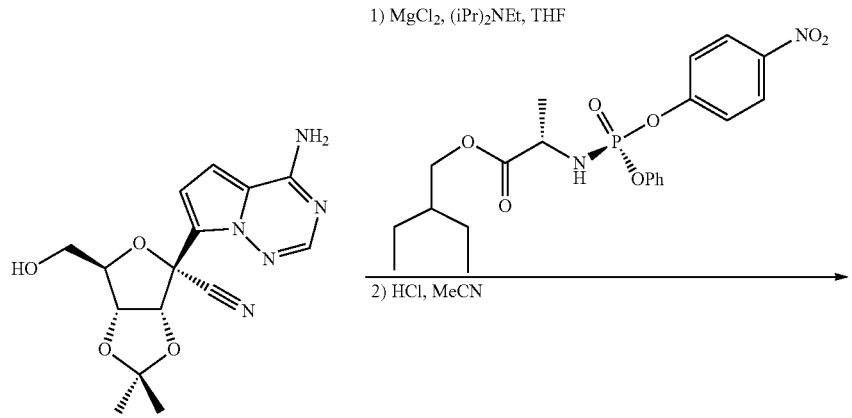

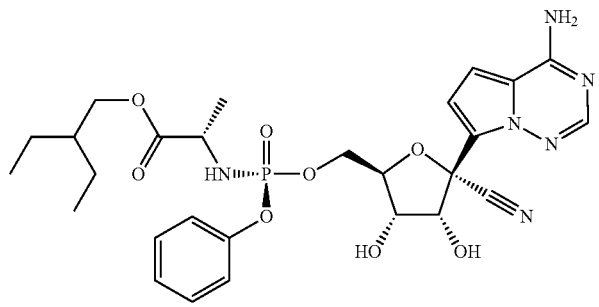

(3aR,4R,6R,6aR)-4-(4-Aminopyrrolo[2,1-f][1,2,4]triazin-7-yl)-6-(hydroxymethyl)-2,2-dimethyltetrahydrofuro[3,4-d][1,3]dioxole-4-carbonitrile (20 g, 60 mmol), 2-ethylbutyl ((S)-(4-nitrophenoxy)(phenoxy)phosphoryl)-L-alaninate (32 g, 72 mmol), and magnesium chloride (8.6 g, 90 mmol) were added to a reaction vessel. Tetrahydrofuran (about 200 mL) was added, followed by the addition of N,N-diisopropylethylamine (26 mL, 151 mmol) at about 20° C. After about 3 h, the reaction mixture was charged into a pre-cooled (about 15° C.) mixture of 2-methyltetrahydrofuran and aqueous citric acid (10 wt %). The organic and aqueous layers were separated, and the organic layer was washed with aqueous potassium carbonate (10 wt %, about 300 mL), aqueous potassium carbonate (10 wt %, two times about 200 mL), aqueous ammonium chloride (10 wt %, about 200 mL), and aqueous sodium chloride (15 wt %, about 200 mL). The solvent of the organic layer was exchanged to acetonitrile and the volume was adjusted to about 200 mL. The acetonitrile solution was cooled to about 0° C. and concentrated hydrochloric acid (about 40 mL) was added. After about 3 h, the reaction mixture was cooled to about −10° C., charged into a precooled (about 10° C.) mixture of 2-methyltetrahydrofuran (about 200 mL) and aqueous potassium bicarbonate (20 wt %, about 200 mL). The organic and aqueous layers were separated, and the organic layer was washed with aqueous potassium bicarbonate (20 wt %, about 100 mL), and aqueous sodium chloride (15 wt %, about 200 mL). The organic layer was concentrated to about 140 mL, and washed with aqueous sodium chloride (15 wt %, about 100 mL). The organic layer was concentrated and distilled from 2-methyltetrahydrofuran until the solution reached a target water content of no more than 0.2%. The 2-methyltetrahydrofuran solution (about 400 mL) was polish filtered and the solvent was exchanged to isopropyl acetate. The isopropyl acetate solution (about 100 mL) was stirred at about 21° C. Seeds containing a mixture of Form II and Form IV (about 40 mg) were added, and the suspension was stirred at about 21° C. for about 3 days. Crystalline Formula I containing a mixture of Form II and Form IV was isolated as a solid from the suspension by filtration and characterized as discussed below.

Example 6. Mixture II, A Mixture of Form II and Form IV

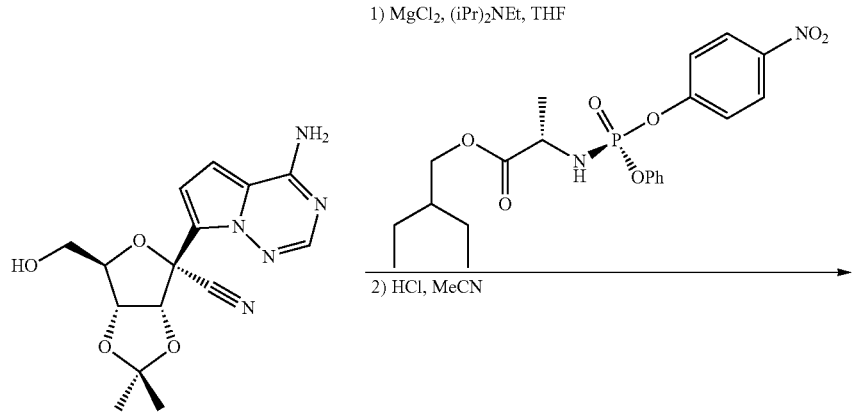

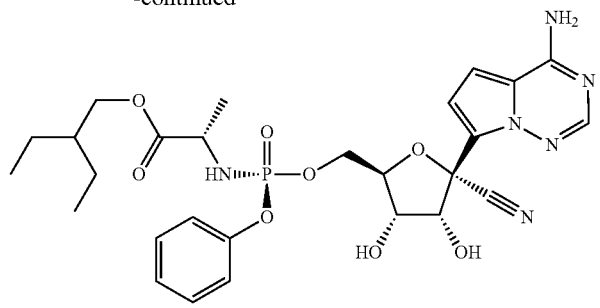

(3aR,4R,6R,6aR)-4-(4-Aminopyrrolo[2,1-f][1,2,4]triazin-7-yl)-6-(hydroxymethyl)-2,2-dimethyltetrahydrofuro[3,4-d][1,3]dioxole-4-carbonitrile (20 g, 60 mmol), 2-ethylbutyl ((S)-(4-nitrophenoxy)(phenoxy)phosphoryl)-L-alaninate (29 g, 63 mmol), and magnesium chloride (8.6 g, 90 mmol) were added to a reaction vessel. Tetrahydrofuran (about 200 mL) was added, followed by the addition of N,N-diisopropylethylamine (26 mL, 151 mmol) at about 20° C. After about 4 h, the reaction mixture was charged into a pre-cooled (about 10° C.) mixture of methyl tert-butyl ether (about 200 mL) and aqueous citric acid (10 wt %, about 200 mL). The organic and aqueous layers were separated, and the organic layer was washed with aqueous potassium carbonate (10 wt %, about 300 mL), aqueous potassium carbonate (10 wt %, two times about 200 mL), aqueous ammonium chloride (10 wt %, about 200 mL), and aqueous sodium chloride (15 wt %, about 200 mL). The solvent of the organic layer was exchanged to acetonitrile and the volume was adjusted to about 200 mL. The acetonitrile solution was cooled to about 0° C. and concentrated hydrochloric acid (about 40 mL) was added. After about 3 h, the reaction mixture was cooled to −10° C., charged into a precooled (about 10° C.) mixture of 2-methyltetrahydrofuran (about 200 mL) and aqueous potassium bicarbonate (20 wt %, about 200 mL). The organic and aqueous layers were separated, and the organic layer was washed with aqueous potassium bicarbonate (20 wt %, about 80 mL), and aqueous sodium chloride (15 wt %, about 200 mL). The organic layer was concentrated to about 100 mL, and washed with aqueous sodium chloride (15 wt %, about 100 mL). The organic layer was concentrated and distilled from 2-methyltetrahydrofuran until the solution reached a target water content of no more than 0.2%. The 2-methyltetrahydrofuran solution (about 400 mL) was polish filtered and the solvent was exchanged to isopropyl acetate. The isopropyl acetate solution (about 100 mL) was stirred at about 20° C. Seeds containing a mixture of Form II and Form IV (about 40 mg) were added, and the suspension was stirred at about 20° C. for about 3 days. Crystalline Formula I containing a mixture of Form II and Form IV was isolated as a solid from the suspension by filtration and characterized as discussed below.

Example 7. Mixture III, A Mixture of Form II and Form IV

Formula I (14.0 g) was added to a reaction vessel. Isopropyl alcohol (42 mL) and water (14 mL) were added and the suspension was heated to about 50° C. until dissolution was achieved. The solution was cooled to about 20° C., and about 14 mg of seeds containing a mixture of Form II and Form IV were added. Water (70 mL) was added over about 3 hours at about 20° C., and the suspension was stirred at about 20° C. for about 17 hours. Crystalline Formula I containing a mixture of Form II and Form IV was isolated as a solid from the suspension by filtration and characterized as discussed below.

Example 8. Formula I Maleate Form I

Dissolved 0.58 g (2S,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile in 5 mL isopropyl acetate (IPAc) in a 20 mL vial with stir bar. Added 4 mL IPAc and 0.25 mL ethanol to 150 mg maleic acid in a second vial and dissolved the maleic acid. Added the contents of the second vial to the 20 mL vial while stirring. After stirring for about 1 hour, the suspension was filtered, the filtrant washed with 2.5 mL IPAc, and air dried to isolate (2S,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile maleate salt.

A mixture of forms of Formula I (3.31 g) and isopropyl acetate (about 20 mL) were added to a first reaction vessel, which was capped and stirred magnetically at high speed. Maleic acid (0.72 g) was added to a second reaction vessel. Isopropyl acetate (about 20 mL) was added to the second reaction vessel. Methanol (about 5 mL) was added to the second reaction vessel. Methanol (about 5 mL) was added to the first reaction vessel. The second reaction vessel's contents were added to the first reaction vessel. The first reaction vessel was stirred at about 21° C. for about 5 minutes, and then seeded with (2S,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile maleate salt seeds. The first reaction vessel was capped and stirred at about 21° C. for about 18 hours. Formula I Maleate Form I was isolated as a solid from the suspension by centrifuge/filtration and characterized as discussed below.

Characterization of the Crystalline Forms

The crystalline forms of the present invention were characterized by various analytical techniques, including X-ray powder diffraction (XRPD), differential scanning calorimetry (DSC), thermogravimetric analysis (TGA), and dynamic vapor sorption (DVS) using the procedures described below.

X-Ray Powder Diffraction:

XRPD analysis was conducted on a diffractometer (PANalytical XPERT-PRO, PANanalytical B.V., Almelo, Netherlands) using copper radiation (Cu Kα, λ=1.5418 Å). Samples were prepared for analysis by depositing the powdered sample in the center of a steel holder equipped with a zero background plate. The generator was operated at a voltage of 45 kV and amperage of 40 mA. Slits used were Soller 0.02 rad., antiscatter 1.0°, and divergence. The sample rotation speed was 2 revolutions/second. Scans were performed from 2 to 40° 2θ during 5 min with a step size of 0.008° 2θ. Data analysis was performed by X'Pert Date Viewer version 2.2c (PANalytical B.V., Almelo, Netherlands) and X'Pert data viewer version 1.2d (PANalytical B.V., Almelo, Netherlands).

The XRPD pattern for Formula I Form I is represented in FIG. 1.

The XRPD pattern for Formula I Form II is represented in FIG. 5.

The calculated XRPD pattern for Formula I Form III represented in FIG. 9 was calculated by using Mercury 3.1 Development (Build RC5). Single crystal data for Formula I Form III was input into Mercury 3.1 to calculate the XRPD pattern for Formula I Form III.

The XRPD pattern for Formula I Form IV is represented in FIG. 10.

The XRPD pattern for Formula I Mixture I is represented in FIG. 13.

The XRPD pattern for Formula I Mixture II is represented in FIG. 16.

The XRPD pattern for Formula I Mixture III represented in FIG. 19.

The XRPD pattern for Formula I Maleate Form I is represented in FIG. 22.

The XRPD pattern for Formula I Form IV is represented in FIG. 26.

Differential Scanning Calorimetry:

Thermal properties were evaluated using a Differential Scanning Calorimetry (DSC) instrument (TA Q1000, TA Instruments, New Castle, Del., USA). Approximately 1 to 10 mg of solid sample was placed in a standard aluminum pan vented with a pinhole for each experiment and heated at a rate of 5 to 10° C./min under a 50 mL/min nitrogen purge. Data analysis was conducted using Universal Analysis 2000 Version 4.7A (TA Instruments, New Castle, Del., USA).

The DSC for Formula I Form I is represented in FIG. 2.
The DSC for Formula I Form II is represented in FIG. 6.
The DSC for Formula I Form IV is represented in FIG. 11.
The DSC for Formula I Mixture I is represented in FIG. 14.
The DSC for Formula I Mixture II is represented in FIG. 17.
The DSC for Formula I Mixture III is represented in FIG. 20.
The DSC for Formula I Maleate Form I is represented in FIG. 23.

Thermogravimetric Analysis:

Thermogravimetric analysis (TGA) was performed on a TGA instrument (TA Q500, TA Instruments, New Castle, Del., USA). Approximately 1 to 10 mg of solid sample was placed in an open aluminum pan for each experiment and heated at a rate of 5 to 10° C./min under a 60 mL/min nitrogen purge using. Data analysis was conducted using Universal Analysis 2000 Version 4.7A (TA Instruments, New Castle, Del., USA).

The TGA for Formula I Form I is represented in FIG. 3.
The TGA for Formula I Form II is represented in FIG. 7.
The TGA for Formula I Form IV is represented in FIG. 12.
The TGA for Formula I Mixture I is represented in FIG. 15.
The TGA for Formula I Mixture II is represented in FIG. 18.
The TGA for Formula I Mixture III is represented in FIG. 21.

The TGA for Formula I Maleate Form I is represented in FIG. 24.

Dynamic Vapor Sorption:

The hygroscopicity was evaluated at room temperature using a dynamic vapor sorption (DVS) instrument (TGA Q5000 TA Instruments, New Castle, Del.). Water adsorption and desorption were studied as a function of relative humidity (RH) over the range of 0 to 90% at 25° C. The relative humidity in the chamber was increased by 10% RH and held until the solid and atmosphere reached equilibration. The equilibrium test was continued until passed or expired after 5 or 10 hours. At this point, RH was raised 10% higher and the process was repeated until 90% RH was reached and equilibrated. During this period, the water sorption was monitored. For desorption, the relative humidity was decreased in a similar manner to measure a full sorption/desorption cycle. The cycle was optionally repeated. All experiments were operated in dm/dt mode (mass variation over time) to determine the equilibration endpoint. Approximately 5-10 mg of solid was used. Data analysis was conducted using Universal Analysis 2000 Version 4.7A (TA Instruments, New Castle, Del., USA).

The DVS for Formula I Form I is represented in FIG. 4.
The DVS for Formula I Form II is represented in FIG. 8.
The DVS for Formula I Maleate Form I is represented in FIG. 25.

The single crystal X-ray diffraction studies were carried out on a Bruker APEX II Ultra diffractometer equipped with Mo $K_\alpha$ radiation (e.g. Wavelength). Crystals of the subject compound were cut into a 0.22×0.18×0.04 mm section and mounted on a Cryoloop with Paratone-N oil. Data were collected in a nitrogen gas stream at a particular temperature as shown in the Tables below (e.g. 100(2) K or 200(2) K). A total number of reflections were collected covering the indices, (e.g. $-9<=h<=10$, $-13<=k<=16$, $-37<=l<=36$). Certain reflections were found to be symmetry independent, with a $R_{int}$ value. Indexing and unit-cell refinement indicated a crystal system (e.g. monoclinic, triclinic, or orthorhombic lattice). The space group, which was uniquely defined by the systematic absences in the data, was found (e.g. P1, P2(1), C2, and P21212). The data were integrated using the Bruker SAINT software program and scaled using the SADABS software program. Solution by direct methods (SHELXT) produced a complete phasing model compatible with the proposed structure.

All non-hydrogen atoms were refined anisotropically by full-matrix least-squares (SHELXL-2014). All hydrogen atoms were placed using a riding model. Their positions were constrained relative to their parent atom using the appropriate HFIX command in SHELXL-2014. Crystallographic data are summarized in tables below. The absolute stereochemistry was set to conform to previously studied samples of the same compound.

The single crystal X-ray crystallography data for Formula I Form II is summarized in Table 2A below.

TABLE 2A

| Single Crystal Data for Formula I Form II | |
|---|---|
| Empirical Formula | $C_{27}H_{35}N_6O_8P$ |
| Form and Identification | Form II |
| Solvents in Structure | Isopropyl Alcohol |
| Acquisition Temperature | 100(2) K |
| Space Group | P 21 |
| Z value | 2 |
| Density (Mg/m³) | 1.373 |

TABLE 2A-continued

Single Crystal Data for Formula I Form II

Unit Cell Dimensions

| | Distance (Å) | | Angle (°) |
|---|---|---|---|
| a | 10.505 (2) | α | 90 |
| b | 12.736 (3) | β | 100.105 (7) |
| c | 11.066 (2) | γ | 90 |

The single crystal X-ray crystallography data for Formula I Form III is summarized in Table 2B below.

TABLE 2B

Single Crystal Data for Formula I Form III

| Empirical Formula | $C_{28}H_{39}N_6O_9Cl_2P$ |
|---|---|
| Form and Identification | Form III |
| Solvents in Structure | Dichloromethane |
| Acquisition Temperature | 100(2) K |
| Space Group | P 21 |
| Z value | 2 |
| Density (Mg/m³) | 1.348 |

Unit Cell Dimensions

| | Distance (Å) | | Angle (°) |
|---|---|---|---|
| a | 10.5800 (4) | α | 90 |
| b | 7.4526 (4) | β | 92.500 (3) |
| c | 21.5691 (12) | γ | 90 |

The purity profile of various forms of Formula I is summarized in Table 3 below,

TABLE 3

Purity Profile

| | | Purity | Impurity (%) | | | | | | | |
|---|---|---|---|---|---|---|---|---|---|---|
| Entry | Sample | (%) | A | B | C | D | E | F | G | H |
| 1 | Mixture II[1] | 97.6 | 0.36 | 0.12 | 0.64 | 0.79 | 0.04 | 0.06 | 0.27 | 0.03 |
| 2 | Mixture I[1] | 97.7 | 0.41 | 0.08 | 0.46 | 0.64 | 0.10 | 0.11 | 0.21 | 0.04 |
| 3 | Mixture III[2] | 98.9 | 0.10 | ND | 0.14 | 0.50 | 0.08 | 0.09 | 0.14 | 0.03 |
| 4 | Form II[3] | 99.5 | 0.04 | ND | 0.06 | 0.36 | 0.03 | 0.04 | 0.05 | 0.02 |

[1]Prepared using iPAc at 20° C.
[2]Prepared from Entry 2 by dissolving in IPA/Water (3:1 V/V) at 50° C. followed by addition of water (5 V) for a final solvent mixture of IPA/Water (3:6 V/V).
[3]Prepared from Entry 1 in IPA/Water (1:2 V/V) at 50° C. without dissolution of solids.

wherein Impurity A is (2R,3R,4S,5R)-2-(4-aminopyrrolo[2,1-f][1,2,4]triazin-7-yl)-3,4-dihydroxy-5-(hydroxymethyl) tetrahydrofuran-2-carbonitrile:

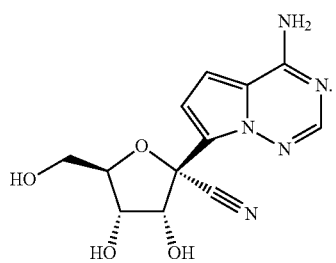 [SMILES: N#C[C@@]1(c2ccc3c(N)ncnn23)O[C@H](CO)[C@@H](O)[C@H]1O]

In some embodiments of the invention, Formula I is hydrated. In some embodiments, ratio of Formula I to water molecules is 1:1.

Solid State NMR:

Solid-state NMR (SSNMR) experiments were performed on a Bruker Avance I spectrometer (Bruker, Billerica, Mass.) operating at 100.51 MHz for $^{13}C$ and 399.66 MHz for $^1H$. A Chemagnetics (Ft. Collins, Colo.) Apex probe, refitted with a 7 mm magic angle spinning (MAS) system (Revolution NMR, Ft. Collins, Colo.), was used to acquire the data. Each sample was packed into a 7 mm zirconia rotor. All experiments were acquired using cross polarization and magic-angle spinning (CP/MAS). Magic angle spinning speeds were typically 5 kHz. Chemical shifts are reported relative to TMS via a secondary reference of the methyl peak of 3-methylglutaric acid at 18.84 ppm with an accuracy of ±0.2 ppm. Spinning sidebands were eliminated using total sideband suppression (TOSS). Saturation recovery was used to measure $^1H$ $T_1$ relaxation times.

Data collection was done at a nominal temperature of ~8.5° C. Acquisition parameters included a 1.5 ms cross polarization time, ~50 ms acquisition time, and are cycle delay of ~2× the $^1H$ $T_1$ (~3.2 seconds). $^1H$ decoupling of ~64 kHz was used during acquisition. Data was processed in Bruker Topspin 2.1© software package. The free induction decay was Fourier transformed, phased, and baseline corrected.

Solid state NMR for Formula I Form II is represented in FIG. 27.

Solid state NMR for a mixture of Formula I Form II and Form IV (top), Mixture III (middle) and Mixture I (bottom) are represented in FIG. 28.

Solid state NMR for Mixture III (top), a mixture of Formula I Form II and Form IV (middle), and Mixture II (bottom) are represented in FIG. 29.

Competition Experiments

Several experiments were conducted demonstrating the Formula I Form II is the more stable form.

Formula I was mixed with the corresponding solvent and mixed at room temperature via agitator with no stir bar. XRPD of isolated solids was acquired after two weeks.

| Experiment | Solvent | XRPD |
|---|---|---|
| 10 | Methanol | Solution; no XRPD |
| 12 | 1-propanol | Partially converted to Form II |
| 14 | THF | |
| 16 | 2-propanol | |
| 18 | ACN | Form II |
| 20 | DCM | Partially converted to Form II |
| 22 | Ethanol | Form II |
| 24 | MTBE | Partially converted to Form II |
| 26 | 2MeTHF | |
| 28 | EtOAc/water | Form II |

| Experiment | Solvent | XRPD |
|---|---|---|
| 30 | MEK | |
| 32 | Ethanol/water $a_w$ 0.4 | |

A competition experiment between Formula I Form I and Formula I Form II was conducted by mixing Formula I Form I with isopropyl acetate, followed by adding Mixture II, a mixture of Formula I Form II and Formula I Form IV.

| Experiment | Formula I Form I (mg) | Formula I Mixture II (mg) | IPAc (mg) | mg/g | Comment |
|---|---|---|---|---|---|
| 26 | 11 | 55.4 | 889 | 75 | Suspension; conversion to Form II in 1 day |

A competition experiment between Formula I Form II and Formula I Form IV was conducted by combining Formula I Mixture II with IPA/Water (3/6 V/V) at 50° C. for several days. All experiments showed conversion to Formula I Form II.

| Experiment | wt % water | Duration (days in suspension) | Temp. | XRPD | DSC | Comment |
|---|---|---|---|---|---|---|
| 023 | 9.3 | 1 | 50 | Form II | Form II | suspension |
| 030 | 4.9 | 1; 3 | 50 | Form II | Form II | |
| 033 | 39.5 | 3 | 50 | Form II | Form II | weak suspension; strong suspension after 3 days |
| 034 | 49.9 | 1; 3 | 50 | Form II | Form II | suspension |
| 037 | 0.93 | 2 | 50, 22 | NA | Form II | suspension; Form II at 50 C. and 22 C. (after slow cool and overnight stirring) |

Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application. Each of the references including all patents, patent applications and publications cited in the present application is incorporated herein by reference in its entirety, as if each of them is individually incorporated.

Further, it would be appreciated that, in the above teaching of invention, the skilled in the art could make certain changes or modifications to the invention, and these equivalents would still be within the scope of the invention defined by the appended claims of the application.

What is claimed is:

1. A crystalline form of (S)-2-ethylbutyl 2-(((S)-(((2R,3S,4R,5R)-5-(4-aminopyrrolo [2,1-f][1,2,4]triazin-7-yl)-5-cyano-3,4-dihydroxytetrahydrofuran-2-yl)methoxy)(phenoxy) phosphoryl)amino)propanoate, wherein the crystalline form is characterized by an X-ray powder diffraction (XRPD) pattern having peaks at about 22.3°, 16.9°, and 16.2° 2-θ±0.2° 2-θ.

2. The crystalline form of claim 1, characterized by a unit cell as determined by single crystal X-ray crystallography of the following dimensions: a=10.505 (2) Å; b=12.736 (3) Å; c=11.066 (2) Å; α=90°; β=100.105 (7)° and γ=90.

3. The crystalline form of claim 1, characterized by a Differential Scanning Calorimetry (DSC) thermogram peak at 138° C.

4. A pharmaceutical composition comprising a crystalline form of claim 1 and a pharmaceutically acceptable excipient.

5. The crystalline form of claim 1, wherein the X-ray powder diffraction (XRPD) pattern has further peaks at about 13.8° and 12.7° 2-θ±0.2° 2-θ.

6. The crystalline form of claim 1, wherein the X-ray powder diffraction (XRPD) pattern has further peaks at about 22.5°, 10.6° and 14.5° 2-θ±0.2° 2-θ.

7. The crystalline form of claim 1, wherein the X-ray powder diffraction (XRPD) pattern has peaks at about 22.3°, 16.9°, 16.2°, 13.8°, 12.7°, 22.5°, 10.6° and 14.5° 2-θ±0.2° 2-θ.

8. The crystalline form of claim 1, characterized by one or more of the following:
    an X-ray powder diffraction (XRPD) pattern further having peaks at about 22.3°, 16.9°, 16.2°, 13.8°, 12.7°, 22.5°, 10.6° and 14.5° 2-θ±0.2° 2-θ;
    a Differential Scanning calorimetry (DSC) thermogram peak at 138° C.; and
    a unit cell as determined by single crystal X-ray crystallography of the following dimensions: a=10.505 (2) Å; b=12.736 (3) Å; c=11.066 (2) Å; α=90°; β=100.105 (7)°; and γ=90.

9. The crystalline form of claim 1, characterized by an X-ray powder diffraction (XRPD) pattern as set forth in FIG. 5.

10. The crystalline form of claim 1, characterized by differential scanning calorimetry (DSC) pattern as set forth in FIG. 6.

11. The crystalline form of claim 1, characterized by thermogravimetric analysis (TGA) pattern as set forth in FIG. 7.

12. The crystalline form of claim 1, characterized by dynamic vapor sorption (DVS) pattern as set forth in FIG. 8.

* * * * *